US011096940B2

(12) United States Patent
Filvaroff et al.

(10) Patent No.: US 11,096,940 B2
(45) Date of Patent: Aug. 24, 2021

(54) TREATMENT OF HEPATOCELLULAR CARCINOMA CHARACTERIZED BY HEPATITIS B VIRUS INFECTION

(71) Applicant: Celgene Corporation, Summit, NJ (US)

(72) Inventors: Ellen Filvaroff, San Francisco, CA (US); Kristen M. Hege, Burlingame, CA (US); Shaoyi Li, Warren, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 16/624,301

(22) PCT Filed: Jun. 21, 2018

(86) PCT No.: PCT/US2018/038697
§ 371 (c)(1),
(2) Date: Dec. 19, 2019

(87) PCT Pub. No.: WO2018/237114
PCT Pub. Date: Dec. 27, 2018

(65) Prior Publication Data
US 2020/0121676 A1    Apr. 23, 2020

Related U.S. Application Data

(60) Provisional application No. 62/523,688, filed on Jun. 22, 2017.

(51) Int. Cl.
| *A61K 31/4427* | (2006.01) |
| *A61P 35/00* | (2006.01) |
| *A61K 31/4985* | (2006.01) |
| *A61K 31/44* | (2006.01) |
| *A61K 31/517* | (2006.01) |
| *A61K 39/395* | (2006.01) |
| *A61K 45/06* | (2006.01) |
| *A61K 39/00* | (2006.01) |

(52) U.S. Cl.
CPC .......... *A61K 31/4985* (2013.01); *A61K 31/44* (2013.01); *A61K 31/517* (2013.01); *A61K 39/3955* (2013.01); *A61K 45/06* (2013.01); *A61P 35/00* (2018.01); *A61K 2039/505* (2013.01)

(58) Field of Classification Search
CPC .......................... A61K 31/4427; A61P 35/00
USPC ......................................................... 514/338
See application file for complete search history.

(56) References Cited

U.S. PATENT DOCUMENTS

| 3,507,866 A | 4/1970 | Jones et al. |
| 3,567,725 A | 3/1971 | Grabowski et al. |
| 4,294,836 A | 10/1981 | Lesher et al. |
| 4,294,837 A | 10/1981 | Lesher et al. |
| 4,309,537 A | 1/1982 | Lesher et al. |
| 4,317,909 A | 3/1982 | Lesher et al. |
| 4,898,872 A | 2/1990 | Campbell et al. |
| 4,963,561 A | 10/1990 | Lesher et al. |
| 5,424,311 A | 6/1995 | Billhardt-Troughton |
| 5,811,097 A | 9/1998 | Allison et al. |
| 5,855,887 A | 1/1999 | Allison et al. |
| 5,869,659 A | 2/1999 | Stolle et al. |
| 6,031,105 A | 2/2000 | Wright |
| 6,051,227 A | 4/2000 | Allison et al. |
| 6,093,728 A | 7/2000 | McMahon et al. |
| 6,207,157 B1 | 3/2001 | Gu et al. |
| 6,372,740 B1 | 4/2002 | Murata et al. |
| 6,566,367 B2 | 5/2003 | Bakthavatchalam et al. |
| 6,682,736 B1 | 1/2004 | Hanson et al. |
| 6,791,006 B2 | 9/2004 | Nezu et al. |
| 6,800,436 B1 | 10/2004 | Jenne et al. |
| 6,825,184 B2 | 11/2004 | Ciriillo et al. |
| 6,855,723 B2 | 2/2005 | McMahon et al. |
| 6,984,720 B1 | 1/2006 | Korman et al. |
| 7,199,119 B2 | 4/2007 | Burkitt et al. |
| 7,247,621 B2 | 7/2007 | Hong et al. |
| 7,429,572 B2 | 9/2008 | Clark |
| 7,476,665 B2 | 1/2009 | Burgey |
| 7,488,802 B2 | 2/2009 | Colins et al. |
| 7,605,238 B2 | 10/2009 | Korman et al. |
| 7,608,622 B2 | 10/2009 | Liu et al. |
| 7,651,687 B2 | 1/2010 | Buck et al. |
| 7,700,594 B2 | 4/2010 | Chen et al. |
| 7,709,517 B2 | 5/2010 | Sawyers et al. |
| 7,767,687 B2 | 8/2010 | Oslob et al. |

(Continued)

FOREIGN PATENT DOCUMENTS

| CA | 2 458 699 A1 | 3/2003 |
| DE | 262 026 | 11/1988 |

(Continued)

OTHER PUBLICATIONS

Advisory Action dated Aug. 17, 2011 for U.S. Appl. No. 12/605,791.
Advisory Action dated Sep. 14, 2011 for U.S. Appl. No. 12/605,791.
Agredano-Moreno et al., "Distinctive expression and functional regulation of the maize (Zea mays L.) TOR kinase ortholog," Molecular BioSystems, 3(11):794-802 (2007).
Agulnik, "New developments in mammalian target of rapamycin inhibitors for the treatment of sarcoma," Cancer, vol. 118, No. 6, Aug. 11, 2011 (Aug. 11, 2011), pp. 1486-1497.
Alwi et al., "In vivo modulation of 4E binding protein 1 (4E-BP1) phosphorylation by watercress: a pilot study," Br. J. Nutrition, 104:1288-1296 (2010).

(Continued)

*Primary Examiner* — Raymond J Henley, III
(74) *Attorney, Agent, or Firm* — Jones Day

(57) ABSTRACT

Provided herein are methods for treating and/or preventing hepatocellular carcinoma (HCC) characterized by hepatitis B virus (HBV) infection in a patient, comprising administering an effective amount of 7-(6-(2-hydroxypropan-2-yl) pyridin-3-yl)-1-((trans)-4-methoxycyclohexyl)-3,4-dihydropyrazino[2,3-b]pyrazin-2(1H)-one or a pharmaceutically acceptable salt or tautomer thereof (collectively referred to herein as "Compound 1") to the patient having HCC characterized by HBV infection.

42 Claims, 13 Drawing Sheets

(56) References Cited

U.S. PATENT DOCUMENTS

| | | |
|---|---|---|
| 7,902,187 B2 | 3/2011 | Neagu et al. |
| 7,919,490 B2 | 4/2011 | Neagu et al. |
| 7,943,743 B2 | 5/2011 | Korman et al. |
| 7,968,556 B2 | 6/2011 | Mortensen et al. |
| 7,981,893 B2 | 7/2011 | Mortensen et al. |
| 8,008,449 B2 | 8/2011 | Korman et al. |
| 8,110,578 B2 | 2/2012 | Perrin-Ninkovic et al. |
| 8,158,605 B2 | 4/2012 | Silverman et al. |
| 8,168,757 B2 | 5/2012 | Finnefrock et al. |
| 8,217,149 B2 | 7/2012 | Irving et al. |
| 8,268,809 B2 | 9/2012 | Kalman |
| 8,372,976 B2 | 2/2013 | Mortensen et al. |
| 8,383,634 B2 | 2/2013 | Mortensen et al. |
| 8,492,381 B2 | 7/2013 | Perrin-Ninkovic et al. |
| 8,507,492 B2 | 8/2013 | Perrin-Ninkovic et al. |
| 8,569,494 B2 | 10/2013 | Harris et al. |
| 8,628,931 B2 | 1/2014 | Liotta et al. |
| 8,642,660 B2 | 2/2014 | Goldfarb |
| 8,686,135 B2 | 4/2014 | Jokiel et al. |
| 8,906,932 B2 | 12/2014 | Muller et al. |
| 8,907,087 B2 | 12/2014 | Perrin-Ninkovic et al. |
| 9,006,224 B2 | 4/2015 | Wayne et al. |
| 9,079,900 B2 | 7/2015 | Harris et al. |
| 9,155,736 B2 | 10/2015 | Xu et al. |
| 9,358,232 B2 | 6/2016 | Hege et al. |
| 9,359,364 B2 | 6/2016 | Menon et al. |
| 9,375,443 B2 | 6/2016 | Xu et al. |
| 9,403,829 B2 | 8/2016 | Connolly et al. |
| 9,416,134 B2 | 8/2016 | Eckert |
| 9,474,757 B2 | 10/2016 | Hege et al. |
| 9,493,466 B2 | 11/2016 | Xu et al. |
| 9,505,764 B2 | 11/2016 | Raymon et al. |
| 9,512,129 B2 | 12/2016 | Eckert |
| 9,555,033 B2 | 1/2017 | Chopra et al. |
| 9,604,939 B2 | 3/2017 | Beauchamps et al. |
| 9,630,966 B2 | 4/2017 | Raymon et al. |
| 9,737,535 B2 | 8/2017 | Fultz et al. |
| 9,771,371 B2 | 9/2017 | Elsner et al. |
| 9,782,427 B2 | 10/2017 | Raymon |
| 9,937,170 B2 | 4/2018 | Xu et al. |
| 10,004,735 B2 | 6/2018 | Fultz et al. |
| 2003/0036652 A1 | 5/2003 | Bakthavatchalam et al. |
| 2003/0162968 A1 | 8/2003 | Ciriillo et al. |
| 2004/0023921 A1 | 2/2004 | Hong et al. |
| 2004/0063658 A1 | 4/2004 | Roberts et al. |
| 2004/0097485 A1 | 5/2004 | Burkitt et al. |
| 2004/0213757 A1 | 10/2004 | Zhu et al. |
| 2005/0009737 A1 | 1/2005 | Clark |
| 2006/0004014 A1 | 1/2006 | Hoffmann et al. |
| 2006/0106022 A1 | 5/2006 | Liu et al. |
| 2006/0135511 A1 | 6/2006 | Burgey |
| 2006/0142269 A1 | 6/2006 | Dykes |
| 2006/0211702 A1 | 9/2006 | Oslob et al. |
| 2006/0216776 A1 | 9/2006 | Abraham et al. |
| 2007/0036793 A1 | 2/2007 | Hardie et al. |
| 2007/0112005 A1 | 5/2007 | Chen et al. |
| 2007/0149521 A1 | 6/2007 | Crew et al. |
| 2007/0238745 A1 | 10/2007 | Mohapatra et al. |
| 2008/0194019 A1 | 8/2008 | Cantley et al. |
| 2008/0214580 A1 | 9/2008 | Neagu et al. |
| 2009/0023724 A1 | 1/2009 | Mortensen et al. |
| 2009/0042890 A1 | 2/2009 | Mortensen et al. |
| 2009/0069289 A1 | 3/2009 | Neagu et al. |
| 2009/0124811 A1 | 5/2009 | Coquerel et al. |
| 2009/0163468 A1 | 6/2009 | Chen et al. |
| 2009/0163545 A1 | 6/2009 | Goldfard |
| 2009/0181963 A1 | 7/2009 | Dehnhardt et al. |
| 2009/0186929 A1 | 7/2009 | Weinberg et al. |
| 2009/0209482 A1 | 8/2009 | Silverman et al. |
| 2009/0215812 A1 | 8/2009 | Bedrosian et al. |
| 2009/0281075 A1 | 11/2009 | Roughton et al. |
| 2010/0029610 A1 | 2/2010 | Singh et al. |
| 2010/0144738 A1 | 6/2010 | Bornmann et al. |
| 2010/0216781 A1 | 8/2010 | Perrin-Ninkovic et al. |
| 2010/0249092 A1 | 9/2010 | Singh et al. |
| 2010/0249122 A1 | 9/2010 | Kalman |
| 2010/0324112 A1 | 12/2010 | Golin et al. |
| 2011/0137028 A1 | 6/2011 | Harris et al. |
| 2011/0223157 A1 | 9/2011 | Schafer et al. |
| 2011/0257167 A1 | 10/2011 | Chopra et al. |
| 2011/0257206 A1 | 10/2011 | Burke et al. |
| 2011/0318336 A1 | 12/2011 | Petricoin et al. |
| 2012/0028972 A1 | 2/2012 | Wong et al. |
| 2012/0046457 A1 | 2/2012 | Kolla et al. |
| 2012/0059164 A1 | 3/2012 | Perrin-Ninkovic et al. |
| 2012/0071658 A1 | 3/2012 | Perrin-Ninkovic et al. |
| 2012/0077832 A1 | 3/2012 | Witowski et al. |
| 2012/0230983 A1 | 9/2012 | Muller et al. |
| 2012/0238562 A1 | 9/2012 | Cinar et al. |
| 2013/0102613 A1 | 4/2013 | Xu et al. |
| 2013/0142873 A1 | 6/2013 | Assaf et al. |
| 2013/0158023 A1 | 6/2013 | Ning et al. |
| 2013/0225518 A1 | 8/2013 | Xu et al. |
| 2013/0245026 A1 | 9/2013 | Xu et al. |
| 2013/0245027 A1 | 9/2013 | Xu et al. |
| 2013/0245028 A1 | 9/2013 | Xu et al. |
| 2013/0245029 A1 | 9/2013 | Xu et al. |
| 2013/0245254 A1 | 9/2013 | Harris et al. |
| 2014/0046057 A1 | 2/2014 | Cohen et al. |
| 2014/0100256 A1 | 4/2014 | Lorenz et al. |
| 2014/0113904 A1 | 4/2014 | Mortensen et al. |
| 2014/0113905 A1 | 4/2014 | Xu et al. |
| 2014/0162282 A1 | 6/2014 | Schafer et al. |
| 2014/0296312 A1 | 10/2014 | Protter et al. |
| 2014/0314673 A1 | 10/2014 | Raymon et al. |
| 2014/0314674 A1 | 10/2014 | Raymon et al. |
| 2014/0314751 A1 | 10/2014 | Hege et al. |
| 2014/0314752 A1 | 10/2014 | Lopez-Girona et al. |
| 2014/0314753 A1 | 10/2014 | Lopez-Girona et al. |
| 2014/0315848 A1 | 10/2014 | Raymon et al. |
| 2014/0315900 A1 | 10/2014 | Raymon |
| 2014/0315907 A1 | 10/2014 | Raymon |
| 2014/0315908 A1 | 10/2014 | Menon et al. |
| 2015/0099754 A1 | 4/2015 | Xu et al. |
| 2015/0174128 A1 | 6/2015 | Tester et al. |
| 2015/0297590 A1 | 10/2015 | Fultz et al. |
| 2015/0297605 A1 | 10/2015 | Trowe |
| 2015/0299209 A1 | 10/2015 | Boersen et al. |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002/100363 | 4/2002 |
| JP | 2002167387 | 6/2002 |
| WO | WO 1999/16438 | 4/1999 |
| WO | WO 1999/28320 | 6/1999 |
| WO | WO 1999/28459 | 6/1999 |
| WO | WO 2000/73306 | 12/2000 |
| WO | WO 2002/048152 | 6/2002 |
| WO | WO 2002/076954 | 10/2002 |
| WO | WO 2003/032989 | 4/2003 |
| WO | WO 2003/072557 | 9/2003 |
| WO | WO 2003/093290 | 11/2003 |
| WO | WO 2004/042002 | 5/2004 |
| WO | WO 2004/048365 | 6/2004 |
| WO | WO 2004/065378 | 8/2004 |
| WO | WO 2004/076454 | 9/2004 |
| WO | WO 2004/078754 | 9/2004 |
| WO | WO 2004/085409 | 10/2004 |
| WO | WO 2004/096797 | 11/2004 |
| WO | WO 2004/103274 | 12/2004 |
| WO | WO 2005/002584 | 1/2005 |
| WO | WO 2005/003147 | 1/2005 |
| WO | WO 2005/021519 | 3/2005 |
| WO | WO 2005/120511 | 12/2005 |
| WO | WO 2006/001266 | 1/2006 |
| WO | WO 2006/018182 | 2/2006 |
| WO | WO 2006/020755 | 2/2006 |
| WO | WO 2006/030031 | 3/2006 |
| WO | WO 2006/036883 | 4/2006 |
| WO | WO 2006/045828 | 5/2006 |
| WO | WO 2006/046031 | 5/2006 |

(56) References Cited

FOREIGN PATENT DOCUMENTS

| | | |
|---|---|---|
| WO | WO 2006/050076 | 5/2006 |
| WO | WO 2006/065703 | 6/2006 |
| WO | WO 2006/087530 | 8/2006 |
| WO | WO 2006/090167 | 8/2006 |
| WO | WO 2006/090169 | 8/2006 |
| WO | WO 2006/091737 | 8/2006 |
| WO | WO 2006/108103 | 10/2006 |
| WO | WO 2006/122053 | 11/2006 |
| WO | WO 2007/060404 | 3/2007 |
| WO | WO 2007/044698 | 4/2007 |
| WO | WO 2007/044729 | 4/2007 |
| WO | WO 2007/044813 | 4/2007 |
| WO | WO 2007/047754 | 4/2007 |
| WO | WO 2007/066099 | 6/2007 |
| WO | WO 2007/066102 | 6/2007 |
| WO | WO 2007/066103 | 6/2007 |
| WO | WO 2007/080382 | 7/2007 |
| WO | WO 2007/125321 | 11/2007 |
| WO | WO 2007/129044 | 11/2007 |
| WO | WO 2007/129052 | 11/2007 |
| WO | WO 2007/129161 | 11/2007 |
| WO | WO 2007/135398 | 11/2007 |
| WO | WO 2007/143212 | 12/2007 |
| WO | WO 2008/016669 | 2/2008 |
| WO | WO 2008/023161 | 2/2008 |
| WO | WO 2008/032027 | 3/2008 |
| WO | WO 2008/032028 | 3/2008 |
| WO | WO 2008/032033 | 3/2008 |
| WO | WO 2008/032036 | 3/2008 |
| WO | WO 2008/032060 | 3/2008 |
| WO | WO 2008/032064 | 3/2008 |
| WO | WO 2008/032072 | 3/2008 |
| WO | WO 2008/032077 | 3/2008 |
| WO | WO 2008/032089 | 3/2008 |
| WO | WO 2008/032091 | 3/2008 |
| WO | WO 2008/051493 | 5/2008 |
| WO | WO 2008/051494 | 5/2008 |
| WO | WO 2008/060546 | 5/2008 |
| WO | WO 2008/064093 | 5/2008 |
| WO | WO 2008/115974 | 9/2008 |
| WO | WO 2008/140947 | 11/2008 |
| WO | WO 2008/156712 | 12/2008 |
| WO | WO 2009/007748 | 1/2009 |
| WO | WO 2009/007749 | 1/2009 |
| WO | WO 2009/007750 | 1/2009 |
| WO | WO 2009/007751 | 1/2009 |
| WO | WO 2009/008992 | 1/2009 |
| WO | WO 2009/052145 | 4/2009 |
| WO | WO 2009/102986 | 9/2009 |
| WO | WO 2009/126926 | 10/2009 |
| WO | WO 2010/006072 | 1/2010 |
| WO | WO 2010/022243 | 2/2010 |
| WO | WO 2010/036959 | 4/2010 |
| WO | WO 2010/044893 | 4/2010 |
| WO | WO 2010/056311 | 5/2010 |
| WO | WO 2010/057048 | 5/2010 |
| WO | WO 2010/062571 | 6/2010 |
| WO | WO 2010/068483 | 6/2010 |
| WO | WO 2010/089411 | 8/2010 |
| WO | WO 2010/093435 | 8/2010 |
| WO | WO 2011/031965 | 3/2011 |
| WO | WO 2011/053518 | 5/2011 |
| WO | WO 2011/066342 | 6/2011 |
| WO | WO 2011/079114 | 6/2011 |
| WO | WO 2011/082400 | 7/2011 |
| WO | WO 2011/097333 | 8/2011 |
| WO | WO 2011/112666 | 9/2011 |
| WO | WO 2011/133668 | 10/2011 |
| WO | WO 2011/159877 | 12/2011 |
| WO | WO 2011/161699 | 12/2011 |
| WO | WO 2012/016113 | 2/2012 |
| WO | WO 2012/021444 | 2/2012 |
| WO | WO 2013/059396 | 4/2013 |
| WO | WO 2013/063401 | 5/2013 |
| WO | WO 2013/075059 | 5/2013 |
| WO | WO 2013/082344 | 6/2013 |
| WO | WO 2013/096907 | 6/2013 |
| WO | WO 2013/138553 | 9/2013 |
| WO | WO 2013/138556 | 9/2013 |
| WO | WO 2013/138557 | 9/2013 |
| WO | WO 2014/081714 | 5/2014 |

OTHER PUBLICATIONS

Amornphimoltham et al., "A retroinhibition approach reveals a tumor cell-autonomous response to rapamycin in head and neck cancer," Cancer Research, vol. 68(4), pp. 1144-1153 (2008).

Anonymous, "Ridaforolimus," *Drugs RD*, 10(3):165-178 (2010).

Antonarakis et al., "Novel targeted therapeutics for metastatic castration-resistant prostate cancer," Cancer Letters, vol. 291, No. 1, May 1, 2010 (May 1, 2010), pp. 1-13.

Armstrong et al., (2010), "A pharmacodynamic study of rapamycin in men with intermediate-to high-risk localized prostate cancer," *Clinical cancer research*, 16.11 (2010): 3057-306.

Arzumanyan et al., "Pathogenic mechanisms in HBV- and HCV-associated hepatocellular carcinoma," Nature Rev., 13:123-135 (2013).

Balamuth et al., "Ewing's sarcoma," Lancet Oncology, Lancet Publishing Group, London, Great Britain, vol. 11, No. 2, Feb. 1, 2010 (Feb. 1, 2010), pp. 184-192.

Barlin 1982, "Purine analogs as amplifiers of phleomycin. VII. Some 1H-inidazo[4,5-b]pyrazines and related compound," Australian Journal of Chemistry, vol. 35:2299-2306.

Baselga et al., "Phase II randomized study of neoadjuvant everolimus plus letrozole compared with placebo plus letrozole in patients with estrogen receptor-positive breast cancer," J. Clin. Oncol. 27(16):2630-2637 (2009).

BD™ PHOSFLOW, "Technical Data Sheet—Alexa Fluor® 647 Mouse anti-4EBP1 (pT36/pT45)," p. 1-2, retrieved Jun. 2010.

Beresnev et al., 2000, "Interaction of 5-methoxy-1,2,4-traizines with uras as a new route to 6-azapurines," Medeleev Commu., vol. 2:58-59.

Bergmann et al., 1963, "2-Phenylpurines, their chemical and enzumological reactivity," J. Chem Org. , pp. 3729-3735.

Berk et al., "Analysis of the pharmacodynamic activity of the mTOR inhibitor ridaforolimus (AP23573, MK-8669) in a phase 1 clinical trial," Cancer Chemother. Pharmacol., vol. 69(5), pp. 1369-1377 (2012).

Blau, "Molecular investigation of Ewing sarcoma: about detecting translocations," EMBO molecular medicine 4.6 (2012): 449-450.

Booth et al., 1992, "Synthesis of 9-Hydroxyalkyl-substituted purines from the corresponding 4-(C-Cyanofonnimidoyl)imidazole-5-amines," J, Chem Society, Perkin Transactions 1: Organic and Bio-Organic Chemstry, vol. 2119-26.

Booth et al., 1995, "Synthesis of [1 a, 2B,3a-2,3-bis(benzyloxymethyl)cyclobutl]imidazol-5-amines: important precursors to cyclobut-A derivatives," J. Chem Society, Perkin Transactions 1: Organic and Bio-Organic Chemistry, vol. 6, pp. 669-675.

Booth et al., 2001, "The Reactions of Diaminomaleonitrile with Isocyanates and Either Aldehydes or Ketones Revisited," J. Org Chem, vol. 66:8436-8441.

Booth, et al., 1994, "Synthesis of 4- and 5-Disubstituted 1-Benzylimidazoles, Important Precursors of Purine Analogs," J. of Heterocyclic of Chemistry, vol. 31(2):345-50.

Bosch et al., "Epidemiology of primary liver cancer," Semin. Liver Dis., 19:271-285 (1999).

Bosch et al., "Primary liver cancer: worldwide incidence and trends," Gastrenterology, 127:S5-S16 (2004).

Brenner et al., "Mechanistic rationale for inhibition of poly(ADP-ribose) polymerase in ETS gene fusion-positive prostate cancer," Cancer Cell, vol. 19, pp. 664-678 (2011).

Brenner et al., "PARP-1 inhibition as a targeted strategy to treat ewing's sarcoma," Cancer Res vol. 2, pp. 1608-1613 (2012).

Brigone et al., "A soluble form of lymphocyte activation gene-3 (IMP321) induces activation of a large range of human effector cytotoxic cells," J. Immunol., 179:4202-4211 (2007).

(56) References Cited

OTHER PUBLICATIONS

Brown et al., (2006) "Morphoproteomic and pharmacoproteomic rationale for mTOR effectors as therapeutic targets in head and neck squamous cell carcinoma," *Annals of Clinical & Laboratory Science* 36.3 (2006): 273-282.
Bruix et al., "Focus on hepatocellular carcinoma," Cancer Cell, 5:215-219 (2004).
Carretero et al., "Integrative Genomic and Proteomic Analyses Identify Targets for Lkb 1-Deficient Metastatic Lung Tumors," Cancer Cell, vol. 17( 6), pp. 547-559 (2010).
Casanova et al., 2007, "Phosphorylated 4E binding protein 1 (p4EBP1) correlates with pathologic grade and prognosis in cervical cancer treated with surgery and radiation therapy," *European J. Cancer Supplements*, 5(4):314, Abstract 5010.
Chang, Sharon B., et al. (2007) "Rapamycin inhibits proliferation of estrogen-receptor-positive breast cancer cells," Journal of Surgical Research 138.1 (2007): 37-44.
Chiarina et al., 2009, "Dual inhibition of class IA phosphatidylinositol 3-kinase and mammalian target of rapamycin as a new therapeutic option for T-cell acute lymphoblastic leukemia," Cancer Res., 69(8):3520-3528.
Chupakhin et al., 2001, "A simple one pot synthesis of condensed 1,2,4-triazines by using the tandem AN-SNipso and SNH_SNipso reactions," J. of Heterocyclic Chemistry, vol. 38(4):901-907.
Cobbold et al., 2009, "Infectious tolerance via the consumption of essential amino acids and mTOR signaling," PNAS, 106(29):12055-12060.
Cohen, "Protein kinase inhibitors for the treatment of disease: the promise and the problems," Handbook of Experimental Pharmacology, Springer Berlin Heidelberg, pp. 1-7, 167 (2005).
Cohen, P. 2001, "The role of protein phosphorylation in human health and disease," Eur. J. Biochem, vol. 268:5001-5010.
Cohen, P. 2002, "Protein kinases—the major drug targets of the twenty-first century?" Nature Reviews/Drug Discovery, vol. 1:309-315.
Coish, et al., 2006, "Small molecule inhibitors of IKK kinase activity," Expert Opin. Ther. Patents, vol. 16(1):1-12.
Costa et al., "Aspects of mTOR biology and the use of mTOR inhibitors in non-Hodgkin's lymphoma," Cancer Treatment Reviews, Saunders, US, vol. 33(1), pp. 78-84 (2007).
Crofts et al., 1997 "Metabolism of 2-amino-1-methyl-6-phenylimidazo[4,5-b]pyridine (PhIP) by human cytochrome P4501B1," Carcinogenesis, vol. 18(9):1793-1798.
Crown et al., "Emerging targeted therapies in triple negative breast cancer," Annals of Oncology, Aug. 6, 2012, vol. 23, pp. vi56-vi65.
Dancey et al., "Ridaforolimus: a promising drug in the treatment of soft-tissue sarcoma and other malignancies," Future Oncology, London, vol. 7, No. 7, Jul. 1, 2011 (Jul. 1, 2011), pp. 827-839.
Dang et al., 1999, "Efficient synthesis of purines and purine nucleosides via an inverse electron demand diels-alder reaction," J. Am Chem Soc., vol. 121(24):5833-5834.
Danoy et al. (2008), Variants in DNA double-strand break repair and DNA damage-response genes and susceptibility to lung and head and neck cancers, *International journal of cancer*, 123.2 (2008): 457-463.
Database Caplus Online Chemical Abstracts Service, Columbus, Ohio, Database Accession No. 1951:49974 (XP-002472261) (1951).
Database Caplus Online Chemical Abstracts Service, Columbus, Ohio, Database Accession No. 1966:26849 (XP-002472263) (1965).
Database Caplus Online Chemical Abstracts Service, Columbus, Ohio, Database Accession No. 1978:433195 (XP-002472262) (1978).
De Oliveria Andrade et al., "Association between hepatitis and hepatocellular carcinoma," J. Glob. Infect. Dis., 1:33-37 (2009).
Dey et al., "Preclinical efficacy of a dual PI3K-mTOR inhibitor, BEZ235 in triple negative breast cancer," European Journal of Cancer, vol. 47, no. Suppl. 4, Oct. 2011 (Oct. 2011), p. 517.
Dornow et al., 1957, "Synthese von2-Oxy-imidazolo-(5',4':2,3)-pyridinen)," Arch Pharm. vol. 290, pp. 20-31 (w/English language abstract).
Dorwald et al., Side Reactions in Organic Synthesis: A Guide to Successful Synthesis Design, Weinheim: Wiley-VCH Verlag GmbH & Co. KGaA, 2005, Preface.
Dowling et al., "Metformin inhibits mammalian target of rapamycin-dependent translation initiation in breast cancer cells," *Cancer res.*, 67(22):10804-10812 (2007).
Dzierba et al., 2004, "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47(23):5783-5790.
Eisenhauer et al., "New response evaluation criteria in solid tumours: revised RECIST guideline (version 1.1)," European J. Cancer, 45:228-247 (2009).
Ellis et al., 2011, "Concurrent HDAC and mTORC1 inhibition attenuate androgen receptor and hypoxia signaling associated with alterations in microRNA expression," PloS one, 2011, e27178, 6.11.
El-Serag et al., "Rising incidence of hepatocellular in the United States," N. Engl. J. Med., 340:745-750 (1999).
El-Serag, "Hepatocellular carcinoma and hepatitis C in the United States," Hepatology, 36(5 Suppl 1):S74-S83 (2002).
EPO Supplementary European Search Report dated Feb. 8, 2013 issued in connection with PCT/US2010/05378.
Fabbro et al., 2002, "Protein kinases as targets for anticancer agents: from inhibitors to useful drugs," Pharmacology & Therapeutics, vol. 93:79-98.
Fagone et al., (2013) "Comparative Study of Rapamycin and Temsirolimus Demonstrates Superimposable Anti Tumour Potency on Prostate Cancer Cells," Basic & clinical pharmacology & toxicology, 112.1 (2013): 63-69.
Farhadi et al., 2006, "The role of protein kinase C isoforms in modulating injury and repair of the intestinal barrier," J. Pharm. Exp. Ther. vol. 316:1-7.
Final Office Action dated Feb. 2, 2010 for U.S. Appl. No. 11/975,652 with Notice of References Cited.
Final Office Action dated May 10, 2011 for U.S. Appl. No. 12/605,791.
Final Office Action dated Nov. 6, 2012 for U.S. Appl. No. 12/910,920 with Notice of Reference Cited.
Final Office Action dated Sep. 30, 2010 for U.S. Appl. No. 11/975,652 with Notice of References Cited.
Fourcade et al., "Upregulation of Tim-3 and PD-1 expression is associated with tumor antigen-specific CD8+ T cell dysfunction in melanoma patients," J. Exp. Med. 207:2175-2186 (2010).
Frandsen et al., 1992, "Reaction of the N2-acetoxy derivative of 2-amino-1-methy 1-6-phenylimidazo[4,5,b] pyridine . . . ," Carcinogenesis, vol. 13(4):629-635.
Freudlsperger et al., 2011, "EGFR-P13K-AKT-MTOR signaling in head and neck squamous cell carcinomas—attractive targets for molecular-oriented therapy," *Expert Opin Ther Targets*, Jan. 1, 2011, vol. 15, No. 1, pp. 63-74.
Frost et al., "AKT activity regulates the ability of mTOR inhibitors to prevent angiogenesis and VEGF expression in multiple myeloma cells," Oncogne, vol. 26(16), pp. 2255-2262 (2007).
Fultz et al., (2008) "mTOR kinase inhibitors exhibit properties that distinguish them from Rapamycin," Cancer Research, May 1, 2008 (68) (9 Supplement) 1490.
Gao et al., "LKB1 in lung cancerigenesis: a serine/threonine kinase as tumor suppressor," Protein & Cell, vol. 2(2), pp. 99-107 (2011).
Gao et al., "LKB1 inhibits lung cancer progression through lysyl oxidase and extracellular matrix remodeling," Proceedings of the National Academy of Sciences, vol. 107(44), pp. 18892-18897 (2010).
Garrido-Castro et al., (2019) "Insights into molecular classifications of triple-negative breast cancer: improving patient selection for treatment," *Cancer discovery*, 9.2 (2019): 176-198.
Gaur et al., "Inhibitors of mTOR overcome drug resistance from topoisomerase II inhibitors in solid tumors," Cancer Lett., 311:20-28 (2011).
Georgakis and Younes, 1978, "From rapa nui to rapamycin:targeting PI3K/Akt/mTOR for cancer therapy," Expert Rev. Anticancer Ther, vol. 6:131-140.
Ghosh PM, et al., Signal transduction pathways in androgen-dependent and -independent prostate cancer cell proliferation, *Endocrine Related Cancer*, 2005, vol. 12, No. 1, pp. 119-134.

(56) References Cited

OTHER PUBLICATIONS

Gini et al., 2013, "The mTOR Kinase Inhibitors, CC214-1 and CC214-2, Preferentially Block the Growth of EGFRvIII-Activated Glioblastomas," Clin Cancer Res 2013;19:5722-5732.
Goodwin et al., "DNA-PKcs-mediated transcriptional regulation drives prostate cancer progression and metastasis," Cancer cell 28.1 (2015):97-113.
Gravina et al., 2011, "The TORC1/TORC2 inhibitor, Palomid 529, reduces tumor growth and sensitizes to docetaxel and cisplatin in aggressive and hormone-refractory prostate cancer cells," Endocrine-related cancer, 2011, 385-400, 18.4.
Grimmiger et al., 2010, "Targeting non-malignant disorders with tyrosine kinase inhibitors," Nat. Rev. Drug Disc., 9(12):956-970.
Gulati et al., "Involvement of mTORC1 and mTORC2 in regulation of glioblastoma multiforme growth and motility," International Journal of Oncology, vol. 35(4):731-740 (2009).
Hackam et al., "Translation of research evidence from animals to humans," JAMA, 296(14):1731-1732 (2006).
Hamad, 2001, "A new synthesis of 4-cyano-1,3-dihydro-2-oxo-2H-imidazole-5-(N 1 -tosyl)carboxamide: Reactive precursor for thiopurine analogues," J of Heterocyclic Chemistry, vol. 38( 4 ):939-944.
Hasan et al., "Hepatitis C-associated hepatocellular carcinoma," Hepatology, 1990, 12:589-591.
Hollenhorst et al., "Oncogenic ETS proteins mimic activated RAS/MAPK signaling in prostate cells," Genes & Development, vol. 25, No. 20, Oct. 15, 2011 (Oct. 15, 2011), pp. 2147-2157.
http://www.sigmaaldrich.com/catalog/product/ALDRICH/678740?lang=en&region=US, last accessed Nov. 1, 2012.
http://www.sigmaaldrich.com/catalog/product/aldrich/697230?lang=en&region=US, last accessed Nov. 1, 2012.
http://www.sigmaaldrich.com/catalog/product/ALDRICH/701602?lang=en&region=US#, last accessed Nov. 1, 2012.
http://www.sigmaaldrich.com/chem is try /chem ical-synth es is/tech nology-spotlights/catalysisapplicationguide.html, last accessed Nov. 1, 2012.
Huang et al., "Genetic and epigenetic silencing of SCARA5 may contribute to human hepatocellular carcinoma by activating FAK signaling," Journal of Clinical Investigation, vol. 120(1), pp. 223-241 (2010).
Inge et al., "Expression of LKB1 tumor suppressor in non-small cell lung cancer determines sensitivity to 2-deoxyglucose," Journal of Thoracic and Cardiovascular Surgery, vol. 137(3), pp. 580-558 (2009).
Irie et al., 2005, "Toward the development of new medicinal leads with selectivity for protein kinase C isozymes," The Chemical Record, vol. 5:185-195.
Ismail-Khan et al., (2010) "A review of triple-negative breast cancer," Cancer Control, 17.3 (2010): 173-176.
Itoh et al., 2004, "A novel practical synthesis of C-2-arylpurines," Advanced Synthesis & Catalysis, vol. 346:1859-1867.
Ji et al., 2007, "LKB1 modulates lung cancer differentiation and metastasis," Nature, 448(7155):807-810.
Jiang et al., "Role of mTOR in anticancer drug resistance," Drug Resistance Updates 11:63-67 (2008).
Johnston, "Are we missing the mTOR target in breast cancer?," Breast Cancer Research and Treatment, Kluwer Academic Publishers, Bolivia, vol. 128, No. 3, Oct. 16, 2010 (Oct. 16, 2010), pp. 607-611.
Jones et al., 1973, "6-Substituted-5-chloro-1,3-dihydro-2H-imidazo(4,5-b)pyrazin-2-ones with hypotensive activity," J. Med. Chem., vol. 16(5):537-542.
Jordan et al., "Tamoxifen: a most unlikely pioneering medicine," Nature Reviews: Drug Discovery, 2003, 2:205-213.
Kalender et al. (2010) "Metformin, Independent of AMPK, Inhibits mTORC1 in a Rag GTPase-Dependent Manner," Cell metabolism, 2010;11(5):390-401. doi:10.1016/j.cmet.2010.03.014.
Kazaoka et al., 2003, "Synthesis of 6-substituted 9-benzyl-8-hydroxypurines with potential interferon-inducing activity," Chemical & Pharmaceutical Bulletin, vol. 51(5):608-611.

Killday et al., 2001, "Microxine, a new cdc2 kinase inhibitor from the Australian marine sponge *Microxina* species," J. of Natural Products, vol. 64(4):525-526.
Kobayashi et al. (2011), Progress of Cancer Chemotherapy B. Each theological cancer treatment (6) Head and neck cancer, Chemotherapy area, 2011, vol. 27 S-1, p. 85-93 (Machine-translated English summary included).
Koike et al., "Molecular basis for the synergy between alcohol and hepatitis C virus in hepatocarcinogenesis," J. Gastroenterol. Hepatol., 23:S87-S91 (2008).
Koike et al., "Molecular basis of hepatitis c virus-associated hepatocarcinogenesis: lessons from animal model studies," J. Gastroenterol. Hepatol., 3:132-135 (2005).
Lau et al., "Abstract 1748: Metformin overcomes cisplatin-resistance in triple negative breast cancer," AARC 102nd Annual Meeting, Orlando, FL (2011).
Lehmann et al., "Identification of human triple-negative breast cancer subtypes and preclinical models for selection of targeted therapies," The Journal of Clinical Investigation, Jul. 2011, vol. 121, No. 7, Jul. 2011 (Jul. 2011), pp. 2750-2767.
Lencioni et al., "Modified RECIST (mRECIST) assessment for hepatocellular carcinoma," Semin. Liver Dis., 30(1):52-60 (2010).
Liaw et al., "Early detection of hepatocellular carcinoma in patients with chronic type B hepatitis," Gastroenterology, 90(2):263-267 (1986).
Liaw, "Prevention and surveillance of hepatitis B virus related hepatocellular carcinoma," Semin. Liver Dis., 25:40-47 (2005).
Liu et al., "Combinatorial Effects of Lapatinib and Rapamycin in Triple-Negative Breast Cancer Cells," Molecular Cancer Therapeutics, vol. 10, No. 8, Aug. 1, 2011 (Aug. 1, 2011), pp. 1460-1469.
Liu et al., "Metformin induces unique biological and molecular responses in triple negative breast cancer cells," Cell Cycle, 8(13):2031-2040 (2009).
Llovet et al., "Sorafenib in advanced hepatocellular carcinoma," N. Engl. J. Med., 359(4):378-390 (2008).
Loo et al., "Development of an Fc-enhanced anti-B7-H3 monoclonal antibody with potent antitumor activity," Clin. Cancer Res., 18(14):3834-3845 (2012).
Macaskill et al., "The mammalian target of rapamycin inhibitor everolimus (RAD001) in early breast cancer: results of a pre-operative study," Breast Cancer Research and Treatment, Kluwer Academic Publishers, Bolivia, vol. 128, No. 3, Oct. 13, 2010 (Oct. 13, 2010), pp. 725-734.
Mahoney et al., 2009, "LKB1/KRAS mutant lung cancers constitute a genetic subset of NSCLC with increased sensitivity to MAPK and mTOR signaling inhibition," Br J Cancer, 100(2):370-375.
Manara et al., "NVP-BEZ235 as a new therapeutic option for sarcomas," Clin. Cancer Res., 16(2):530-540 (2010).
Martins et al., "Insulin-Like Growth Factor I Receptor Pathway Inhibition by ADW742, Alone or in Combination with Imatinib, Doxorubicin, or Vincristine, Is a Novel Therapeutic Approach in Ewing Tumor," Clinical Cancer Research, The American Association for Cancer Research, United States, vol. 12, No. 11, Jun. 1, 2006 (Jun. 1, 2006), pp. 3532-3540.
Mateo-Lozano et al. (2006) "Combined transcriptional and translational targeting of EWS/FLI-1 in Ewing's sarcoma," Clinical Cancer Research 12.22 (2006): 6781-6790.
Mateo-Lozano et al., "Rapamycin induces the fusion-type independent downregulation of the EWS/FLI-1 proteins and inhibits Ewing's sarcoma cell proliferation," Oncogene, Nature Publishing Group, United Kingdom, vol. 22, No. 58, Dec. 18, 2003 (Dec. 18, 2003), pp. 9282-9287.
Minehan et al., 2000, "Molecular recognition of DNA by Hoechst Benzimidazoles: Exploring beyond the opyrrole-imidazole-hydroxypyrrole polyimide-pairing code," Helvitica Chima Acta, vol. 83(9):2197-2213.
Mirkheshti et al. (2016), "Dual targeting of androgen receptor and mTORC1 by salinomycin in prostate cancer," *Oncotarget*, 7.38 (2016): 62240.
Mita et al., "Phase I trial of the novel mammalian target of rapamycin inhibitor deforolimus (AP23573; MK-8669) administered intravenously daily for 5 days every 2 weeks to patients with advanced malignancies," Journal of Clinical Oncology: Official

(56) References Cited

OTHER PUBLICATIONS

Journal of The American Society of Clinical Oncology, vol. 26, No. 3, Jan. 20, 2008 (Jan. 20, 2008), pp. 361-367.
Moradpour et al., "Pathogenesis of hepatocellular carcinoma," Eur. J. Gastro & Hepatol., 17:477-483 (2005).
Morgan T M et al., 2009, "Targeted therapy for advanced prostate cancer: inhibition of the PI3K/Akt/mTOR pathway," NIH Public Access Author Manuscript, Published in Final Edited Form As: Curr Cancer Drug Targets, Mar. 2009, 9(2):237-249, pp. 1-24.
Mortensen et al., "Discovery and SAR exploration of a novel series of imidazo[4,5-] pyrazin-2-ones as potent and selective mTOR kinase inhibitors," Bioorganic & Medicinal Chemistry Letters, Pergamon, Elsevier Science, GB, vol. 21(22), pp. 6793-6799 (2011).
Munster et al., "Phase I trial of a dual TOR kinase and DNA-PK inhibitor (CC-115) in advanced solid and hematologic cancers," *J. Clin. Oncol.*, 34(15):2505-2505 (2016).
Nagashima et al., 2004, "Solution-Phase parallel synthesis of an N-Alkylated dihydropteridinone library from fluorous amino acids," J of Comb. Chemistry, vol. 6(6):942-949.
Nathan et al., "Mammalian target of rapamycin inhibitors as possible adjuvant therapy for microscopic residual disease in head and neck squamous cell cancer," Cancer Res., 67(5):2160-2168 (2007).
Netland et al., "Dactolisib (NVP-BEZ235) toxicity in murine brain tumour models," BMC Cancer, 16:657 (2016).
Nguyen et al., "Hepatitis B-related hepatocellular carcinoma: epidemiological characteristics and disease burden," J. Viral. Hepat., 16(7):453-463 (2009).
Noh et al., (2004), "Determinants of rapamycin sensitivity in breast cancer cells," Clinical Cancer Research, 10.3 (2004): 1013-1023.
Office Action dated Apr. 2, 2012 for U.S. Appl. No. 13/295,513.
Office Action dated Aug. 27, 2012 for U.S. Appl. No. 13/295,513 with Notice of References Cited.
Office Action dated Feb. 28, 2012 for U.S. Appl. No. 12/910,920 with Notice of Reference Cited.
Office Action dated Jan. 19, 2011 for U.S. Appl. No. 12/605,791 with Notice of References Cited.
Office Action dated Jun. 11, 2009 for U.S. Appl. No. 11/975,652.
Office Action dated Jun. 28, 2012 for U.S. Appl. No. 12/910,920 with Notice of Reference Cited.
Office Action dated May 12, 2010 for U.S. Appl. No. 11/975,652.
Office Action dated Nov. 10, 2010 for U.S. Appl. No. 12/605,791.
Office Action dated Sep. 2, 2009 for U.S. Appl. No. 11/975,652.
Oikawa, "ETS Transcription Factors: Possible Targets for Cancer Therapy," Cancer Science, Japanese Cancer Association, Tokyo, Japan, vol. 95, No. 8, Aug. 2004 (Aug. 1, 2004), pp. 626-633.
Pardoll, "The blockade of immune checkpoints in cancer immunotherapy," Nature Rev. Cancer, 12:252-264 (2012).
Park et al., 2000, "A novel mechanism of TRAF signaling revealed by structural and functional analyses of the TRADD-TRAF2 interaction," Cell, vol. 101:777-787.
Parkin et al., "Global cancer statistics," CA Cancer J. Clin., 49:33-64 (1999).
Patani et al., 1998, "Bioisosterim: A rational approach in drug design," Chemical Reviews, vol. 96:3147-3176.
PCT International Search Report dated Dec. 27, 2010 issued in connection with PCT/US2010/053678.
PCT International Search Report dated Feb. 13, 2013 issued in connection with PCT/US2012/067172.
PCT International Search Report dated Jan. 11, 2013 issued in connection with PCT/US2012/049281.
PCT International Search Report dated Mar. 29, 2010 issued in connection with PCT/US2009/062143.
PCT IPRP dated May 10, 2012 issued in connection with PCT/US2010/053678.
PCT IPRP with Written Opinion of the International Searching Authority dated May 12, 2011 in connection with PCT /US2009/062143.
PCT Partial International Search dated Feb. 21, 2013 issued in connection with PCT/US2012/060723.
PCT Partial International Search dated Nov. 15, 2012 issued in connection with PCT/US2012/049281.
PCT Written Opinion dated Dec. 27, 2010 in connection with PCT/US/10/53678.
PCT Written Opinion dated Feb. 13, 2013 issued in connection with PCT/US/2012/067172.
PCT Written Opinion dated Feb. 13, 2013 issued in connection with PCT/US2012/049281.
PCT Written Opinion of the International Searching Authority dated Mar. 29, 2010 issued in connection with PCT/US2009/062143.
Pulukuri et al., 2005, "RNA interference-directed knockdown of urokinase plasminogen activator and urokinase plasminogen activator receptor inhibits prostate cancer cell invasion, survival, and tumorigenicity in vivo," Journal of Biological Chemistry, 2005, 36529-36540, 280.43.
Registry File Document for RN 863501-03-5, 863502-39-0 and others (Sep. 20, 2005).
Ren et al., 2008, "Preparation and application of phosphorylated LKB1 (THr336) polyclonal antibody," Chinese Journal of Biologicals, 21(11):995-998, 1005 (with English language abstract).
Rivera et al., "Pharmacodynamic evaluation of the mTOR inhibitor AP23573 in phase 1 clinical trials," EUR J. Cancer Supplements, 2(8):123 (2004), Abstract 411.
Rustgi, "Epidemiology of hepatocellular carcinoma," Gastroenterol. Clin. North. Am., 16(4):545-551 (1987).
Sakuishi et al., "Targeting Tim-3 and PD-1 pathways to reverse T cell exhaustion and restore anti-tumor immunity," J. Exp. Med., 207:2187-2194 (2010).
Sanchez et al., "Preclinical modeling of combined phosphatidylinositol-3-kinase inhibition with endocrine therapy for estrogen receptor-positive breast cancer," Breast Cancer Research, Current Science, London, United Kingdom, vol. 13, No. 2, Mar. 1, 2011 (Mar. 1, 2011), p. R21.
Saotome, (2007), *Journal of Clinical and Experimental Medicine* (IGAKU NO AYUMI), 2007, vol. 222, No. 13, pp. 1006-1009.
Schayowitz et al., "Prolonging hormone sensitivity in prostate cancer xenografts through dual inhibition of AR and mTOR," Br. J. Cancer, 103:1001-1007 (2010).
Scher et al., Design and end points of clinical trials for patients with progressive prostate cancer and castrate levels of testosterone: recommendations of the Prostate Cancer Clinical Trials Working Group, *Journal of Clinical Oncology*, Mar. 1, 2008, vol. 26, No. 7, pp. 1148-1159, Scher.
Schiewer et al., "mTOR is a selective effector of the radiation therapy response in androgen receptor-positive prostate cancer," Endocrine-Related Cancer, vol. 19, No. 1, Feb. 2012 (Feb. 2012), pp. 1-12.
Seela et al., 2004, "Product Class 17: Purines," Science of Synthesis, vol. 16, pp. 945-1108.
Selvarag et al., (2014) "Prostate cancer ETS rearrangements switch a cell migration gene expression program from RAS/ERK to PI3K/AKT regulation," Molecular cancer 13.1 (2014):61.
Shaw et al., "The LKB1 tumor suppressor negatively regulates mTOR signaling," Cancer Cell, vol. 6(1), pp. 91-99 (2004).
Shaw et al., 2009, "LKB1 and AMP-activated protein kinase control of mTOR signaling and growth," Acta. Physiol (Oxf.) 196(1):65-80.
Shen et al., (2010), "Molecular genetics of prostate cancer: new prospects for old challenges," Genes & Development, 24.18 (2010):1967-2000.
Shoji et al. 2012, "Genotype-dependent efficacy of a dual PI3K/mTOR inhibitor, NVP-BEZ235, and an mTOR inhibitor, RAD001, in endometrial carcinomas." *PloS one* 7.5, 2012, e37431.
Singh et al., 1994, "Novel cAMP PDE III Inhibitors: Imidazo[4,5-b]pyridin-2(3H)-ones and Thiazolo[4,5-b]pyridin-2(3h)-ones and Their Analogs," J. Med. Chem, vol. 37(2):248-254.
Smith et al., "ETS1 transcriptional activity is increased in advanced prostate cancer and promotes the castrate-resistant phenotype," Carcinogenesis, vol. 33, No. 3, Mar. 1, 2012 (Mar. 1, 2012), pp. 572-580.
Squillace et al., "Antitumor Activity of Ridaforolimus and Potential Cell-Cycle Determinants of Sensitivity in Sarcoma and Endometrial Cancer Models," Molecular Cancer Therapeutics, vol. 10, No. 10, Oct. 1, 2011 (Oct. 1, 2011), pp. 1959-1968.

(56) References Cited

OTHER PUBLICATIONS

Sridhar et al., 2000, "Protein Kinases as Therapeutic Targets," Pharm. Research, vol. 17(11):1345-353.
Stebbing et al., "Disease-associated dendritic cells respond to disease-specific antigens through the common heat shock protein receptor," Blood 102(5):1806-1814 (2003).
Subbiah et al., "Targeted Morphoproteomic Profiling of Ewing's Sarcoma Treated with Insulin-Like Growth Factor 1 Receptor (IGF1R) Inhibitors: Response/Resistance Signatures," Plos One, vol. 6, No. 4, Jan. 1, 2011 (Jan. 1, 2011), pp. e18424-e18424.
Takeda et al., 2008, Analysis of relationship between LKB1 gene abnormality in non-small cell lung cancer line and sensitivity to mTOR inhibitor, Japanese Respiratory Society Magazine, 2008, vol. 46, supplement, p. 216, PP532 (English translation included).
Therasse et al., "New guidelines to evaluate the response to treatment in solid tumors," J. National Cancer Institute, 92:205-216 (2000).
Thway, (2009) "Pathology of soft tissue sarcomas," Clinical oncology, 21.9 (2009):695-705.
Toft et al., "Mini review: Basal-Like Breast Cancer: From Molecular Profiles to Targeted Therapies," Molecular Endocrinology, vol. 25, No. 2, Feb. 1, 2011 (Feb. 1, 2011), pp. 199-211.
Torres et al., "Nonalcoholic steatohepatitis and noncirrhotic hepatocellular carcinoma: fertile soil," Semin. Liver Dis., 32(1):30-38 (2012).
Trevisani et al., "Recent advances in the natural history of hepatocellular carcinoma," Carcinogenesis, 29:1299-1305 (2008).
U.S. National Library of Medicine, *ClinicalTrials.gov*, "Everolimus, carboplatin, and paclitaxel in locally advanced head and neck cancer that cannot be removed by surgery (CAPRA)," ClinicalTrials.gov, Identifier NCT01333085 (2011) 8 pages.
Vincenzi et al., "Targeted therapy in sarcomas mammalian target of rapamycin inhibitors from bench to bedside," Expert Opinion on Investigational Drugs, Informa Healthcare, United Kingdom, vol. 20, No. 12, Dec. 1, 2011 (Dec. 1, 2011), pp. 1685-1705.
Vippagunta et al., Advanced Drug Delivery Reviews, 48(18):3-26 (2001).
Wallace 2008, "Palladium-catalyzed synthesis of quinoxaline derivatives," Tetrahedron, vol. 64:9675-9684.
Wander et al. (2011), "Next-generation mTOR inhibitors in clinical oncology: how pathway complexity informs therapeutic strategy," *the Journal of Clinical Investigation*, 121(4), 2011, 1231-1241.
Wang et al., "CCI-779 Inhibits Cell-Cycle G2-M Progression and Invasion of Castration-Resistant Prostate Cancer via Attenuation of UBE2C Transcription and mRNA Stability," Cancer Research, vol. 71. No. 14, Jul. 15, 2011 (Jul. 15, 2011), pp. 4866-4876.
Watanabe et al., "Kokeigan no shinkoukahanteikijun [New criteria for determining effects for solid cancer], revised RECIST guideline (version 1.1)," Japanese Journal of Cancer and Chemotherapy, Dec. 2009, vol. 36, No. 13, pp. 2495 to 2501 (English abstract included).
Wei et al., 2008, "Suppression of Peutz-Jeghers polyposis by targeting mammalian target of rapamycin signaling," Clinical Cancer Research, 2008, 1167-1171, 14.4.
Wei et al., 2009, "Chemopreventive efficacy of rapamycin on Peutz-Jeghers syndrome in a mouse model," Cancer Lett., 277(2):149-154.
Westover et al., 1981, "Synthesis and antiviral activity of certain 9-β-D-Riofuranoaylpurine-6-carboxamides," J. Med. Chem., Vo. 24(8):941-46.
Wingo et al., "Somatic LKB1 Mutations Promote Cervical Cancer Progression," PLOS One, vol. 4(4), pp. 5137-5138 (2009).
Wolff, Manfred E., 1996, Ed. Burger's Medicinal Chemistry and Drug Discovery—Fifth Edition, New York: John Wiley & Sons, 1:975-977.
Yoneda et al., 1976, "A transformationof 7-azapteridines into 6-azapurines (Imidazo[4,5-e]- as - triazines)," Heterocycles, vol. 4(9):1503-1508.
Yoneda et al., 1978, "Synthesis of imadazo[4,5-e]-as-triazine (6-Azapurine) Deriviatives," Chem & Pharm Bulletin, vol. 26(10):3154-3160.
Yu, 2001, "Deregulated PL3K/AKT/TOR pathway in PTEN-deficient tumor cells correlates with an increased growth inhbition sensitivitiy to a A TOR kinase inhbitior CCI-779," Proceedings of the Annual Meeting, Mar. 24, 2001, p. 802, vol. 42, American Association for Cancer Research, US.
Yu, K., et al. (2001) "mTOR, a novel target in breast cancer: the effect of CCI-779, an mTOR inhibitor, in preclinical models of breast cancer," Endocrine-related cancer 8.3 (2001): 249-258.
Yuan et al., "Targeting tumorigenesis: development and use of mTOR inhibitors in cancer therapy," Journal of Hematology & Oncology, vol. 2(1), p. 45 (2009).
Zaki et al., 2007, "The synthesis of imidazol[ 4,5-d]pyridines from a substituted imidazole and acyl or sulfonyl acetonitrile," Tetrahedron, vol. 63(18):3745-3753.
Zenalti et al., Ann. Clin. Lab. Sci., 39(2):160-166 (2009).
Zeng et al., "Treating triple-negative breast cancer by a combination of rapamycin and cyclophosphamide: An in vivo bioluminescence imaging study," European Journal of Cancer, Pergamon Press, Oxford, United Kingdom, vol. 46, No. 6, Apr. 1, 2010 (Apr. 1, 2010), pp. 1132-1143.
Zhao et al., "The effect of mTOR inhibition alone or combined with MEK inhibitors on brain metastasis: an in vivo analysis in triple-negative breast cancer models," Breast Cancer Research and Treatment, Kluwer Academic Publishers, Bolivia, vol. 131, No. 2, Mar. 11, 2011 (Mar. 11, 2011), pp. 425-436.
Zhong et al., 2006, "LKB1 mutation in large cell carcinoma of the lung," Cancer Lung, vol. 53(3):285-294.

|  | Subject Characteristics by HBV Status (ITT) | | | Subject Characteristics by HBV Status (EE) | | |
|---|---|---|---|---|---|---|
|  | HBV+ (n=12) | Non HBV (n=41) | Overall (n=53) | HBV+ (n=11) | Non HBV (n=30) | Overall (n=41) |
| Age, mean (range) years | 57.5 (42 – 77) | 60.8 (25 – 84) | 60.0 (25 – 84) | 55.7 (42 – 67) | 59.1.8 (25 – 77) | 58.2 (25 – 77) |
| Sex, Male (%) : Female (%) | 12 (100%) : 0 (%) | 31 (76%) : 10 (24%) | 43 (81%) : 10 (19%) | 11 (100%) : 0 (0%) | 24 (80%) : 6 (20%) | 35 (85.4%) : 6 (14.6%) |
| Race: |  |  |  |  |  |  |
| Asian | 8 (66.7%) | 2 (4.9%) | 10 (18.9%) | 7 (63.6%) | 1 (3.3%) | 8 (19.5%) |
| Black | 1 (8.3%) | 4 (9.8%) | 5 (9.4%) | 1 (9.1%) | 1 (3.3%) | 2 (4.9%) |
| White | 1 (8.3%) | 30 (73.2%) | 31 (58.5%) | 1 (9.1%) | 23 (76.7%) | 24 (58.5%) |
| Other/Unknown | 2 (16.7%) | 5 (12.2%) | 7 (13.2%) | 2 (18.2%) | 5 (16.7%) | 7 (17.2%) |
| ECOG PS: |  |  |  |  |  |  |
| 0 | 4 (33.3%) | 15 (36.6%) | 19 (35.6%) | 4 (36.4%) | 12 (40%) | 16 (39%) |
| 1 | 8 (66.7%) | 24 (58.5%) | 32 (60.4%) | 7 (63.6%) | 16 (53.3%) | 23 (56.1%) |
| 2 | 0 (0%) | 2 (4.9%) | 2 (3.8%) | 0 (0%) | 2 (6.7%) | 2 (4.9%) |
| Childs-Pugh Score: |  |  |  |  |  |  |
| A (5-6) | 10 (83.3%) | 33 (80.5%) | 43 (81.1%) | 9 (81.8%) | 25 (83.3%) | 34 (82.9%) |
| B ((7-9) | 1 (8.3%) | 3 (7.3%) | 4 (7.5%) | 1 (9.1%) | 2 (6.7%) | 3 (7.3%) |
| Unknown | 1 (8.3%) | 4 (9.8%) | 5 (9.4%) | 1 (9.1%) | 3 (10%) | 3 (7.3%) |
| Cirrhosis, Yes (%) : No (%) | 8 (66.7%) : 4 (33.3%) | 26 (63.4%) : 15 (36.6%) | 34 (64.2%) : 19 (35.8%) | 7 (63.6%) : 4 (36.4%) | 20 (66.7%) : 10 (33.3%) | 27 (65.9%) : 14 (34.1%) |

FIG. 2

|  | Subject Characteristics by HBV Status (ITT) | | | Subject Characteristics by HBV Status (EE) | | |
|---|---|---|---|---|---|---|
|  | HBV+ (n=12) | Non HBV (n=41) | Overall (n=53) | HBV+ (n=11) | Non HBV (n=30) | Overall (n=41) |
| HCC Risk Factor: |  |  |  |  |  |  |
| HBV | 12 (100%) | 0 (0%) | 12 (22.6%) | 11 (100%) | 0 (0%) | 11 (26.8%) |
| HCV | 0 (0%) | 15 (36.6%) | 15 (28.3%) | 0 (0%) | 10 (33.6%) | 10 (24.4%) |
| Alcohol | 0 (0%) | 3 (7.3%) | 3 (5.7%) | 0 (0%) | 3 (10%) | 3 (7.3%) |
| Other/Unknown | 6 (50%) | 23 (56.1%) | 29 (54.7%) | 2 (18.2%) | 17 (56.7%) | 19 (46.3%) |
| APF≥15 ng/mL at baseline, Yes (%) : No (%) | 9 (75%) : 3 (25%) | 27 (65.9%) : 14 (34.1%) | 36 (67.9%) : 17 (32.1%) | 8 (72.7%) : 3 (27.3%) | 21 (70%) : 9 (30%) | 29 (70.7%) : 12 (29.3%) |
| Median CC223 dose (mg/day) (range) | 30.0 (22.8 – 45.0) | 30.0 (19.1 – 45.0) | 30.0 (19.1 – 45.0) | 30.0 (228– 42.5) | 30.0 (19.1 – 45.0) | 30.0 (19.1 – 45.0) |
| Median treatment duration (days) (range) | 112.5 (19.0 – 419.0) | 56.0 (1.0 – 393.0) | 64.0 (1.0 – 419.0) | 113 (48.0 – 419.0) | 70.0 (23.0 – 393.0) | 105.0 (23.0 – 419.0) |
| Median number of cycles (range) | 4 (1 – 15) | 2 (1 – 14) | 3 (1 – 15) | 4 (4 – 15) | 2 (1 – 14) | 3 (1 – 15) |

FIG. 2 continued

Subject Disposition by HBV Status – Part B HCC Cohort
Enrolled Population

| | HBV+ (N=12) n (%) | HBV− (N=41) n (%) | Overall (N=53) n (%) |
|---|---|---|---|
| Subject Disposition | | | |
| Ongoing | 2 (16.7) | 5 (12.2) | 7 (13.2) |
| Discontinued | 10 (83.3) | 36 (87.8) | 46 (86.8) |
| Reason for Discontinuation | | | |
| Adverse event | 3 (25.0) | 11 (26.8) | 14 (26.4) |
| Disease progression | 7 (58.3) | 11 (26.8) | 18 (34.0) |
| Withdrew consent | 0 | 4 (9.8) | 4 (7.5) |
| Death | 0 | 5 (12.2) | 5 (9.4) |
| Lost to follow up | 0 | 2 (4.9) | 2 (3.8) |
| Other | 0 | 3 (7.3) | 3 (5.7) |

FIG. 4

| Efficacy Results | HBV+ | HBV− |
| --- | --- | --- |
| Median overall survival (months) | 12.07 | 5.16 |
| Median overall progression free survival (weeks) | 16 | 15.43 |
| Objective Response Rate | 25% | 0% |
| Disease Control Rate | 91.7% | 43.9% |
| Complete Response | 0 | 0 |
| Partial Response | 3 | 0 |
| Stable disease | 8 | 18 |
| Progressive disease | 1 | 5 |

FIG. 8

TREATMENT OF HEPATOCELLULAR CARCINOMA CHARACTERIZED BY HEPATITIS B VIRUS INFECTION

This application is a U.S. national stage application of International Patent Application No. PCT/US2018/038697, filed Jun. 21, 2018, which claims the benefit of and priority to U.S. Provisional Application No. 62/523,688, filed Jun. 22, 2017, the entire contents of each of which are incorporated herein by reference.

1. FIELD

Provided herein are methods for treating and/or preventing hepatocellular carcinoma (HCC) characterized by hepatitis B virus (HBV) infection in a patient, comprising administering an effective amount of 7-(6-(2-hydroxypropan-2-yl) pyridin-3-yl)-1-((trans)-4-methoxycyclohexyl)-3,4-dihydropyrazino[2,3-b]pyrazin-2(1H)-one or a pharmaceutically acceptable salt or tautomer thereof (collectively referred to herein as "Compound 1") to the patient having HCC characterized by HBV infection. Further provided herein are compounds for use in such methods. Particularly provided herein is 7-(6-(2-hydroxypropan-2-yl) pyridin-3-yl)-1-((trans)-4-methoxycyclohexyl)-3,4-dihydropyrazino[2,3-b]pyrazin-2(1H)-one or a pharmaceutically acceptable salt or tautomer thereof for use in such methods.

2. BACKGROUND

The connection between abnormal protein phosphorylation and the cause or consequence of diseases has been known for over 20 years. Accordingly, protein kinases have become a very important group of drug targets. See Cohen, *Nat. Rev. Drug Disc.*, 2002, 1:309-315, Grimmiger et al., *Nat. Rev. Drug Disc.*, 2010, 9(12):956-970. Various protein kinase inhibitors have been used clinically in the treatment of a wide variety of diseases, such as cancer and chronic inflammatory diseases, including diabetes and stroke. See Cohen, *Eur. J. Biochem.*, 2001, 268:5001-5010, *Protein Kinase Inhibitors for the Treatment of Disease: The Promise and the Problems*, Handbook of Experimental Pharmacology, Springer Berlin Heidelberg, 2005, 167.

The protein kinases belong to a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al., *Pharm. Res.*, 2000, 17(11):1345-1353. Viral infections and the conditions related thereto have also been associated with the regulation of protein kinases. Park et al., *Cell*, 2000, 101(7):777-787.

The protein named mTOR (mammalian target of rapamycin), also called FRAP, RAFT1 or RAPT1), is a 2549-amino acid Ser/Thr protein kinase, that has been shown to be one of the most critical proteins in the mTOR/PI3K/Akt pathway that regulates cell growth and proliferation. Georgakis and Younes, *Expert Rev. Anticancer Ther.*, 2006, 6(1):131-140. mTOR exists within two complexes, mTORC1 and mTORC2. While mTORC1 is sensitive to rapamycin analogs (such as temsirolimus or everolimus), mTORC2 is largely rapamycin-insensitive. Notably, rapamycin is not a TOR kinase inhibitor. Several mTOR inhibitors have been or are being evaluated in clinical trials for the treatment of cancer. Temsirolimus was approved for use in renal cell carcinoma in 2007 and everolimus was approved in 2009 for renal cell carcinoma patients that have progressed on vascular endothelial growth factor receptor inhibitors. In addition, sirolimus was approved in 1999 for the prophylaxis of renal transplant rejection. The interesting but limited clinical success of these mTORC1 inhibitory compounds demonstrates the usefulness of mTOR inhibitors in the treatment of cancer and transplant rejection, and the increased potential for compounds with both mTORC1 and mTORC2 inhibitory activity.

HCC, also known as malignant hepatoma, is the most common primary malignancy of the liver and accounts for 80-90% of primary liver tumors. HCC is one of the most common and devastating malignant diseases worldwide, responsible for more than 1 million deaths annually in the world (Parkin et al., *CA Cancer J. Clin.* 1999, 49:33-64; Bruix et al., *Cancer Cell*, 2004, 5:215-219).

The major risk factors for the development of HCC include hepatitis B or C viral infection, and alcoholic liver disease (Rustgi, *Gastroenterol. Clin. North Am.*, 1987, 16:545-551; Bosch et al., *Semin. Liver Dis.*, 1999, 19:271-285; Bosch et al., *Gastroenterology*, 2004, 127: S5-S16; Moradpour et al., *Eur. J. Gastro & Hepatol.*, 2005, 17:477-483; Koike et al., *J. Gastroenterol. Hepatol.*, 2008, 23: S87-S91; de Oliveria Andrade, J. Glob. Infect. Dis., 2009, 1:33-37). HCC arises most commonly in cirrhotic livers following infection with HBV or hepatitis C virus (HCV) (Liaw, *Semin. Liver Dis.*, 2005, 25:40-47; Koike, *Clin. Gastroenterol. Hepatol.*, 2005, 3:132-135). HCC is associated with HBV infection in about 50% of cases (Liaw, *Semin. Liver Dis.*, 2005, 25:40-47). HCV infection is the cause of 70% of the cases of HCC in Japan (Hasan et al., *Hepatology*, 1990, 12:589-591; El-Serag et al., *N. Engl. J. Med.*, 1999, 340:745-750). The HCC incidence has been increasing in Western countries in recent years due to the spread of HCV infection (El-Serag, *Hepatology*, 2002, 36: S74-83; Trevisani et al., *Carcinogenesis*, 2008, 29:1299-1305) and increasing incidence of non-alcoholic steatosis (Torres et al., *Semin. Liver. Dis.*, 2012, 32(1):30-38).

HCC has poor prognosis with median survival less than 2 years from the date of prognosis. HCC survival rates vary across studies but generally are 10-20% for 5 year survival. HBV-related HCC has extremely poor prognosis with median survival less than 16 months. Survival rates of HBV-related HCC ranged from 36% to 67% after 1 year and from 15% to 26% after 5 year of diagnosis. (Nguyen et al., *J. Viral. Hepat.*, 2009, 16(7):453-463).

Although various chemotherapy regimens are available, traditionally, chemotherapy is not considered an effective treatment option for HCC. Systemic chemotherapy response rates of 10% can be seen, with response rates up to 20% using intra-arterial chemotherapy. Treatment options for subjects with unresectable HCC are severely limited and there remains a high unmet medical need for effective therapies in this disease.

Citation or identification of any reference in Section 2 of this application is not to be construed as an admission that the reference is prior art to the present application.

3. SUMMARY

In one aspect, provided herein is a method for treating and/or preventing HCC characterized by HBV infection in a patient, comprising administering an effective amount of Compound 1 to the patient having HCC characterized by HBV infection. Provided herein is Compound 1 for use in such a method for treating and/or preventing HCC characterized by HBV infection in a patient. In certain embodiments, provided herein is a method for treating HCC characterized by HBV infection in a patient, comprising administering an effective amount of Compound 1 to the patient having HCC characterized by HBV infection. Provided herein is Compound 1 for use in such a method for treating HCC characterized by HBV infection in a patient. In other embodiments, provided herein is a method for preventing HCC characterized by HBV infection in a patient, comprising administering an effective amount of Compound 1 to the patient having HCC characterized by HBV infection. Provided herein is Compound 1 for use in such a method for preventing HCC characterized by HBV infection in a patient.

In certain embodiments, the HCC characterized by HBV infection is unresectable HCC characterized by HBV infection. Thus, in some embodiments, provided herein is a method for treating unresectable HCC characterized by HBV infection in a patient, comprising administering an effective amount of Compound 1 to the patient having HCC characterized by HBV infection. Provided herein is Compound 1 for use in such a method for treating unresectable HCC characterized by HBV infection in a patient. In other embodiments, provided herein is a method for preventing unresectable HCC characterized by HBV infection in a patient, comprising administering an effective amount of Compound 1 to the patient having HCC characterized by HBV infection. Provided herein is Compound 1 for use in such a method for preventing unresectable HCC characterized by HBV infection in a patient.

In another aspect, provided herein is a method for treating and/or preventing HCC characterized by HBV infection in a patient, comprising screening a biological test sample from the patient for HBV infection, and administering an effective amount of Compound 1 to the patient having HCC characterized by HBV infection. Provided herein is Compound 1 for use in such a method for treating and/or preventing HCC characterized by HBV infection in a patient, wherein the method comprises screening a biological test sample from the patient for HBV infection, and administering an effective amount of Compound 1 to the patient having HCC characterized by HBV infection. In certain embodiments, provided herein is a method for treating HCC characterized by HBV infection in a patient, comprising screening a biological test sample from the patient for HBV infection, and administering an effective amount of Compound 1 to the patient having HCC characterized by HBV infection. Provided herein is Compound 1 for use in such a method for treating HCC characterized by HBV infection in a patient, wherein the method comprises screening a biological test sample from the patient for HBV infection, and administering an effective amount of Compound 1 to the patient having HCC characterized by HBV infection. In other embodiments, provided herein is a method for preventing HCC characterized by HBV infection in a patient, comprising screening a biological test sample from the patient for HBV infection, and administering an effective amount of Compound 1 to the patient having HCC characterized by HBV infection. Provided herein is Compound 1 for use in such a method for preventing HCC characterized by HBV infection in a patient, wherein the method comprises screening a biological test sample from the patient for HBV infection, and administering an effective amount of Compound 1 to the patient having HCC characterized by HBV infection.

In certain embodiments, the HCC characterized by HBV infection is unresectable HCC characterized by HBV infection. Thus, in some embodiments, provided herein is a method for treating unresectable HCC characterized by HBV infection in a patient, comprising screening a biological test sample from the patient for HBV infection, and administering an effective amount of Compound 1 to the patient having unresectable HCC characterized by HBV infection. Provided herein is Compound 1 for use in such a method for treating unresectable HCC characterized by HBV infection in a patient, wherein the method comprises screening a biological test sample from the patient for HBV infection, and administering an effective amount of Compound 1 to the patient having unresectable HCC characterized by HBV infection. In yet other embodiments, provided herein is a method for preventing unresectable HCC characterized by HBV infection in a patient, comprising screening a biological test sample from the patient for HBV infection, and administering an effective amount of Compound 1 to the patient having HCC characterized by HBV infection. Provided herein is Compound 1 for use in such a method for preventing unresectable HCC characterized by HBV infection in a patient, wherein the method comprises screening a biological test sample from the patient for HBV infection, and administering an effective amount of Compound 1 to the patient having HCC characterized by HBV infection.

In yet another aspect, provided herein is a method for selecting a patient having HCC for Compound 1 treatment, comprising a) obtaining a biological test sample from the patient; b) analyzing the sample for HBV infection; c) selecting the patient having HCC for Compound 1 treatment if HBV infection is determined in the sample. In certain embodiments, the method further comprises a step d) administering an effective amount of Compound 1 to the patient having HCC characterized by HBV infection. Thus, in some embodiments, provided herein is a method for selecting a patient having HCC for Compound 1 treatment, comprising a) obtaining a biological test sample from the patient; b) analyzing the sample for HBV infection; c) selecting the patient having HCC for Compound 1 treatment if HBV infection is determined in the sample; and d) administering an effective amount of Compound 1 to the patient having HCC characterized by HBV infection. Thus, also provided herein is Compound 1 for use in a method for selecting a patient having HCC for Compound 1 treatment, wherein the method comprises a) obtaining a biological test sample from the patient; b) analyzing the sample for HBV infection; c) selecting the patient having HCC for Compound 1 treatment if HBV infection is determined in the sample; and d) administering an effective amount of Compound 1 to the patient having HCC characterized by HBV infection.

In certain embodiments, the HCC is unresectable HCC. Thus, in some embodiments, provided herein is a method for selecting a patient having unresectable HCC for Compound 1 treatment, comprising a) obtaining a biological test sample from the patient; b) analyzing the sample for HBV infection; c) selecting the patient having unresectable HCC for Compound 1 treatment if HBV infection is determined in the sample. In other embodiments, provided herein is a method for selecting a patient having unresectable HCC for Compound 1 treatment, comprising a) obtaining a biological test sample from the patient; b) analyzing the sample for HBV infection; c) selecting the patient having unresectable HCC for Compound 1 treatment if HBV infection is determined in the sample; and d) administering an effective amount of Compound 1 to the patient having unresectable HCC characterized by HBV infection. Thus, also provided herein is Compound 1 for use in a method for selecting a patient having unresectable HCC for Compound 1 treatment, wherein the method comprises a) obtaining a biological test sample from the patient; b) analyzing the sample for HBV infection; c) selecting the patient having unresectable HCC for Compound 1 treatment if HBV infection is determined in the sample; and d) administering an effective amount of Compound 1 to the patient having unresectable HCC characterized by HBV infection.

In still another aspect, provided herein is a method for predicting response to treatment with Compound 1 in a patient having HCC, the method comprising: a) obtaining a biological test sample from the patient; b) analyzing the sample for HBV infection; c) predicting an increased likelihood of response to the Compound 1 treatment of the patient's HCC if HBV infection is determined in the sample. In certain embodiments, the method further comprises a step d) administering an effective amount of Compound 1 to the patient having HCC characterized by HBV infection. Thus, in some embodiments, provided herein is a method for predicting response to treatment with Compound 1 in a patient having HCC, the method comprising: a) obtaining a biological test sample from the patient; b) analyzing the sample for HBV infection; c) predicting an increased likelihood of response to the Compound 1 treatment of the patient's HCC if HBV infection is determined in the sample; and d) administering an effective amount of Compound 1 to the patient having HCC characterized by HBV infection. Thus, also provided herein is Compound 1 for use in a method for predicting response to treatment with Compound 1 in a patient having HCC, wherein the method comprises: a) obtaining a biological test sample from the patient; b) analyzing the sample for HBV infection; c) predicting an increased likelihood of response to the Compound 1 treatment of the patient's HCC if HBV infection is determined in the sample; and d) administering an effective amount of Compound 1 to the patient having HCC characterized by HBV infection.

In certain embodiments, the HCC is unresectable HCC. Thus, in some embodiments, provided herein is a method for predicting response to treatment with Compound 1 in a patient having unresectable HCC, the method comprising: a) obtaining a biological test sample from the patient; b) analyzing the sample for HBV infection; c) predicting an increased likelihood of response to the Compound 1 treatment of the patient's unresectable HCC if HBV infection is determined in the sample. In other embodiments, provided herein is a method for predicting response to treatment with Compound 1 in a patient having unresectable HCC, the method comprising: a) obtaining a biological test sample from the patient; b) analyzing the sample for HBV infection; c) predicting an increased likelihood of response to the Compound 1 treatment of the patient's unresectable HCC if HBV infection is determined in the sample; and d) administering an effective amount of Compound 1 to the patient having unresectable HCC characterized by HBV infection. Thus, also provided herein is Compound 1 for use in a method for predicting response to treatment with Compound 1 in a patient having unresectable HCC, wherein the method comprises: a) obtaining a biological test sample from the patient; b) analyzing the sample for HBV infection; c) predicting an increased likelihood of response to the Compound 1 treatment of the patient's unresectable HCC if HBV infection is determined in the sample; and d) administering an effective amount of Compound 1 to the patient having unresectable HCC characterized by HBV infection.

In another aspect, provided herein is a method for predicting therapeutic efficacy of Compound 1 in a patient having HCC, the method comprising: a) obtaining a biological test sample from the patient; b) analyzing the sample for HBV infection; c) predicting an increased likelihood of therapeutic efficacy of Compound 1 in the patient's HCC if HBV infection is determined in the sample. In certain embodiments, the method further comprises a step d) administering an effective amount of Compound 1 to the patient having HCC characterized by HBV infection. Thus, in some embodiments, provided herein is a method for predicting therapeutic efficacy of Compound 1 in a patient having HCC, the method comprising: a) obtaining a biological test sample from the patient; b) analyzing the sample for HBV infection; c) predicting an increased likelihood of therapeutic efficacy of Compound 1 in the patient's HCC if HBV infection is determined in the sample; and d) administering an effective amount of Compound 1 to the patient having HCC characterized by HBV infection. Thus, also provided herein is Compound 1 for use in a method for predicting therapeutic efficacy of Compound 1 in a patient having HCC, wherein the method comprises: a) obtaining a biological test sample from the patient; b) analyzing the sample for HBV infection; c) predicting an increased likelihood of therapeutic efficacy of Compound 1 in the patient's HCC if HBV infection is determined in the sample; and d) administering an effective amount of Compound 1 to the patient having HCC characterized by HBV infection.

In certain embodiments, the HCC is unresectable HCC. Thus, in some embodiments, provided herein is a method for predicting therapeutic efficacy of Compound 1 in a patient having unresectable HCC, the method comprising: a) obtaining a biological test sample from the patient; b) analyzing the sample for HBV infection; c) predicting an increased likelihood of therapeutic efficacy of Compound 1 in the patient's unresectable HCC if HBV infection is determined in the sample. In other embodiments, provided herein is a method for predicting therapeutic efficacy of Compound 1 in a patient having unresectable HCC, the method comprising: a) obtaining a biological test sample from the patient; b) analyzing the sample for HBV infection; c) predicting an increased likelihood of therapeutic efficacy of Compound 1 in the patient's unresectable HCC if HBV infection is determined in the sample; and d) administering an effective amount of Compound 1 to the patient having unresectable HCC characterized by HBV infection. Thus, also provided herein is Compound 1 for use in a method for predicting therapeutic efficacy of Compound 1 in a patient having unresectable HCC, wherein the method comprises: a) obtaining a biological test sample from the patient; b) analyzing the sample for HBV infection; c) predicting an increased likelihood of therapeutic efficacy of Compound 1 in the patient's unresectable HCC if HBV infection is determined in the sample; and d) administering an effective amount of Compound 1 to the patient having unresectable HCC characterized by HBV infection.

The present embodiments can be understood more fully by reference to the detailed description and examples, which are intended to exemplify non-limiting embodiments.

4. BRIEF DESCRIPTION OF THE DRAWINGS

FIG. 1 depicts study design for Part B of the clinical study of Example 6.1.

FIG. 2. shows patient characteristics for the Part B HCC cohort.

FIG. 4 shows disposition of HCC treated population (TP) by HBV status.

Figure 5A:
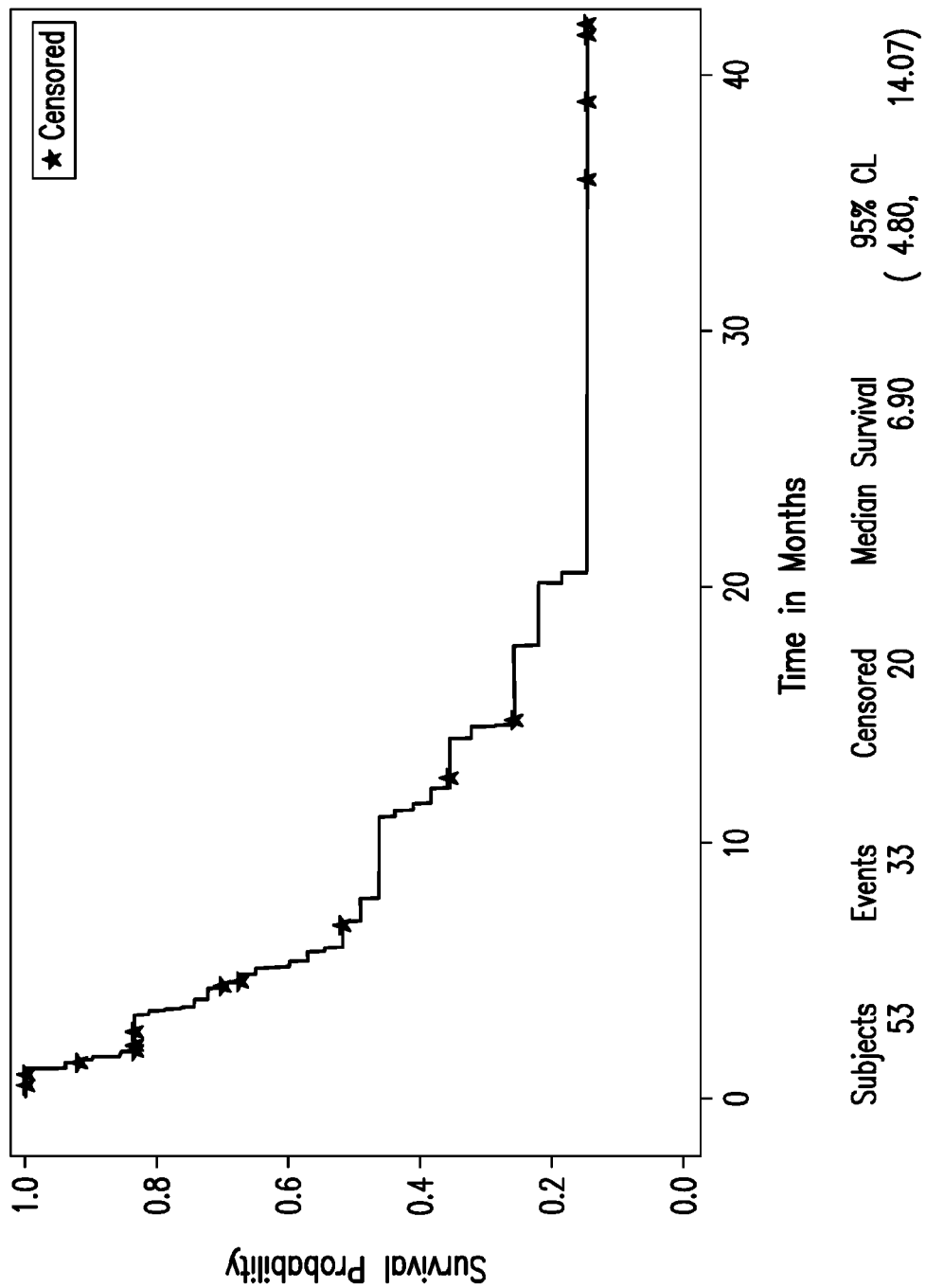
Figure 5B:
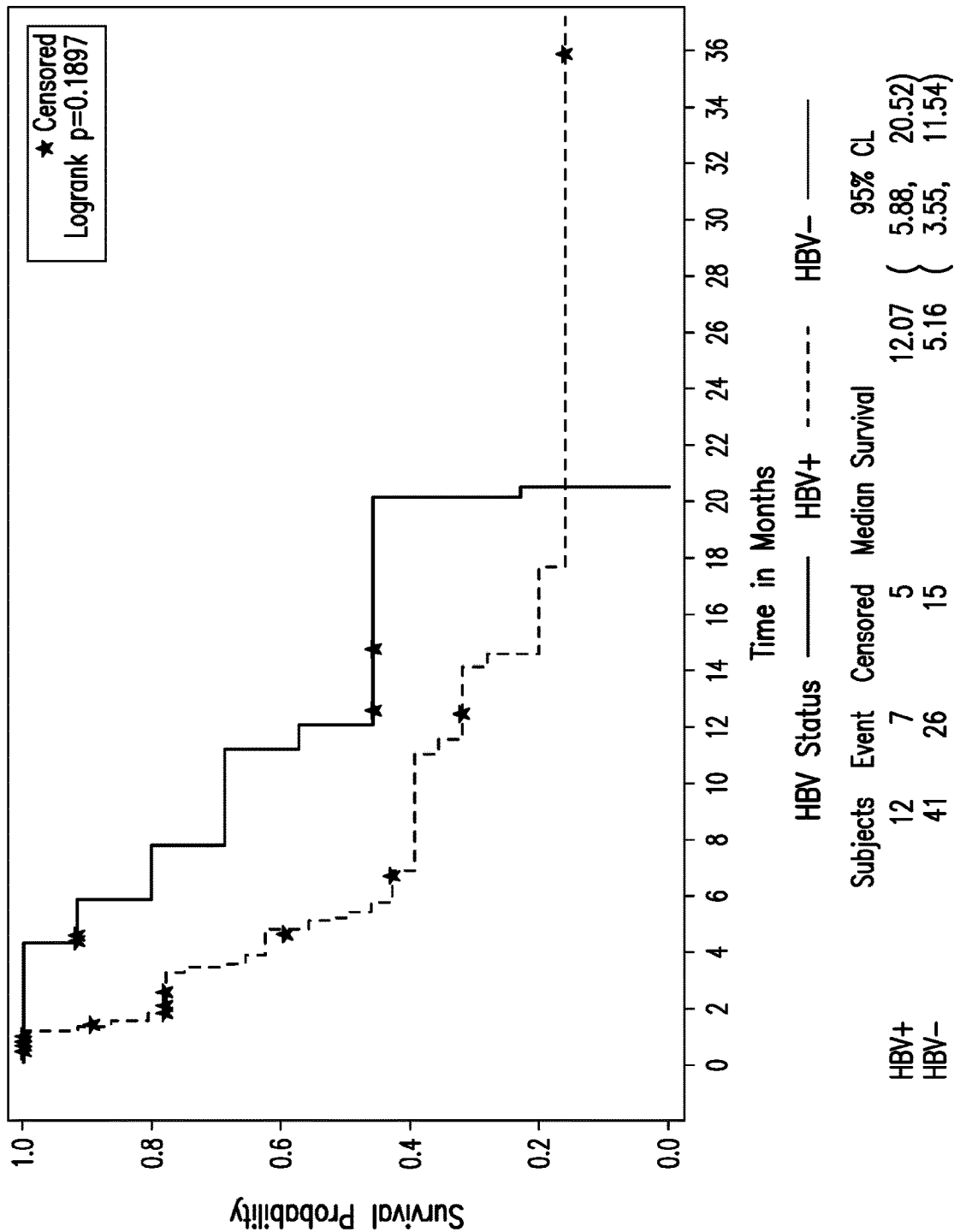

FIGS. 5A and 5B show Kaplan-Meier curve for overall survival (OS) for HCC cohort. FIG. 5A shows OS for all HCC patients without differentiating HBV infected and non-HBV infected patients. FIG. 5B shows OS by HBV status for HCC cohort (p=0.19).

Figure 6A:
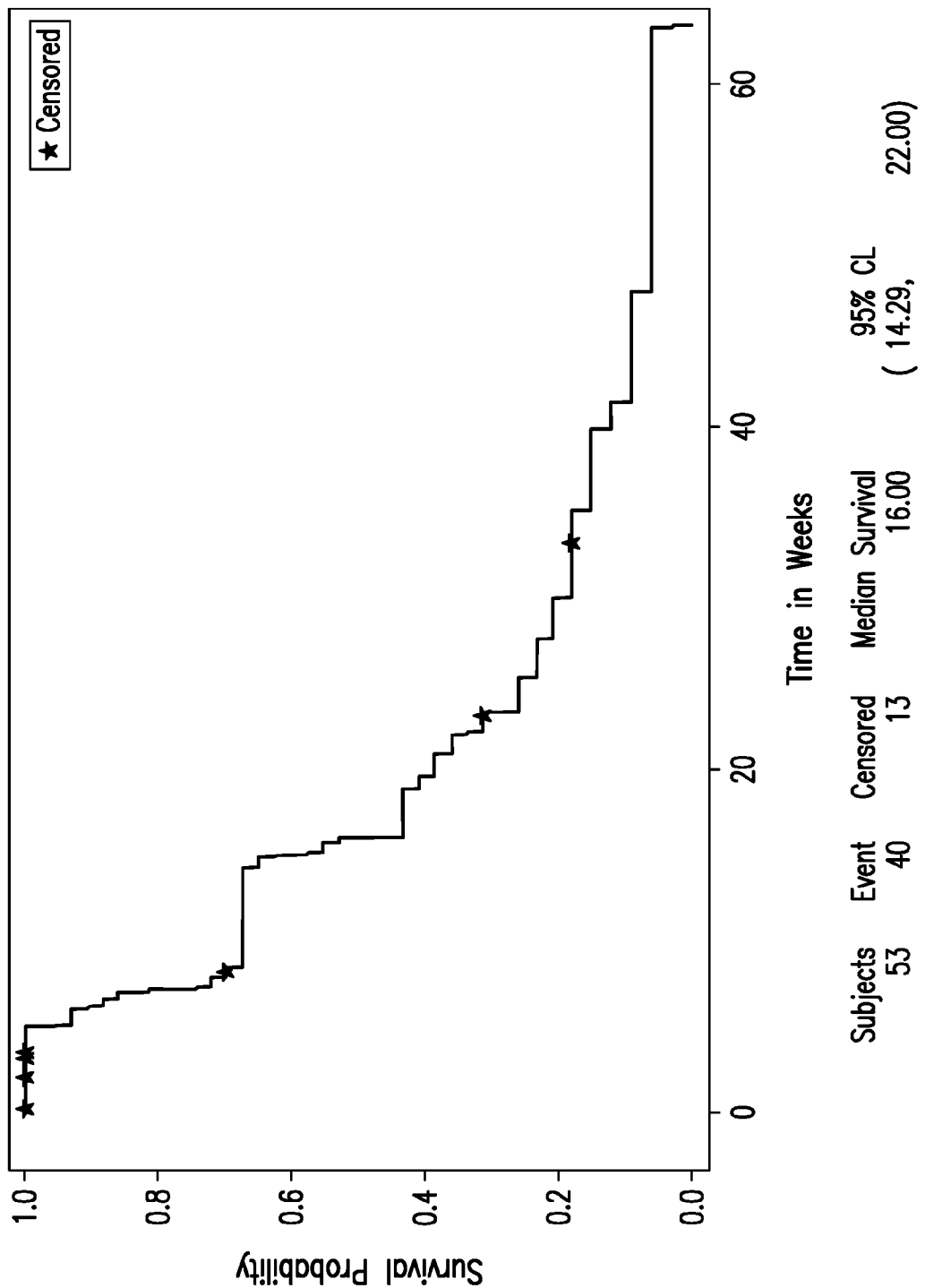
Figure 6B:
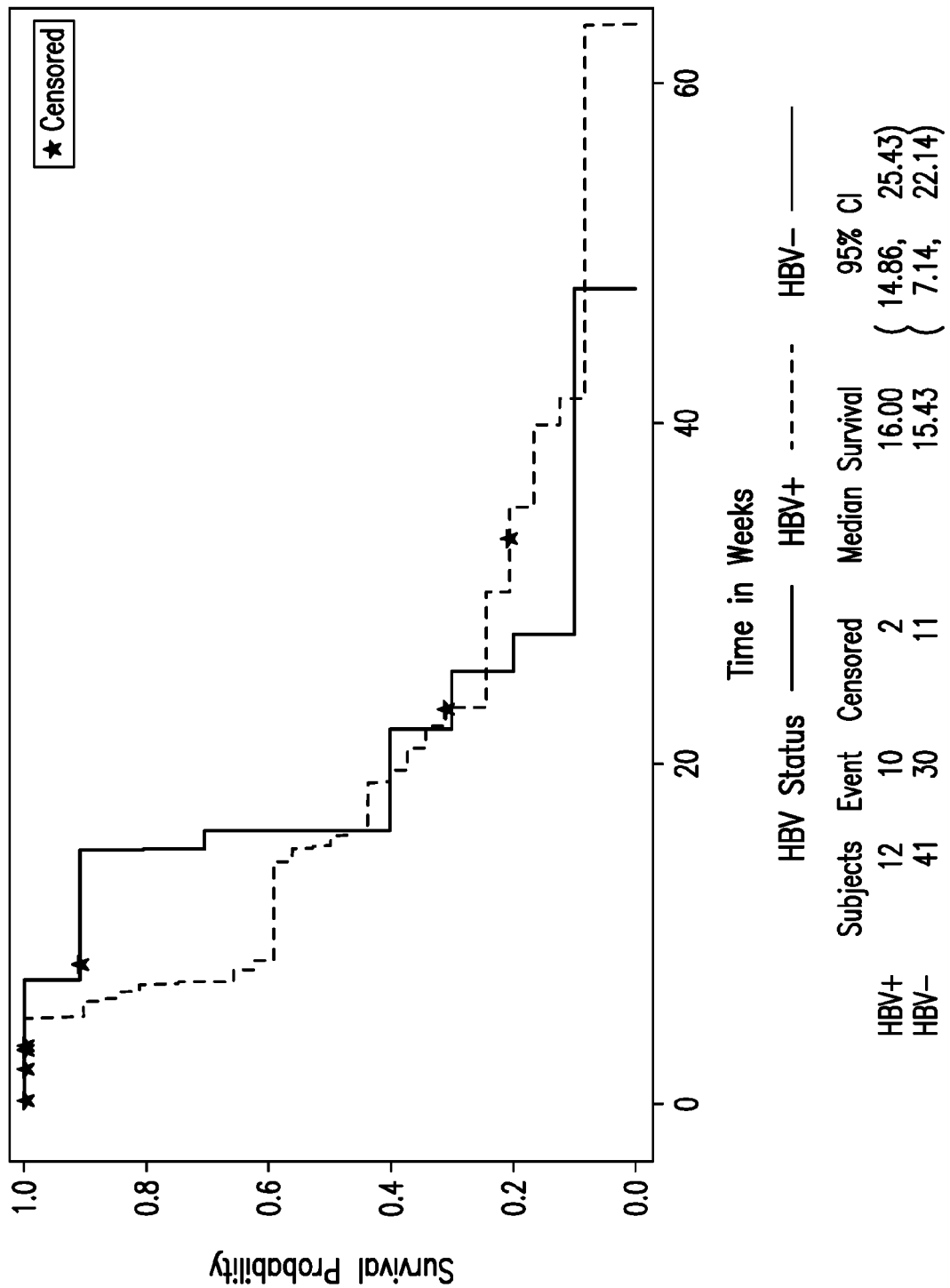

FIGS. 6A and 6B show Kaplan-Meier curve for progression free survival (PFS) for HCC cohort. FIG. 6A shows PFS for all HCC patients without differentiating HBV infected and non-HBV infected patients. FIG. 6B shows PFS by HBV status for HCC cohort.

Figure 7:
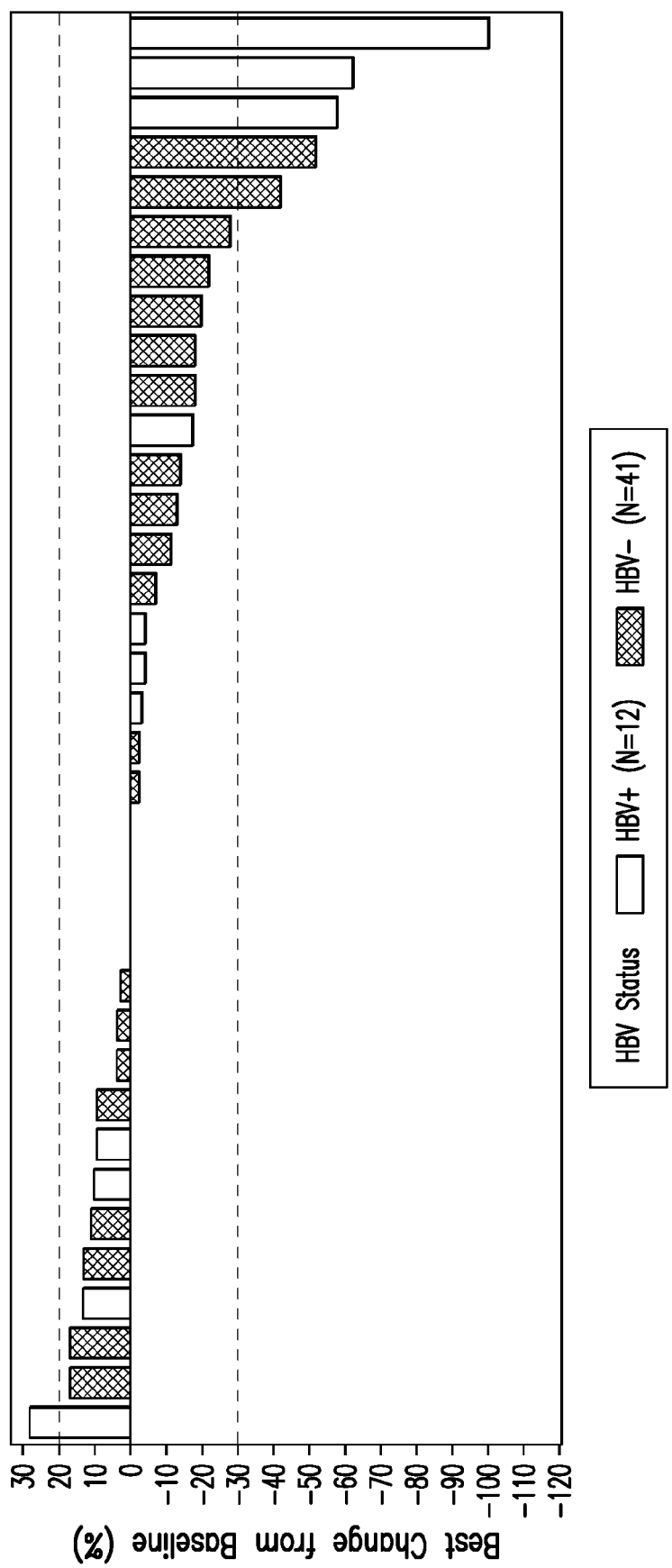

FIG. 7 shows best percentage change from baseline in total length of target lesions in efficacy-evaluable HBV infected versus non-HBV infected patients receiving Compound 1.

FIG. 8 summarizes survival and response data for HBV infected versus non-HBV infected patients receiving Compound 1.

Figure 9:
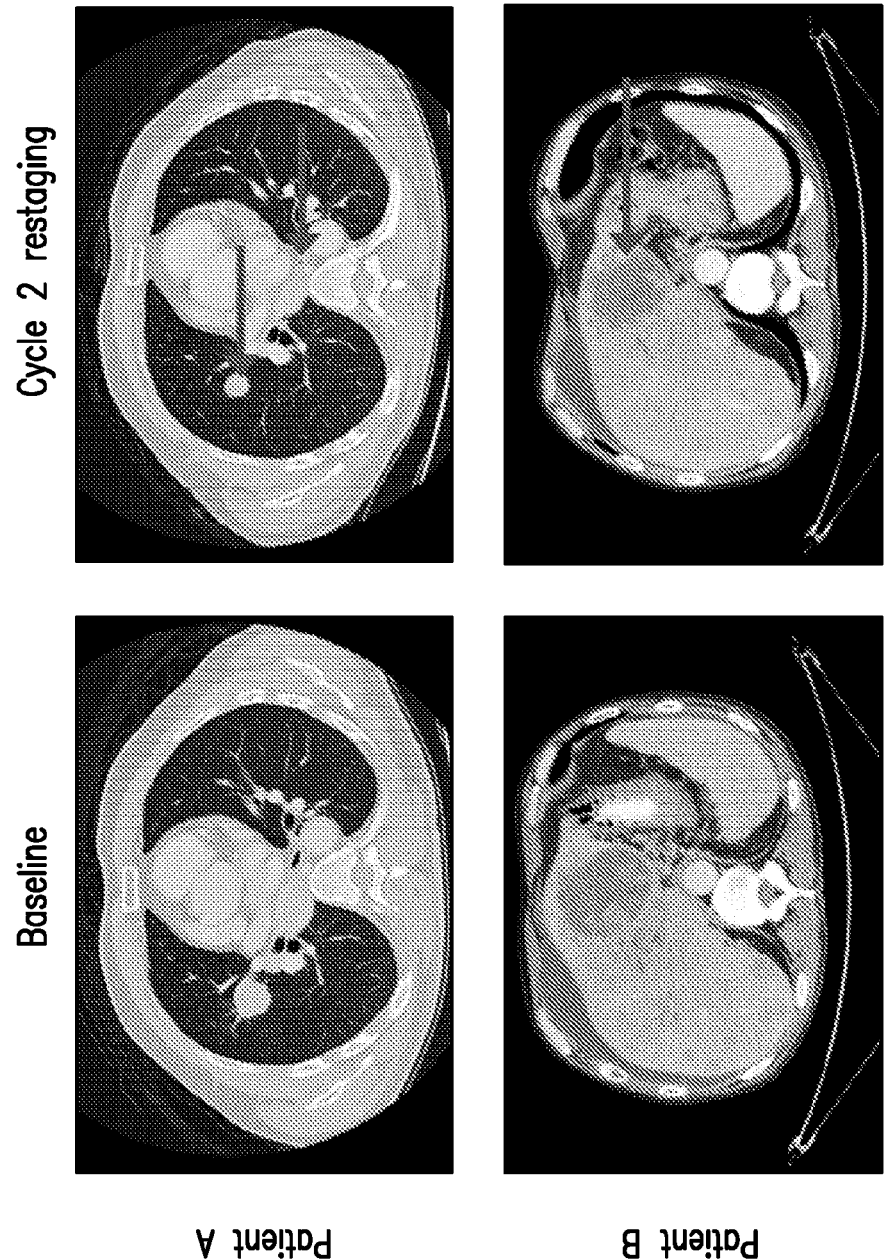

FIG. 9 shows an exemplary radiographic response from two HBV infected HCC patients treated with Compound 1. Patient A shows regression of intrathoracic metastases at the first on-treatment restaging compared to baseline. Patient B shows intrahepatic tumor regression at the first on-treatment restaging compared to baseline.

Figure 10:
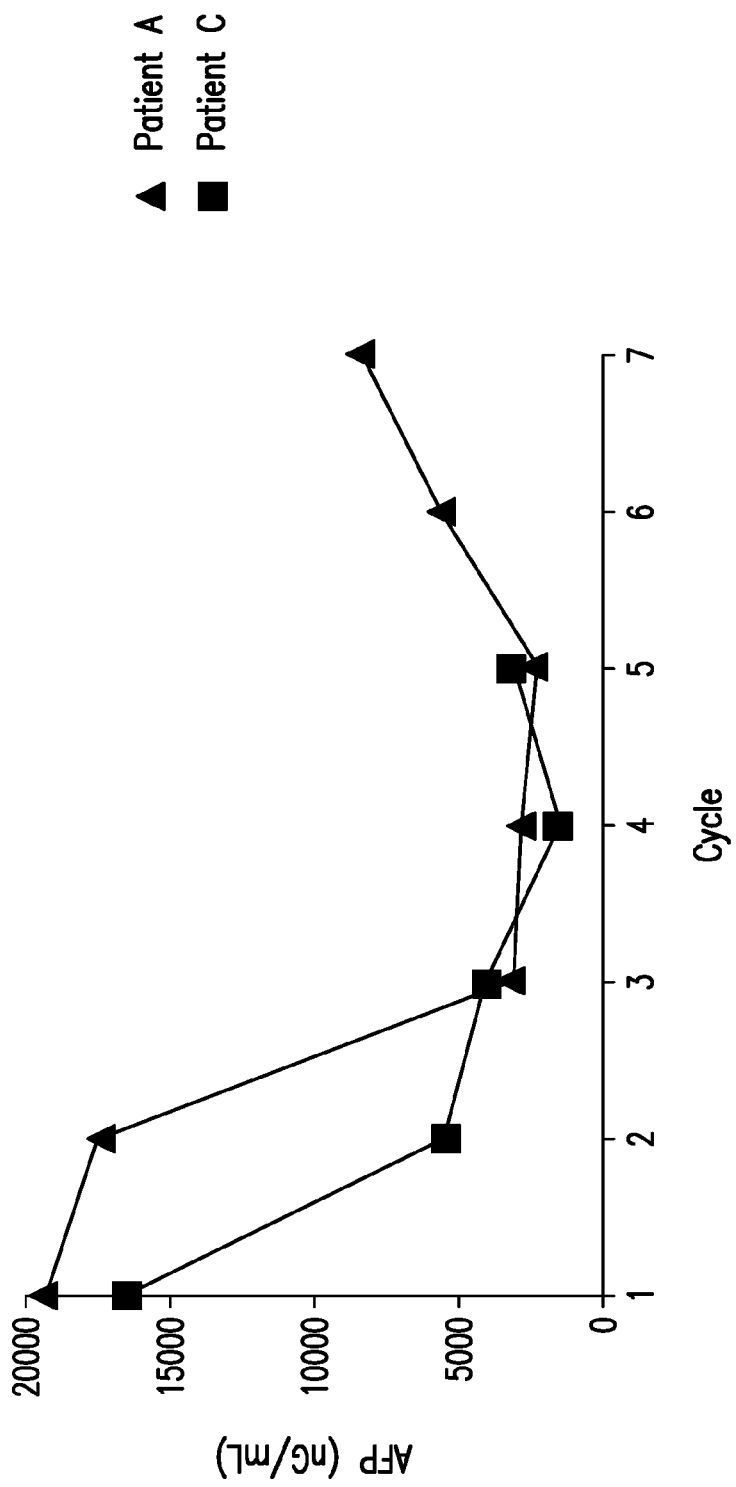

FIG. 10 shows exemplary alpha-fetoprotein (AFP) response in two HCC patients with partial response (PR) receiving Compound 1 treatment. Both patients show early clinically significant, marked reduction of AFP on treatment compared to baseline elevated levels.

5. DETAILED DESCRIPTION

5.1 Definitions

The use of the word "a" or "an" when used in conjunction with the term "comprising" in the claims and/or the specification can mean "one", but it is also consistent with the meaning of "one or more", "at least one" and "one or more than one."

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of Compound 1 include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995).

"Tautomer" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

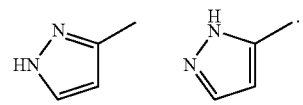

As readily understood by one skilled in the art, a wide variety of functional groups and other structures may exhibit tautomerism and all tautomers of Compound 1 are within the scope of the present invention.

"Treating" as used herein, means an alleviation, in whole or in part, of symptoms associated with a disorder or disease (e.g., HCC characterized by HBV infection), or slowing, or halting of further progression or worsening of those symptoms.

"Preventing" as used herein, means the prevention of the onset, recurrence or spread, in whole or in part, of the disease or disorder (e.g., HCC characterized by HBV infection), or a symptom thereof.

As used herein, "administer" or "administration" refers to the act of physically delivering a substance as it exists outside the body into a patient, such as by oral, mucosal, intradermal, intravenous, intramuscular delivery and/or any other method of physical delivery described herein or known in the art. When a disease, disorder or condition, or a symptom thereof, is being treated, administration of the substance typically occurs after the onset, recurrence or spread of disease, disorder or condition or symptoms thereof. When a disease, disorder or condition, or symptoms thereof, are being prevented, administration of the substance typically occurs before the onset, recurrence or spread of the disease, disorder or condition or symptoms thereof.

The term "effective amount" in connection with Compound 1 means an amount alone or in combination capable of alleviating, in whole or in part, a symptom associated with HCC, or slowing or halting further progression or worsening of those symptoms, or treating or preventing HCC in a subject having or at risk for having HCC. The effective amount of Compound 1, for example in a pharmaceutical composition, may be at a level that will exercise the desired effect; for example, about 0.005 mg/kg of a subject's body weight to about 10 mg/kg of a patient's body weight in unit dosage for both oral and parenteral administration.

As used herein, the term "combination" or administration "in combination" includes administration as a mixture, simultaneous administration using separate formulations, and consecutive administration in any order.

"Consecutive" means that a specific time has passed between the administration of the active agents. For example, "consecutive" may be that more than 10 minutes have passed between the administration of the separate active agents. The time period can then be more than 10 min, more than 30 minutes, more than 1 hour, more than 3 hours, more than 6 hours or more than 12 hours.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Non-limiting examples of checkpoint inhibitors include CTLA-4, CD80, CD86, PD-1, PD-L1, and PD-L2 (Pardoll, *Nature Rev. Cancer*, 2012, 12:252-264).

The terms "patient" and "subject" as used herein include an animal, including, but not limited to, an animal such as a cow, monkey, horse, sheep, pig, chicken, turkey, quail, cat, dog, mouse, rat, rabbit or guinea pig, in one embodiment a mammal, in another embodiment a human.

As used herein, the term "treated population" or "TP" refers to all enrolled subjects who took at least 1 dose of Compound 1. Drug exposure and all safety analyses are based on the treated population.

As used herein, the term "efficacy evaluable population" or "EE population" refers to all subjects who met eligibility criteria, completed at least 1 cycle of Compound 1 treatment, and had baseline and at least 1 postbaseline efficacy assessment. Efficacy assessment means radiological or clinical assessment of given type of tumor, or tumor assessment by other appropriate means described by relevant tumor response criteria. Specifically, efficacy assessment may include valid radiologic tumor assessment for subjects with HCC. In addition, subjects are to take at least 70% of assigned days of Compound 1 during Cycle 1 or have Cycle 2 dosing records to be defined as having completed at least 1 treatment cycle.

As used herein, the term "biological test sample" refers to a sample taken from serum, plasma, blood, dried blood/ plasma spots, hepatocytes, primary tumor, or sites of metastasis of HCC, including but not limited to, lungs, lymph nodes, adrenal glands, bones, peritoneum, portal vein, brain, saliva, parotid tissue, etc.

The term "HBV positive" or "HBV infected," used interchangeably herein, refers to the HBV status of HCC patients, which is determined by an algorithm to identify subjects with HCC considered to have been infected with HBV. Variables useable for the algorithm include but are not limited to the following: medical history of HBV, immunization history, prior or current treatment for HBV, cirrhosis attributed to HBV, serological testing for HBV antigens and/or antibodies, HBV load, and the presence of HBV DNA. Non-limiting examples of such variables are the presence of HBV surface antigen (HBsAg), the presence of antibody to HBV surface antigen (anti-HBsAg), the presence of HBV core antigen (HBcAg), the presence of antibody to HBV core antigen (anti-HBcAg), the presence of HBV envelope protein antigen (HBeAg), the presence of antibody to HBV envelope protein antigen (anti-HBeAg), the presence of HBV x-protein antigen (HBxAg), the presence of antibody to HBV x-protein antigen (HBxAg), the presence of HBV core-related antigen (HBcrAg), the presence of antibody to HBV core-related antigen (anti-HBcrAg), HBV viral load, use of anti HBV medications, the presence of HBV DNA, the presence of HBV mRNA, and the presence of HBV protein. Similarly, the term "HBV negative" or "non-HBV infected," used interchangeably herein, refers to the HBV status of HCC patients, who are considered to have neither HBV infection nor a history of it.

As used herein, the term "hepatocellular carcinoma (HCC) characterized by hepatitis B virus (HBV) infection" is defined to be interchangeable with the terms "HCC associated with HBV infection," "HCC related to HBV infection," "HCC with a history of HBV infection," "HBV positive HCC," "HBV associated HCC," "HBV related HCC," or "HBV infected HCC."

The term "likelihood" generally refers to an increase in the probability of an event. The term "likelihood" when used in reference to the effectiveness of a cancer patient response generally contemplates an increased probability that a cancer or tumor syndrome, or symptom thereof, will be lessened or decreased.

The term "predict" generally means to determine or tell in advance. When used to "predict" the effectiveness of a cancer treatment, for example, the term "predict" can mean that the likelihood of the outcome of the treatment can be determined at the outset, before the treatment has begun, or before the treatment period has progressed substantially.

The terms "determining", "measuring", "evaluating", "assessing," and "assaying" as used herein generally refer to any form of measurement, and include determining whether an element is present or not. These terms include both quantitative and/or qualitative determinations.

In the context of HCC, inhibition may be assessed by inhibition of disease progression, inhibition of tumor growth, reduction of primary tumor, relief of tumor-related symptoms, inhibition of tumor secreted factors (such as, for example, AFP), delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from randomization (for example, first dose date) until death from any cause, and is measured in the intent-to-treat population. TTP as used herein means the time from randomization (for example, first dose date) until objective tumor progression; TTP does not include deaths. As used herein, PFS means the time from randomization (for example, first dose date) until objective tumor progression or death. In one embodiment, PFS rates are computed using the Kaplan-Meier estimates.

In one embodiment, the survival rate is defined as the Kaplan-Meier estimated proportion of subjects surviving at 6, 9, 12 months. As used herein, Disease control rate (DCR) means the percentage of subjects with complete (CR), or partial response (PR) or stable disease (SD). As used herein, Time To Response (TTR) means the time from randomization (for example, first dose date) to the first documentation of response of PR or better. As used herein, Duration of response (DOR) means the time from the time when criteria are first met for CR/PR (whichever is first recorded) until the first date that recurrent or progressive disease is objectively documented.

In certain embodiments, the treatment of HCC may be assessed by Response Evaluation Criteria in Solid Tumors (RECIST 1.1) (see Thereasse et al., *J. National Cancer Institute*, 2000, 92:205-216 and Eisenhauer et al., *European J. Cancer*, 2009, 45:228-247). Overall responses for all possible combinations of tumor responses in target and non-target lesions with or without the appearance of new lesions are as follows:

| Target lesions | Non-target lesions | New lesions | Overall response |
|---|---|---|---|
| CR | CR | No | CR |
| CR | Incomplete response/SD | No | PR |
| PR | Non-PD | No | PR |
| SD | Non-PD | No | SD |
| PD | Any | Yes or no | PD |
| Any | PD | Yes or no | PD |
| Any | Any | Yes | PD |

CR = complete response;
PR = partial response;
SD = stable disease; and
PD = progressive disease.

With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions, and stable disease (SD) is neither sufficient shrinkage to qualify for partial response nor sufficient increase to qualify for progressive disease, taking as reference the smallest sum longest diameter since the treatment started.

With respect to the evaluation of non-target lesions, CR is the disappearance of all non-target lesions and normalization of tumor marker level, incomplete response/SD is the persistence of one or more non-target lesion(s) and/or the maintenance of tumor marker level above the normal limits, and PD is the appearance of one or more new lesions and/or unequivocal progression of existing non-target lesions.

In some embodiments, the treatment of HCC may also be assessed by modified Response Evaluation Criteria in Solid Tumors (mRECIST for HCC) (see Lencioni et al. *Semin Liver Dis*. 2010 February; 30(1):52-60.

5.2 Compound 1

Provided herein are uses for the compound having the structure:

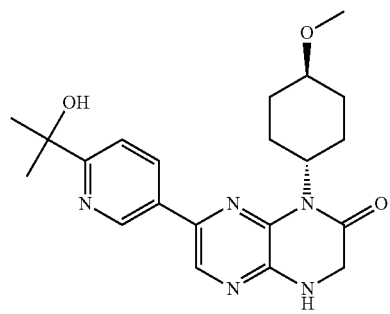

and having the name 7-(6-(2-hydroxypropan-2-yl)pyridin-3-yl)-1-((trans)-4-methoxycyclohexyl)-3,4-dihydropyrazino[2,3-b]pyrazin-2(1H)-one, including pharmaceutically acceptable salts or tautomers thereof (collectively referred to herein as "Compound 1").

Compound 1 can be prepared using reagents and methods known in the art, including the methods provided in U.S. Pat. No. 8,110,578, issued on Feb. 7, 2012; U.S. Pat. No. 8,569,494, issued on Oct. 29, 2013; and U.S. Pat. No. 9,359,364, issued on Jun. 7, 2016, the entire contents of each of which are incorporated herein by reference.

As used herein "metabolite M1" refers to the compound having the structure

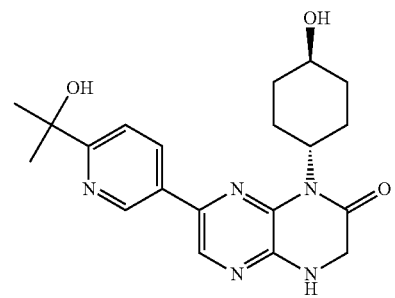 [SMILES: CC(C)(O)c1ccc(-c2cnc3c(n2)N([C@H]2CC[C@H](O)CC2)C(=O)CN3)cn1]

and having the name 1-((trans)-4-hydroxycyclohexyl)-7-(6-(2-hydroxypropan-2-yl)pyridin-3-yl)-3,4-dihydropyrazino[2,3-b]-pyrazin-2(1H)-one, or tautomers thereof.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.3 Methods of Use and Compound 1 for Use in Such Methods

Compound 1 as provided herein can be used in all methods provided herein. In one aspect, provided herein is a method for treating and/or preventing HCC characterized by HBV infection in a patient, comprising administering an effective amount of Compound 1 to the patient having HCC characterized by HBV infection. Provided herein is Compound 1 for use in such a method for treating and/or preventing HCC characterized by HBV infection in a patient. In certain embodiments, provided herein is a method for treating HCC characterized by HBV infection in a patient, comprising administering an effective amount of Compound 1 to the patient having HCC characterized by HBV infection. Provided herein is Compound 1 for use in such a method for treating HCC characterized by HBV infection in a patient. In other embodiments, provided herein is a method for preventing HCC characterized by HBV infection in a patient, comprising administering an effective amount of Compound 1 to the patient having HCC characterized by HBV infection. Provided herein is Compound 1 for use in such a method for preventing HCC characterized by HBV infection in a patient, comprising administering an effective amount of Compound 1 to the patient having HCC characterized by HBV infection. In certain embodiments, the HCC characterized by HBV infection is unresectable HCC characterized by HBV infection. Thus, in some embodiments, provided herein is a method for treating unresectable HCC characterized by HBV infection in a patient, comprising administering an effective amount of Compound 1 to the patient having unresectable HCC characterized by HBV infection. Provided herein is Compound 1 for use in such a method for treating unresectable HCC characterized by HBV infection in a patient. In other embodiments, provided herein is a method for preventing unresectable HCC characterized by HBV infection in a patient, comprising administering an effective amount of Compound 1 to the patient having unresectable HCC characterized by HBV infection. Provided herein is Compound 1 for use in such a method for preventing unresectable HCC characterized by HBV infection in a patient.

In some embodiments, provided herein is a method for treating and/or preventing HCC associated with HBV infection in a patient, comprising administering an effective amount of Compound 1 to the patient having HCC associated with HBV infection. Provided herein is Compound 1 for use in such a method for treating and/or preventing HCC associated with HBV infection in a patient. In certain embodiments, provided herein is a method for treating HCC associated with HBV infection in a patient, comprising administering an effective amount of Compound 1 to the patient having HCC associated with HBV infection. Provided herein is Compound 1 for use in such a method for treating HCC associated with HBV infection in a patient. In other embodiments, provided herein is a method for preventing HCC associated with HBV infection in a patient, comprising administering an effective amount of Compound 1 to the patient having HCC associated with HBV infection. Provided herein is Compound 1 for use in such a method for preventing HCC associated with HBV infection in a patient. In one embodiment, the HCC associated with HBV infection is unresectable HCC associated with HBV infection.

In some embodiments, provided herein is a method for treating and/or preventing HCC related to HBV infection in a patient, comprising administering an effective amount of Compound 1 to the patient having HCC related to HBV infection. Provided herein is Compound 1 for use in such a method for treating and/or preventing HCC related to HBV infection in a patient. In certain embodiments, provided herein is a method for treating HCC related to HBV infection in a patient, comprising administering an effective amount of Compound 1 to the patient having HCC related to HBV infection. Provided herein is Compound 1 for use in such a method for treating HCC related to HBV infection in a patient. In other embodiments, provided herein is a method for preventing HCC related to HBV infection in a patient, comprising administering an effective amount of Compound 1 to the patient having HCC related to HBV infection. Provided herein is Compound 1 for use in such a method for preventing HCC related to HBV infection in a patient. In one embodiment, the HCC related to HBV infection is unresectable HCC related to HBV infection.

In some embodiments, provided herein is a method for treating and/or preventing HCC with a history of HBV infection in a patient, comprising administering an effective amount of Compound 1 to the patient having HCC with a history of HBV infection. Provided herein is Compound 1 for use in such a method for treating and/or preventing HCC with a history of HBV infection in a patient. In certain embodiments, provided herein is a method for treating HCC with a history of HBV infection in a patient, comprising administering an effective amount of Compound 1 to the patient having HCC with a history of HBV infection. Provided herein is Compound 1 for use in such a method for treating HCC with a history of HBV infection in a patient. In other embodiments, provided herein is a method for preventing HCC with a history of HBV infection in a patient, comprising administering an effective amount of Compound 1 to the patient having HCC with a history of HBV infection. Provided herein is Compound 1 for use in such a method for preventing HCC with a history of HBV infection in a patient. In one embodiment, the HCC with a history of HBV infection is unresectable HCC with a history of HBV infection.

In some embodiments, provided herein is a method for treating and/or preventing HBV positive HCC in a patient, comprising administering an effective amount of Compound 1 to the patient having HBV positive HCC. Provided herein is Compound 1 for use in such a method for treating and/or preventing HBV positive HCC in a patient. In certain embodiments, provided herein is a method for treating HBV positive HCC in a patient, comprising administering an effective amount of Compound 1 to the patient having HBV positive HCC. Provided herein is Compound 1 for use in such a method for treating HBV positive HCC in a patient. In other embodiments, provided herein is a method for preventing HBV positive HCC in a patient, comprising administering an effective amount of Compound 1 to the patient having HBV positive HCC. Provided herein is Compound 1 for use in such a method for preventing HBV positive HCC in a patient. In one embodiment, the HBV positive HCC is unresectable HBV positive HCC.

In some embodiments, provided herein is a method for treating and/or preventing HBV associated HCC in a patient, comprising administering an effective amount of Compound 1 to the patient having HBV associated HCC. Provided herein is Compound 1 for use in such a method for treating and/or preventing HBV associated HCC in a patient. In certain embodiments, provided herein is a method for treating HBV associated HCC in a patient, comprising administering an effective amount of Compound 1 to the patient having HBV associated HCC. Provided herein is Compound 1 for use in such a method for treating HBV associated HCC in a patient. In other embodiments, provided herein is a method for preventing HBV associated HCC in a patient, comprising administering an effective amount of Compound 1 to the patient having HBV associated HCC. Provided herein is Compound 1 for use in such a method for reventing HBV associated HCC in a patient. In one embodiment, the HBV associated HCC is unresectable HBV associated HCC.

In some embodiments, provided herein is a method for treating and/or preventing HBV related HCC in a patient, comprising administering an effective amount of Compound 1 to the patient having HBV related HCC. Provided herein is Compound 1 for use in such a method for treating and/or preventing HBV related HCC in a patient. In certain embodiments, provided herein is a method for treating HBV related HCC in a patient, comprising administering an effective amount of Compound 1 to the patient having HBV related HCC. Provided herein is Compound 1 for use in such a method for treating HBV related HCC in a patient. In other embodiments, provided herein is a method for preventing HBV related HCC in a patient, comprising administering an effective amount of Compound 1 to the patient having HBV related HCC. Provided herein is Compound 1 for use in such a method for preventing HBV related HCC in a patient. In one embodiment, the HBV related HCC is unresectable HBV related HCC.

In some embodiments, provided herein is a method for treating and/or preventing HBV infected HCC in a patient, comprising administering an effective amount of Compound 1 to the patient having HBV infected HCC. Provided herein is Compound 1 for use in such a method for treating and/or preventing HBV infected HCC in a patient. In certain embodiments, provided herein is a method for treating HBV infected HCC in a patient, comprising administering an effective amount of Compound 1 to the patient having HBV infected HCC. Provided herein is Compound 1 for use in such a method for treating HBV infected HCC in a patient In other embodiments, provided herein is a method for preventing HBV infected HCC in a patient, comprising administering an effective amount of Compound 1 to the patient having HBV infected HCC. Provided herein is Compound 1 for use in such a method for preventing HBV infected HCC in a patient. In one embodiment, the HBV infected HCC is unresectable HBV infected HCC.

In another aspect, provided herein is a method for treating and/or preventing HCC characterized by HBV infection in a patient, comprising screening a biological test sample from the patient for HBV infection, and administering an effective amount of Compound 1 to the patient having HCC characterized by HBV infection. Provided herein is Compound 1 for use in such a method for treating and/or preventing HCC characterized by HBV infection in a patient, wherein the method comprises screening a biological test sample from the patient for HBV infection, and administering an effective amount of Compound 1 to the patient having HCC characterized by HBV infection. In certain embodiments, provided herein is a method for treating HCC characterized by HBV infection in a patient, comprising screening a biological test sample from the patient for HBV infection, and administering an effective amount of Compound 1 to the patient having HCC characterized by HBV infection. Provided herein is Compound 1 for use in such a method for treating HCC characterized by HBV infection in a patient, wherein the method comprises screening a biological test sample from the patient for HBV infection, and administering an effective amount of Compound 1 to the patient having HCC characterized by HBV infection. In other embodiments, provided herein is a method for preventing HCC characterized by HBV infection in a patient, comprising screening a biological test sample from the patient for HBV infection, and administering an effective amount of Compound 1 to the patient having HCC characterized by HBV infection. Provided herein is Compound 1 for use in such a method for preventing HCC characterized by HBV infection in a patient, wherein the method comprises screening a biological test sample from the patient for HBV infection, and administering an effective amount of Compound 1 to the patient having HCC characterized by HBV infection.

In certain embodiments, the HCC characterized by HBV infection is unresectable HCC characterized by HBV infection. Thus, in some embodiments, provided herein is a method for treating unresectable HCC characterized by HBV infection in a patient, comprising screening a biological test sample from the patient for HBV infection, and administering an effective amount of Compound 1 to the patient having unresectable HCC characterized by HBV infection. Provided herein is Compound 1 for use in such a method for treating unresectable HCC characterized by HBV infection in a patient, wherein the method comprises screening a biological test sample from the patient for HBV infection, and administering an effective amount of Compound 1 to the patient having unresectable HCC characterized by HBV infection. In yet other embodiments, provided herein is a method for preventing unresectable HCC characterized by HBV infection in a patient, comprising screening a biological test sample from the patient for HBV infection, and administering an effective amount of Compound 1 to the patient having unresectable HCC characterized by HBV infection. Provided herein is Compound 1 for use in such a method for preventing unresectable HCC characterized by HBV infection in a patient, wherein the method comprises screening a biological test sample from the patient for HBV infection, and administering an effective amount of Compound 1 to the patient having unresectable HCC characterized by HBV infection.

In certain embodiments, the HCC characterized by HBV infection is previously untreated HCC characterized by HBV infection. Thus, in some embodiments, provided herein is a method for treating previously untreated HCC characterized by HBV infection in a patient, comprising screening a biological test sample from the patient for HBV infection, and administering an effective amount of Compound 1 to the patient having previously untreated HCC characterized by HBV infection. Provided herein is Compound 1 for use in such a method for treating previously untreated HCC characterized by HBV infection in a patient, wherein the method comprises screening a biological test sample from the patient for HBV infection, and administering an effective amount of Compound 1 to the patient having previously untreated HCC characterized by HBV infection. In other embodiments, the HCC characterized by HBV infection is previously treated HCC characterized by HBV infection. Thus, in some embodiments, provided herein is a method for treating previously treated HCC characterized by HBV infection in a patient, comprising screening a biological test sample from the patient for HBV infection, and administering an effective amount of Compound 1 to the patient having previously treated HCC characterized by HBV infection. Provided herein is Compound 1 for use in such a method for treating previously treated HCC characterized by HBV infection in a patient, wherein the method comprises screening a biological test sample from the patient for HBV infection, and administering an effective amount of Compound 1 to the patient having previously treated HCC characterized by HBV infection. In some embodiments, the HCC characterized by HBV infection is previously treated with at least one therapy. In some such embodiments, the HCC characterized by HBV infection was previously treated at least with sorafenib and/or chemotherapy. In one embodiment, the HCC characterized by HBV infection is previously treated with one therapy. In another embodiment, the HCC characterized by HBV infection is previously treated with two therapies. In still another embodiment, the HCC characterized by HBV infection is previously treated with three therapies. In still other embodiments, the HCC characterized by HBV infection is previously treated with four therapies. In some such embodiments, the HCC characterized by HBV infection is previously treated HCC, wherein the previous treatment comprises sorafenib and/or chemotherapy. In some such embodiments, the HCC characterized by HBV infection is previously treated HCC, wherein the previous treatment comprises at least sorafenib and/or chemotherapy. In some such embodiments, the HCC characterized by HBV infection is previously treated HCC, wherein the previous treatment comprises sorafenib. In some other such embodiments, the HCC characterized by HBV infection is previously treated HCC, wherein the previous treatment comprises at least chemotherapy.

In yet another aspect, provided herein is a method for selecting a patient having HCC for Compound 1 treatment, comprising a) obtaining a biological test sample from the patient; b) analyzing the sample for HBV infection; c) selecting the patient having HCC for Compound 1 treatment if HBV infection is determined in the sample. In certain embodiments, the method further comprises a step d) administering an effective amount of Compound 1 to the patient having HCC characterized by HBV infection. Thus, in some embodiments, provided herein is a method for selecting a patient having HCC for Compound 1 treatment, comprising a) obtaining a biological test sample from the patient; b) analyzing the sample for HBV infection; c) selecting the patient having HCC for Compound 1 treatment if HBV infection is determined in the sample; and d) administering an effective amount of Compound 1 to the patient having HCC characterized by HBV infection. Thus, further provided herein is Compound 1 for use in such a method for selecting a patient having HCC for Compound 1 treatment, wherein the method comprises a) obtaining a biological test sample from the patient; b) analyzing the sample for HBV infection; c) selecting the patient having HCC for Compound 1 treatment if HBV infection is determined in the sample; and d) administering an effective amount of Compound 1 to the patient having HCC characterized by HBV infection.

In certain embodiments, the HCC is unresectable HCC. In some embodiments, provided herein is a method for selecting a patient having unresectable HCC for Compound 1 treatment, comprising a) obtaining a biological test sample from the patient; b) analyzing the sample for HBV infection; c) selecting the patient having unresectable HCC for Compound 1 treatment if HBV infection is determined in the sample. In other embodiments, provided herein is a method for selecting a patient having unresectable HCC for Compound 1 treatment, comprising a) obtaining a biological test sample from the patient; b) analyzing the sample for HBV infection; c) selecting the patient having unresectable HCC for Compound 1 treatment if HBV infection is determined in the sample; and d) administering an effective amount of Compound 1 to the patient having unresectable HCC characterized by HBV infection. Thus, further provided herein is Compound 1 for use in such a method for selecting a patient having unresectable HCC for Compound 1 treatment, wherein the method comprises a) obtaining a biological test sample from the patient; b) analyzing the sample for HBV infection; c) selecting the patient having unresectable HCC for Compound 1 treatment if HBV infection is determined in the sample; and d) administering an effective amount of Compound 1 to the patient having unresectable HCC characterized by HBV infection.

In still another aspect, provided herein is a method for predicting response to treatment with Compound 1 in a patient having HCC, the method comprising: a) obtaining a biological test sample from the patient; b) analyzing the sample for HBV infection; c) predicting an increased likelihood of response to the Compound 1 treatment of the patient's HCC if HBV infection is determined in the sample. In certain embodiments, the method further comprises a step d) administering an effective amount of Compound 1 to the patient having HCC characterized by HBV infection. Thus, in some embodiments, provided herein is a method for predicting response to treatment with Compound 1 in a patient having HCC, the method comprising: a) obtaining a biological test sample from the patient; b) analyzing the sample for HBV infection; c) predicting an increased likelihood of response to the Compound 1 treatment of the patient's HCC if HBV infection is determined in the sample; and d) administering an effective amount of Compound 1 to the patient having HCC characterized by HBV infection. Thus, further provided herein is Compound 1 for use in such a method for predicting response to treatment with Compound 1 in a patient having HCC, wherein the method comprises: a) obtaining a biological test sample from the patient; b) analyzing the sample for HBV infection; c) predicting an increased likelihood of response to the Compound 1 treatment of the patient's HCC if HBV infection is determined in the sample; and d) administering an effective amount of Compound 1 to the patient having HCC characterized by HBV infection.

In certain embodiments, the HCC is unresectable HCC. In some embodiments, provided herein is a method for predicting response to treatment with Compound 1 in a patient having unresectable HCC, the method comprising: a) obtaining a biological test sample from the patient; b) analyzing the sample for HBV infection; c) predicting an increased likelihood of response to the Compound 1 treatment of the patient's unresectable HCC if HBV infection is determined in the sample. In other embodiments, provided herein is a method for predicting response to treatment with Compound 1 in a patient having unresectable HCC, the method comprising: a) obtaining a biological test sample from the patient; b) analyzing the sample for HBV infection; c) predicting an increased likelihood of response to the Compound 1 treatment of the patient's unresectable HCC if HBV infection is determined in the sample; and d) administering an effective amount of Compound 1 to the patient having unresectable HCC characterized by HBV infection. Thus, further provided herein is Compound 1 for use in such a method for predicting response to treatment with Compound 1 in a patient having unresectable HCC, wherein the method comprises: a) obtaining a biological test sample from the patient; b) analyzing the sample for HBV infection; c) predicting an increased likelihood of response to the Compound 1 treatment of the patient's unresectable HCC if HBV infection is determined in the sample; and d) administering an effective amount of Compound 1 to the patient having unresectable HCC characterized by HBV infection.

In another aspect, provided herein is a method for predicting therapeutic efficacy of Compound 1 in a patient having HCC, the method comprising: a) obtaining a biological test sample from the patient; b) analyzing the sample for HBV infection; c) predicting an increased likelihood of therapeutic efficacy of Compound 1 in the patient's HCC if HBV infection is determined in the sample. In certain embodiments, the method further comprises a step d) administering an effective amount of Compound 1 to the patient having HCC characterized by HBV infection. Thus, in some embodiments, provided herein is a method for predicting therapeutic efficacy of Compound 1 in a patient having HCC, the method comprising: a) obtaining a biological test sample from the patient; b) analyzing the sample for HBV infection; c) predicting an increased likelihood of therapeutic efficacy of Compound 1 in the patient's HCC if HBV infection is determined in the sample; and d) administering an effective amount of Compound 1 to the patient having HCC characterized by HBV infection. Thus, further provided herein is Compound 1 for use in such a method for predicting therapeutic efficacy of Compound 1 in a patient having HCC, wherein the method comprises: a) obtaining a biological test sample from the patient; b) analyzing the sample for HBV infection; c) predicting an increased likelihood of therapeutic efficacy of Compound 1 in the patient's HCC if HBV infection is determined in the sample; and d) administering an effective amount of Compound 1 to the patient having HCC characterized by HBV infection.

In certain embodiments, the HCC is unresectable HCC. In some embodiments, provided herein is a method for predicting therapeutic efficacy of Compound 1 in a patient having unresectable HCC, the method comprising: a) obtaining a biological test sample from the patient; b) analyzing the sample for HBV infection; c) predicting an increased likelihood of therapeutic efficacy of Compound 1 in the patient's unresectable HCC if HBV infection is determined in the sample. In other embodiments, provided herein is a method for predicting therapeutic efficacy of Compound 1 in a patient having unresectable HCC, the method comprising: a) obtaining a biological test sample from the patient; b) analyzing the sample for HBV infection; c) predicting an increased likelihood of therapeutic efficacy of Compound 1 in the patient's unresectable HCC if HBV infection is determined in the sample; and d) administering an effective amount of Compound 1 to the patient having unresectable HCC characterized by HBV infection. Thus, further provided herein is Compound 1 for use in such a method for predicting therapeutic efficacy of Compound 1 in a patient having unresectable HCC, wherein the method comprises: a) obtaining a biological test sample from the patient; b) analyzing the sample for HBV infection; c) predicting an increased likelihood of therapeutic efficacy of Compound 1 in the patient's unresectable HCC if HBV infection is determined in the sample; and d) administering an effective amount of Compound 1 to the patient having unresectable HCC characterized by HBV infection.

In various methods provided herein, HBV infection is determined by at least one of the variables selected from the group consisting of: patient history of HBV, prior or current treatment for HBV, cirrhosis attributed to HBV, the presence of HBV proteins or antigens, the presence of antibodies to HBV proteins or antigens, HBV viral load, and the presence of HBV DNA. In one embodiment, HBV infection is determined by patient history of HBV. In another embodiment, HBV infection is determined by prior treatment for HBV. In yet another embodiment, HBV infection is determined by current treatment for HBV. In still another embodiment, HBV infection is determined by cirrhosis attributed to HBV. In another embodiment, HBV infection is determined by the presence of HBV proteins or antigens. In another embodiment, HBV infection is determined by the presence of antibodies to HBV proteins or antigens. In yet another embodiment, HBV infection is determined by HBV viral load. In yet another embodiment, HBV infection is determined by the presence of HBV DNA. In certain embodiments, HBV infection is determined by two, three, four, five, six, seven, or all of the variables selected from the group consisting of: patient history of HBV, prior treatment for HBV, current treatment for HBV, cirrhosis attributed to HBV, the presence of HBV proteins, the presence of HBV antigens, the presence of antibodies to HBV proteins, the presence of antibodies to HBV antigens, HBV viral load, and the presence of HBV DNA.

In another embodiment, in various methods provided herein, HBV infection is determined by at least one of the variables selected from the group consisting of: the presence of HBsAg, the presence of HBcAg, the presence of HBeAg, the presence of HBxAg, the presence of HBcrAg, the presence of anti-HBsAg, the presence of anti-HBcAg, the presence of anti-HBeAg, the presence of anti-HBxAg, the presence of anti-HBcrAg, HBV viral load, the use of HBV medications, the presence of HBV DNA, the presence of HBV mRNA, and the presence of HBV protein. In one embodiment, HBV infection is determined by the presence of HBsAg. In another embodiment, HBV infection is determined by the presence of HBcAg. In another embodiment, HBV infection is determined by the presence of HBeAg. In another embodiment, HBV infection is determined by the presence of HBxAg. In another embodiment, HBV infection is determined by the presence of HBcrAg. In yet another embodiment, HBV infection is determined by the presence of anti-HBsAg. In yet another embodiment, HBV infection is determined by the presence of anti-HBcAg. In yet another embodiment, HBV infection is determined by the presence of anti-HBeAg. In yet another embodiment, HBV infection is determined by the presence of anti-HBxAg. In yet another embodiment, HBV infection is determined by the presence of anti-HBcrAg. In still another embodiment, HBV infection is determined by HBV viral load. In one embodiment, HBV infection is determined by the use of HBV medications. In one embodiment, HBV infection is determined by the presence of HBV DNA. In another embodiment, HBV infection is determined by the presence of HBV mRNA. In yet another embodiment, HBV infection is determined by the presence of HBV protein. In another embodiment, HBV infection is related to the lack of immunization. In some embodiments, HBV infection is determined by two, three, four, five, six, seven, eight, nine, ten, or all of the variables selected from the group consisting of: the presence of HBsAg, the presence of HBcAg, the presence of HBeAg, the presence of HBxAg, the presence of HBcrAg, the presence of anti-HBsAg, the presence of anti-HBcAg, the presence of anti-HBeAg, the presence of anti-HBxAg, the presence of anti-HBcrAg, HBV viral load, the use of HBV medications, the presence of HBV DNA, the presence of HBV mRNA, and the presence of HBV protein.

The HBV DNA detected can be any fragment of the HBV genome, whether encoding an HBV protein or not. The HBV mRNA detected can be any fragment of the HBV mRNA pool. The HBV protein detected can be any HBV protein or fragments thereof.

In some embodiments, the HBV DNA is the DNA encoding HBxAg or fragments thereof. In certain embodiments, the HBV mRNA is the mRNA of HBxAg or fragments thereof. In other embodiments, the HBV protein is HBxAg or fragments thereof.

In some embodiments, the HBV DNA is the DNA encoding HBsAg or fragments thereof. In certain embodiments, the HBV mRNA is the mRNA of HBsAg or fragments thereof. In other embodiments, the HBV protein is HBsAg or fragments thereof.

In some embodiments, the HBV DNA is the DNA encoding HBcAg or fragments thereof. In certain embodiments, the HBV mRNA is the mRNA of HBcAg or fragments thereof. In other embodiments, the HBV protein is HBcAg or fragments thereof.

In some embodiments, the HBV DNA is the DNA encoding HBeAg or fragments thereof. In certain embodiments, the HBV mRNA is the mRNA of HBeAg or fragments thereof. In other embodiments, the HBV protein is HBeAg or fragments thereof.

In some embodiments, the HBV DNA is the DNA encoding HBcrAg or fragments thereof. In certain embodiments, the HBV mRNA is the mRNA of HBcrAg or fragments thereof. In other embodiments, the HBV protein is HBcrAg or fragments thereof.

In various methods provided herein, HBV infection can be detected in a biological sample from a patient. In some embodiments, the biological sample is a sample from serum, plasma, blood, dried blood/plasma spots, hepatocytes, primary tumor, or sites of metastasis of HCC, including but not limited to, lungs, lymph nodes, adrenal glands, bones, peritoneum, portal vein, brain, saliva, parotid tissue, etc. In some embodiments, HBV infection is detected by serological methods. In other embodiments, HBV infection is detected by molecular methods. Serological methods include but are not limited to enzyme linked immunosorbent assay (ELISA), chemiluminescent enzyme immunoassay or chemiluminescent immunoassay (CLEIA or CLIA), time resolved fluroimmunoassay (TRFIA), chemiluminescent microparticle immunoassay (CMIA), electro-chemiluminescent immunoassay (ECLIA), and golden immunochromatographic assay (GICA). Molecular methods include but are not limited to nucleic acid hybridization, nucleic acid amplification (e.g., PCR, real time PCR, multiplex PCR, and branched DNA assay), sequencing, and enzymatic digestion of nucleic acids. Both serological and molecular methods can be conducted on automated systems (such as Abbott AxSYM, Roche Elecsys, Abbott Architect, version 2.0 of CobasAmpliPrep/CobasTaqMan (CAP/CTM)).

In certain embodiments, the various assays detect at least one biomarker of HBV selected from the group consisting of HBsAg, anti-HBsAg, HBcAg, anti-HBcAg, HBeAg, anti-HBeAg, HBxAg, anti-HBxAg, HBcrAg, and anti-HBcrAg. In one embodiment, the biomarker is HBsAg. In another embodiment, the biomarker is anti-HBsAg. In yet another embodiment, the biomarker is HBcAg. In still another embodiment, the biomarker is anti-HBcAg. In one embodiment, the biomarker is HBeAg. In another embodiment, the biomarker is anti-HBeAg. In one embodiment, the biomarker is HBxAg. In still another embodiment, the biomarker is anti-HBxAg. In still another embodiment, the biomarker is HBcrAg. In another embodiment, the biomarker is anti-HBcrAg. In yet another embodiment, the various assays detect two, three, four, five, six, seven, eight, nine or all biomarkers of HBV selected from the group consisting of HBsAg, anti-HBsAg, HBcAg, anti-HBcAg, HBeAg, anti-HBeAg, HBxAg, anti-HBxAg, HBcrAg, and anti-HBcrAg.

In various methods provided herein, Compound 1 is administered in combination with a second therapeutic agent to the HCC patient characterized by HBV infection. In one embodiment, the second therapeutic agent is sorafenib. In another embodiment, the second therapeutic agent is 3-(5-amino-2-methyl-4-oxo-4H-quinazolin-3-yl)-piperidine-2,6-dione (Compound 2). In yet another embodiment, the second therapeutic agent is an immune check point inhibitor (e.g., CTLA-4 inhibitor, PD-1 inhibitor, PD-L1 inhibitor, PD-L2 inhibitor, LAG-3 inhibitor, TIM3 inhibitor, DO inhibitor, OX40 agonist, GITR agonist, CD137 agonist, CD40 agonist, recombinant human interleukin-15). In still another embodiment, Compound 1 is administered in combination with a second and a third therapeutic agents to the HCC patient characterized by HBV infection. In some embodiment, the second and the third therapeutic agents are selected from the group consisting of sorafenib, Compound 2, and an immune check point inhibitor (e.g., PD-1 inhibitor). In one embodiment, the second and the third therapeutic agents are sorafenib and Compound 2. In another embodiment, the second and the third therapeutic agents are sorafenib and an immune check point inhibitor (e.g., PD-1 inhibitor). In yet another embodiment, the second and the third therapeutic agents are Compound 2 and an immune check point inhibitor (e.g., PD-1 inhibitor). In still another embodiment, the second and the third therapeutic agents are two different immune check point inhibitors (e.g., PD-1 inhibitor and CTLA-4 inhibitor).

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is BGB-A317, nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In a specific embodiment, Compound 1 is administered in combination with nivolumab to the patient having HCC characterized by HBV infection. Thus, provided is a method of treating HCC characterized by HBV infection, wherein the method comprises administering an effective amount of Compound 1 in combination with nivolumab to said patient. Provided herein is Compound 1 for use in a method of treating HCC characterized by HBV infection, wherein the method comprises administering an effective amount of Compound 1 in combination with nivolumab to said patient. In a specific embodiment, Compound 1 is administered in combination with nivolumab to the patient having HCC characterized by HBV infection, wherein the HCC is previously treated with at least one therapy. Thus, provided is a method of treating HCC characterized by HBV infection previously treated with at least one therapy, wherein the method comprises administering an effective amount of Compound 1 in combination with nivolumab to said patient. In one such embodiment, the previous therapy comprises sorafenib or chemotherapy. In one such embodiment, the previous therapy comprises sorafenib and chemotherapy. Provided herein is Compound 1 for use in a method of treating HCC characterized by HBV infection previously treated with at least one therapy, wherein the method comprises administering an effective amount of Compound 1 in combination with nivolumab to said patient. In a specific embodiment, Compound 1 is administered in combination with nivolumab to the patient having HCC characterized by HBV infection, wherein the HCC is previously treated with sorafenib. Thus, provided is a method of treating HCC characterized by HBV infection previously treated with sorafenib, wherein the method comprises administering an effective amount of Compound 1 in combination with nivolumab to said patient. Provided herein is Compound 1 for use in a method of treating HCC characterized by HBV infection previously treated with sorafenib, wherein the method comprises administering an effective amount of Compound 1 in combination with nivolumab to said patient. In a specific embodiment, Compound 1 is administered in combination with nivolumab to the patient having HCC characterized by HBV infection, wherein the HCC is previously treated with chemotherapy. Thus, provided is a method of treating HCC characterized by HBV infection previously treated with chemotherapy, wherein the method comprises administering an effective amount of Compound 1 in combination with nivolumab to said patient. Provided herein is Compound 1 for use in a method of treating HCC characterized by HBV infection previously treated with chemotherapy, wherein the method comprises administering an effective amount of Compound 1 in combination with nivolumab to said patient.

In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. In yet another embodiment, the anti-PD-1 antibody is AMP-224, a fusion protein. In another embodiment, the PD-1 antibody is BGB-A317. BGB-A317 is a monoclonal antibody in which the ability to bind Fc gamma receptor I is specifically engineered out, and which has a unique binding signature to PD-1 with high affinity and superior target specificity.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and Tecentriq®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., *J. Immunol.*, 2007, 179, 4202-4211). In another embodiment, the LAG-3 inhibitor is BMS-986016.

In one embodiment, the checkpoint inhibitor is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.*, 2012, 3834).

In one embodiment, the checkpoint inhibitor is a TIM3 (T-cell immunoglobulin domain and mucin domain 3) inhibitor (Fourcade et al., *J. Exp. Med.*, 2010, 207, 2175-86; Sakuishi et al., *J. Exp. Med.*, 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

Examples of such additional agents include, but are not limited to: Abraxane® (paclitaxel protein-bound particles for injectable suspension (albuin-bound)); ace-11; acivicin; aclarubicin; acodazole hydrochloride; acronine; adozelesin; aldesleukin; altretamine; ambomycin; ametantrone acetate; amrubicin; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; herceptin; hydroxyurea; idarubicin hydrochloride; ifosfamide; ilmofosine; iproplatin; irinotecan; irinotecan hydrochloride; lanreotide acetate; lapatinib; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; romidepsin; safingol; safingol hydrochloride; semustine; simtrazene; sparfosate sodium; sparsomycin; spirogermanium hydrochloride; spiromustine; spiroplatin; stem cell treatments such as PDA-001; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other examples include, but are not limited to: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; b-FGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levami sole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE'); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

In one embodiment, the patient has received at least one prior therapy for HCC. In another embodiment, the patient has received one prior therapy for HCC. In yet another embodiment, the patient has received two prior therapies for HCC. In still another embodiment, the patient has received three prior therapies for HCC. In another embodiment, the patient has received no prior therapy for HCC. In some embodiments, the prior therapy is a systemic therapy (e.g., drug treatment). In other embodiments, the prior therapy is a locoregional therapy (e.g., radiotherapy).

In one embodiment, provided herein are methods for preventing or delaying a RECIST (for example, RECIST 1.1) of PD in a patient having HCC characterized by HBV infection, comprising administering an effective amount of Compound 1 to the patient having HCC characterized by HBV infection. Provided herein is Compound 1 for use in such methods for preventing or delaying a RECIST (for example, RECIST 1.1) of PD in a patient having HCC characterized by HBV infection. In one embodiment, provided herein are methods for preventing or delaying a mRECIST for HCC of PD in a patient having HCC characterized by HBV infection, comprising administering an effective amount of Compound 1 to the patient having HCC characterized by HBV infection. Provided herein is Compound 1 for use in such methods for preventing or delaying a mRECIST for HCC of PD in a patient having HCC characterized by HBV infection. In one embodiment, the prevention or delaying of PD is characterized or achieved by a change in overall size of the target lesions, for example, between −30% and −20% compared to pre-treatment. In another embodiment, the change in size of the target lesions is a reduction in overall size of more than 30%, for example, more than 50% reduction in target lesion size compared to pre-treatment. In another, the prevention is characterized or achieved by a reduction in size or a delay in progression of non-target lesions compared to pre-treatment. In one embodiment, the prevention is achieved or characterized by a reduction in the number of target lesions compared to pre-treatment. In another, the prevention is achieved or characterized by a reduction in the number or quality of non-target lesions compared to pre-treatment. In one embodiment, the prevention is achieved or characterized by the absence or the disappearance of target lesions compared to pre-treatment. In another, the prevention is achieved or characterized by the absence or the disappearance of non-target lesions compared to pre-treatment. In another embodiment, the prevention is achieved or characterized by the prevention of new lesions compared to pre-treatment. In yet another embodiment, the prevention is achieved or characterized by the prevention of clinical signs or symptoms of disease progression compared to pre-treatment, such as HCC-related cachexia or increased pain.

In certain embodiments, provided herein are methods for decreasing the size of a target lesion in a patient having HCC characterized by HBV infection compared to pre-treatment, comprising administering an effective amount of Compound 1 to the patient having HCC characterized by HBV infection. Provided herein is Compound 1 for use in such methods for decreasing the size of a target lesion in a patient having HCC characterized by HBV infection compared to pre-treatment.

In certain embodiments, provided herein are methods for decreasing the size of a non-target lesion in a patient having HCC characterized by HBV infection compared to pre-treatment, comprising administering an effective amount of Compound 1 to the patient having HCC characterized by HBV infection. Provided herein is Compound 1 for use in such methods for decreasing the size of a non-target lesion in a patient having HCC characterized by HBV infection compared to pre-treatment.

In certain embodiments, provided herein are methods for achieving a reduction in the number of target lesions in a patient having HCC characterized by HBV infection compared to pre-treatment, comprising administering an effective amount of Compound 1 to the patient having HCC characterized by HBV infection. Provided herein is Compound 1 for use in such methods for achieving a reduction in the number of target lesions in a patient having HCC characterized by HBV infection compared to pre-treatment.

In certain embodiments, provided herein are methods for achieving a reduction in the number of non-target lesions in a patient having HCC characterized by HBV infection compared to pre-treatment, comprising administering an effective amount Compound 1 to the patient having HCC characterized by HBV infection. Provided herein is Compound 1 for use in such methods for achieving a reduction in the number of non-target lesions in a patient having HCC characterized by HBV infection compared to pre-treatment.

In certain embodiments, provided herein are methods for achieving an absence of all target lesions in a patient having HCC characterized by HBV infection, comprising administering an effective amount of Compound 1 to the patient having HCC characterized by HBV infection. Provided herein is Compound 1 for use in such methods for achieving an absence of all target lesions in a patient having HCC characterized by HBV infection.

In certain embodiments, provided herein are methods for achieving an absence of all non-target lesions in a patient having HCC characterized by HBV infection, comprising administering an effective amount of Compound 1 to the patient having HCC characterized by HBV infection. Provided herein is Compound 1 for use in such methods for achieving an absence of all non-target lesions in a patient having HCC characterized by HBV infection.

In certain embodiments, provided herein are methods for treating HCC characterized by HBV infection, the methods comprising administering an effective amount of Compound 1 to a patient having HCC characterized by HBV infection, wherein the treatment results in a CR, PR or SD, as determined by RECIST (for example, RECIST 1.1 or mRECIST for HCC). Provided herein is Compound 1 for use in such methods for treating HCC characterized by HBV infection, wherein the methods comprise administering an effective amount of Compound 1 to a patient having HCC characterized by HBV infection, wherein the treatment results in a CR, PR or SD, as determined by RECIST (for example, RECIST 1.1 or mRECIST for HCC).

In certain embodiments, provided herein are methods for treating HCC characterized by HBV infection, the methods comprising administering an effective amount of Compound 1 to a patient having HCC characterized by HBV infection, wherein the treatment results in a reduction in target lesion size, a reduction in non-target lesion size, a reduction in target lesion number, a reduction in non-target lesion number, and/or the absence of all target and/or non-target lesions, compared to pre-treatment. Provided herein is Compound 1 for use in such methods treating HCC characterized by HBV infection, wherein the methods comprise administering an effective amount of Compound 1 to a patient having HCC characterized by HBV infection, wherein the treatment results in a reduction in target lesion size, a reduction in non-target lesion size, a reduction in target lesion number, a reduction in non-target lesion number, and/or the absence of all target and/or non-target lesions, compared to pre-treatment.

In certain embodiments, provided herein are methods for treating HCC characterized by HBV infection, the methods comprising administering an effective amount of Compound 1 to a patient having HCC characterized by HBV infection, wherein the treatment results in prevention or retarding of clinical progression, such as HCC-related cachexia or increased pain. Provided herein is Compound 1 for use in such methods for treating HCC characterized by HBV infection, wherein the methods comprise administering an effective amount of Compound 1 to a patient having HCC characterized by HBV infection, wherein the treatment results in prevention or retarding of clinical progression, such as HCC-related cachexia or increased pain.

In one embodiment, provided herein are methods for improving the Eastern Cooperative Oncology Group Performance Status (ECOG) of a patient having HCC characterized by HBV infection, comprising administering an effective amount of Compound 1 to a patient having HCC characterized by HBV infection. Provided herein is Compound 1 for use in such methods for improving the Eastern Cooperative Oncology Group Performance Status (ECOG) of a patient having HCC characterized by HBV infection.

In another embodiment, provided herein are methods for inducing a therapeutic response assessed by Positron Emission Tomography (PET) outcome of a patient having HCC characterized by HBV infection, comprising administering an effective amount of Compound 1 to the patient having HCC characterized by HBV infection. Provided herein is Compound 1 for use in such methods for inducing a therapeutic response assessed by Positron Emission Tomography (PET) outcome of a patient having HCC characterized by HBV infection. In certain embodiments, provided herein are methods for treating HCC characterized by HBV infection, the methods comprising administering an effective amount of Compound 1 to a patient having HCC characterized by HBV infection, wherein the treatment results in a reduction in tumor metabolic activity, for example, as measured by fluorodeoxyglucose (FDG)-PET imaging. Provided herein is Compound 1 for use in such methods for treating HCC characterized by HBV infection, wherein the methods comprises administering an effective amount of Compound 1 to a patient having HCC characterized by HBV infection, wherein the treatment results in a reduction in tumor metabolic activity, for example, as measured by fluorodeoxyglucose (FDG)-PET imaging. Other molecular imaging agents for PET, such as choline, fluorocholine (FCH), or fluorothylcholine (FEC), are also contemplated.

In yet another embodiment, provided herein are methods for inducing a therapeutic response assessed by angiography outcome of a patient having HCC characterized by HBV infection, comprising administering an effective amount of Compound 1 to the patient having HCC characterized by HBV infection. Provided herein is Compound 1 for use in such methods for inducing a therapeutic response assessed by angiography outcome of a patient having HCC characterized by HBV infection. In certain embodiments, provided herein are methods for treating HCC characterized by HBV infection, the methods comprising administering an effective amount of Compound 1 to a patient having HCC characterized by HBV infection, wherein the treatment results in a reduction in tumor vessels as assessed by angiography. Provided herein is Compound 1 for use in such methods for treating HCC characterized by HBV infection, wherein the methods comprise administering an effective amount of Compound 1 to a patient having HCC characterized by HBV infection, wherein the treatment results in a reduction in tumor vessels as assessed by angiography.

In still another embodiment, provided herein are methods for inducing a therapeutic response assessed by ultrasonography outcome of a patient having HCC characterized by HBV infection, comprising administering an effective amount of Compound 1 to the patient having HCC characterized by HBV infection. Provided herein is Compound 1 for use in such methods for inducing a therapeutic response assessed by ultrasonography outcome of a patient having HCC characterized by HBV infection. In certain embodiments, provided herein are methods for treating HCC characterized by HBV infection, the methods comprising administering an effective amount of Compound 1 to a patient having HCC characterized by HBV infection, wherein the treatment results in a reduction in tumor mass as assessed by ultrasonography. Provided herein is Compound 1 for use in such methods for treating HCC characterized by HBV infection, the methods comprising administering an effective amount of Compound 1 to a patient having HCC characterized by HBV infection, wherein the treatment results in a reduction in tumor mass as assessed by ultrasonography.

In another embodiment, provided herein are methods for inducing a therapeutic response assessed by diffusion-weighted MRI outcome of a patient having HCC characterized by HBV infection, comprising administering an effective amount of Compound 1 to the patient having HCC characterized by HBV infection. Provided herein is Compound 1 for use in such methods for inducing a therapeutic response assessed by diffusion-weighted MM outcome of a patient having HCC characterized by HBV infection. In certain embodiments, provided herein are methods for treating HCC characterized by HBV infection, the methods comprising administering an effective amount of Compound 1 to a patient having HCC characterized by HBV infection, wherein the treatment results in a reduction in tumor lesions as assessed by diffusion-weighted MRI. Provided herein is Compound 1 for use in such methods for treating HCC characterized by HBV infection, wherein the methods comprise administering an effective amount of Compound 1 to a patient having HCC characterized by HBV infection, wherein the treatment results in a reduction in tumor lesions as assessed by diffusion-weighted MRI.

In yet another embodiment, provided herein are methods for inducing a therapeutic response assessed by acoustic radiation force impulse (ARFI) imaging outcome of a patient having HCC characterized by HBV infection, comprising administering an effective amount of Compound 1 to the patient having HCC characterized by HBV infection. Provided herein is Compound 1 for use in such methods for inducing a therapeutic response assessed by acoustic radiation force impulse (ARFI) imaging outcome of a patient having HCC characterized by HBV infection. In certain embodiments, provided herein are methods for treating HCC characterized by HBV infection, the methods comprising administering an effective amount of Compound 1 to a patient having HCC characterized by HBV infection, wherein the treatment results in a reduction in tumor stiffness as assessed by ARFI imaging. Provided herein is Compound 1 for use in such methods for treating HCC characterized by HBV infection, wherein the methods comprise administering an effective amount of Compound 1 to a patient having HCC characterized by HBV infection, wherein the treatment results in a reduction in tumor stiffness as assessed by ARFI imaging.

In certain embodiments, provided herein are methods for treating HCC characterized by HBV infection, the methods comprising administering an effective amount of Compound 1 to a patient having HCC characterized by HBV infection, wherein the treatment results in a reduction in level of AFP. Provided herein is Compound 1 for use in such methods for treating HCC characterized by HBV infection, the methods comprising administering an effective amount of Compound 1 to a patient having HCC characterized by HBV infection, wherein the treatment results in a reduction in level of AFP. In some embodiments, provided herein are methods for reducing level of AFP in a patient having HCC characterized by HBV infection, comprising administering an effective amount of Compound 1 to the patient having HCC characterized by HBV infection. Provided herein is Compound 1 for use in such methods for reducing level of AFP in a patient having HCC characterized by HBV infection. In some such embodiments, the level of AFP is assessed in a biological sample of the patient, such as in circulating blood cells and/or tumor biopsies. In such embodiments, the level of AFP is assessed by comparison of the level of AFP before and after administration of Compound 1. In certain embodiments, provided herein are methods for measuring reduction of AFP level in a patient having HCC characterized by HBV infection, comprising administering an effective amount of Compound 1 to the patient having HCC characterized by HBV infection, measuring the level of AFP in the patient, and comparing the level of AFP after and before administration of Compound 1. Provided herein is Compound 1 for use in such methods for measuring reduction of AFP level in a patient having HCC characterized by HBV infection, comprising administering an effective amount of Compound 1 to the patient having HCC characterized by HBV infection, measuring the level of AFP in the patient, and comparing the level of AFP after and before administration of Compound 1. In some embodiments, the reduction of AFP level is assessed in circulating blood cells. In some embodiments, the reduction of AFP level is assessed in tumor biopsies. In certain embodiments, the AFP level is the mRNA level of AFP. In other embodiments, the AFP level is the protein level of AFP.

In one embodiment, provided herein are methods for inhibiting phosphorylation of S6RP, 4E-BP1 and/or AKT in a patient having HCC characterized by HBV infection, comprising administering an effective amount of Compound 1 to the patient having HCC characterized by HBV infection. Provided herein is Compound 1 for use in such methods for inhibiting phosphorylation of S6RP, 4E-BP1 and/or AKT in a patient having HCC characterized by HBV infection. In some such embodiments, the inhibition of phosphorylation is assessed in a biological sample of the patient, such as in circulating blood cells and/or tumor biopsies. In such embodiments, the amount of inhibition of phosphorylation is assessed by comparison of the amount of phospho-S6RP, 4E-BP1 and/or AKT before and after administration of Compound 1. In certain embodiments, provided herein are methods for measuring inhibition of phosphorylation of S6RP, 4E-BP1 or AKT in a patient having HCC characterized by HBV infection, comprising administering an effective amount of Compound 1 to the patient having HCC characterized by HBV infection, measuring the amount of phosphorylated S6RP, 4E-BP1 and/or AKT in the patient, and comparing the amount of phosphorylated S6RP, 4E-BP1 and/or AKT after and before administration of Compound 1. Provided herein is Compound 1 for use in such methods for measuring inhibition of phosphorylation of S6RP, 4E-BP1 or AKT in a patient having HCC characterized by HBV infection, wherein the method comprises administering an effective amount of Compound 1 to the patient having HCC characterized by HBV infection, measuring the amount of phosphorylated S6RP, 4E-BP1 and/or AKT in the patient, and comparing the amount of phosphorylated S6RP, 4E-BP1 and/or AKT after and before administration of Compound 1. In some embodiments, the inhibition of phosphorylation of S6RP, 4E-BP1 and/or AKT is assessed in circulating blood cells. In some embodiments, the inhibition of phosphorylation of S6RP, 4E-BP1 and/or AKT is assessed in tumor biopsies.

In certain embodiments, provided herein are methods for inhibiting phosphorylation of S6RP, 4E-BP1 and/or AKT in a biological sample of a patient having HCC characterized by HBV infection, comprising administering an effective amount of Compound 1 to the patient having HCC characterized by HBV infection and comparing the amount of phosphorylated S6RP, 4E-BP1 and/or AKT in a biological sample of the patient obtained prior to and after administration of Compound 1, wherein less phosphorylated S6RP, 4E-BP1 and/or AKT in the biological sample obtained after administration of Compound 1 relative to the amount of phosphorylated S6RP, 4E-BP1 and/or AKT in the biological sample obtained prior to administration of Compound 1 indicates inhibition. Provided herein is Compound 1 for use in such methods for inhibiting phosphorylation of S6RP, 4E-BP1 and/or AKT in a biological sample of a patient having HCC characterized by HBV infection, wherein the method comprises administering an effective amount of Compound 1 to the patient having HCC characterized by HBV infection and comparing the amount of phosphorylated S6RP, 4E-BP1 and/or AKT in a biological sample of the patient obtained prior to and after administration of Compound 1, wherein less phosphorylated S6RP, 4E-BP1 and/or AKT in the biological sample obtained after administration of Compound 1 relative to the amount of phosphorylated S6RP, 4E-BP1 and/or AKT in the biological sample obtained prior to administration of Compound 1 indicates inhibition. In some embodiments, the inhibition of phosphorylation of S6RP, 4E-BP1 and/or AKT is assessed in circulating blood cells. In some embodiments, the inhibition of phosphorylation of S6RP, 4E-BP1 and/or AKT is assessed in tumor biopsies. Inhibition of phosphorylation of S6RP (Ser235/236 and/or Ser240/244), 4E-BP1 (Thr37/46), and/or AKT (Ser473) can be measured by various methodology including flow cytometry, ELISA, immunohistochemistry (IHC), immunofluorescence (IF) using phosphorylation-specific antibodies.

In some embodiments, provided herein are methods for treating HCC characterized by HBV infection, the methods comprising administering an effective amount of Compound 1 to a patient having HCC characterized by HBV infection, wherein the treatment results in one or more of inhibition of disease progression, inhibition of tumor growth, reduction of primary tumor, relief of tumor-related symptoms, inhibition of tumor secreted factors (e.g., AFP), delayed appearance of primary or secondary tumors, slowed development of primary or secondary tumors, decreased occurrence of primary or secondary tumors, slowed or decreased severity of secondary effects of disease, arrested tumor growth and regression of tumors, increased TTP, increased PFS, and/or increased OS, among others. Provided herein is Compound 1 for use in such methods for treating HCC characterized by HBV infection, wherein the methods comprise administering an effective amount of Compound 1 to a patient having HCC characterized by HBV infection, wherein the treatment results in one or more of inhibition of disease progression, inhibition of tumor growth, reduction of primary tumor, relief of tumor-related symptoms, inhibition of tumor secreted factors (e.g., AFP), delayed appearance of primary or secondary tumors, slowed development of primary or secondary tumors, decreased occurrence of primary or secondary tumors, slowed or decreased severity of secondary effects of disease, arrested tumor growth and regression of tumors, increased TTP, increased PFS, and/or increased OS, among others.

Further provided herein are methods for treating patients who have been previously treated for HCC, as well as those who have not previously been treated. Provided herein is Compound 1 for use in such methods for treating patients who have been previously treated for HCC, as well as those who have not previously been treated. Further provided herein are methods for treating patients who have undergone surgery in an attempt to treat HCC, as well as those who have not. Provided herein is Compound 1 for use in such methods for treating patients who have undergone surgery in an attempt to treat HCC, as well as those who have not. Because patients with HCC have heterogeneous clinical manifestations and varying clinical outcomes, the treatment given to a patient may vary, depending on his/her prognosis. The skilled clinician will be able to readily determine without undue experimentation specific secondary agents (see for example U.S. Provisional Application Nos. 61/980,124 and 61/980,125 and U.S. Patent Publication Nos. 2015/0297590 and 2015/0297605, each incorporated by reference herein in their entirety), types of surgery, and types of non-drug based standard therapy that can be effectively used to treat an individual patient with HCC.

Compound 1 can be combined with radiation therapy, chemoembolization, radio frequency ablation, thermal techniques (e.g., microwave ablation, laser ablation, and cryoablation), non-thermal techniques (e.g., reversible electroporation, irreversible electroporation, and light-activated drug therapy), or surgery. In certain embodiments, Compound 1 is administered to patient who is undergoing radiation therapy, has previously undergone radiation therapy or will be undergoing radiation therapy. In some embodiments, Compound 1 is administered to patient who is undergoing chemoembolization, has previously undergone chemoembolization or will be undergoing chemoembolization. In other embodiments, Compound 1 is administered to patient who is undergoing radio frequency ablation, has previously undergone radio frequency ablation or will be undergoing radio frequency ablation. In yet other embodiments, Compound 1 is administered to patient who is undergoing microwave ablation, has previously undergone microwave ablation or will be undergoing microwave ablation. In still other embodiments, Compound 1 is administered to patient who is undergoing laser ablation, has previously undergone laser ablation or will be undergoing laser ablation. In certain embodiments, Compound 1 is administered to patient who is undergoing cryoablation, has previously undergone cryoablation or will be undergoing cryoablation. In some embodiments, Compound 1 is administered to patient who is undergoing reversible electroporation, has previously undergone reversible electroporation or will be undergoing reversible electroporation. In other embodiments, Compound 1 is administered to patient who is undergoing irreversible electroporation, has previously undergone irreversible electroporation or will be undergoing irreversible electroporation. In yet other embodiments, Compound 1 is administered to patient who is undergoing light-activated drug therapy, has previously undergone light-activated drug therapy or will be undergoing light-activated drug therapy. In yet other embodiments, Compound 1 is administered to a patient who is undergoing tumor removal surgery, has previously undergone tumor removal surgery or will be undergoing tumor removal surgery.

Further provided herein are methods of reducing, treating and/or preventing adverse or undesired effects associated with conventional therapy including, but not limited to, surgery, chemotherapy, radiation therapy, hormonal therapy, biological therapy and immunotherapy. Provided herein is Compound 1 for use in such methods of reducing, treating and/or preventing adverse or undesired effects associated with conventional therapy including, but not limited to, surgery, chemotherapy, radiation therapy, hormonal therapy, biological therapy and immunotherapy. Compound 1 and other active ingredients can be administered to a patient prior to, during, or after the occurrence of the adverse effect associated with conventional therapy.

In some embodiments, the HCC is unresectable HCC. In certain embodiments, the HCC is resistant to at least one anticancer therapy. In other embodiments, the HCC is relapsed or refractory to at least one anticancer therapy. In yet other embodiments, the HCC is metastatic.

In each of the embodiments provided herein, the term "HCC characterized by HBV infection" is interchangeable with the terms "HCC associated with HBV infection," "HCC related to HBV infection," "HCC with a history of HBV infection," "HBV positive HCC," "HBV associated HCC," "HBV related HCC," or "HBV infected HCC."

5.4 Pharmaceutical Compositions and Routes of Administration

Compositions as provided herein can be used in all methods provided herein.

Provided herein are compositions comprising an effective amount of Compound 1 and compositions comprising an effective amount of Compound 1 and pharmaceutically acceptable carriers or vehicles. In some embodiments, the pharmaceutical composition described herein is suitable for oral, parenteral, mucosal, transdermal or topical administration.

Compositions of Compound 1 include the pharmaceutical compositions provided in U.S. Pat. No. 9,403,829, issued on Aug. 2, 2016; and U.S. Pat. No. 9,604,939, issued on Mar. 28, 2017, the entire contents of each of which are incorporated herein by reference.

Compound 1 can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfate, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of Compound 1 in the pharmaceutical composition may be at a level that will exercise the desired effect; for example, about 0.005 mg/kg of a patient's body weight to about 10 mg/kg of a patient's body weight in unit dosage for both oral and parenteral administration. In certain embodiments, the pharmaceutical composition comprises Compound 1 and suitable additives. In other embodiments, the pharmaceutical composition comprises Compound 1 only. In yet other embodiments, the pharmaceutical composition comprises Compound 1 and suitable additives in capsules. In still other embodiments, the pharmaceutical composition comprises Compound 1 only in capsules.

The dose of Compound 1 to be administered to a patient is rather widely variable and can be patient-dependent to the judgment of a health-care practitioner. In general, Compound 1 can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, one dose is given per day. In another embodiment, two doses are given per day. In any given case, the amount of Compound 1 administered will depend on such factors as the solubility of the active component, the formulation used and the route of administration. In some embodiments, the effective amount of Compound 1 in the pharmaceutical composition is about 0.01, 0.25, 0.05, 0.75, 0.1, 0.2, 0.3, 0.4, 0.5, 0.6, 0.7, 0.8, 0.9, 1.0, 2.0, 3.0, 4.0, 5.0 mg/kg of a patient's body weight in unit dosage for oral administration. In one embodiment, the effective amount of Compound 1 in the pharmaceutical composition is about 0.21 mg/kg of a patient's body weight in unit dosage for oral administration. In another embodiment, the effective amount of Compound 1 in the pharmaceutical composition is about 0.43 mg/kg of a patient's body weight in unit dosage for oral administration. In yet another embodiment, the effective amount of Compound 1 in the pharmaceutical composition is about 0.64 mg/kg of a patient's body weight in unit dosage for oral administration.

In another embodiment, provided herein are methods for the treatment or prevention of HCC characterized by HBV infection comprising administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of Compound 1 to a patient in need thereof. Provided herein is Compound 1 for use in such methods for the treatment or prevention of HCC characterized by HBV infection, wherein the method comprises administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of Compound 1 to a patient in need thereof. In a particular embodiment, the methods disclosed herein comprise administration of 15 mg/day, 30 mg/day, 45 mg/day or 60 mg/day of Compound 1 to a patient in need thereof. In another embodiment, the methods disclosed herein comprise administration of 0.5 mg/day, 1 mg/day, 2 mg/day, 4 mg/day, 8 mg/day, 16 mg/day, 20 mg/day, 25 mg/day, 30 mg/day or 40 mg/day of Compound 1 to a patient in need thereof. In a particular embodiment, the methods disclosed herein comprise administration of 15 mg/day, 20 mg/day, or 30 mg/day of Compound 1 to a patient in need thereof. In some such embodiments, the methods additionally comprise administration of 240 mg nivolumab every 2 weeks. In some such embodiments, the methods additionally comprise administration of 480 mg nivolumab every 4 weeks.

In another embodiment, provided herein are methods for the treatment or prevention of HCC characterized by HBV infection comprising administration of about 0.1 mg/day to about 1200 mg/day, about 1 mg/day to about 100 mg/day, about 10 mg/day to about 1200 mg/day, about 10 mg/day to about 100 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of Compound 1 to a patient in need thereof. Provided herein is Compound 1 for use in such methods for the treatment or prevention of HCC characterized by HBV infection, wherein the method comprises administration of about 0.1 mg/day to about 1200 mg/day, about 1 mg/day to about 100 mg/day, about 10 mg/day to about 1200 mg/day, about 10 mg/day to about 100 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of Compound 1 to a patient in need thereof. In a particular embodiment, the methods disclosed herein comprise administration of 0.1 mg/day, 0.5 mg/day, 1 mg/day, 10 mg/day, 15 mg/day, 20 mg/day, 30 mg/day, 40 mg/day, 45 mg/day, 50 mg/day, 60 mg/day, 75 mg/day, 100 mg/day, 125 mg/day, 150 mg/day, 200 mg/day, 250 mg/day, 300 mg/day, 400 mg/day, 600 mg/day or 800 mg/day of Compound 1 to a patient in need thereof. In a specific embodiment, the methods disclosed herein comprise administration of 0.1 mg/day of Compound 1 to a patient in need thereof. In a specific embodiment, the methods disclosed herein comprise administration of 0.5 mg/day of Compound 1 to a patient in need thereof. In a specific embodiment, the methods disclosed herein comprise administration of 1 mg/day of Compound 1 to a patient in need thereof. In a specific embodiment, the methods disclosed herein comprise administration of 10 mg/day of Compound 1 to a patient in need thereof. In a specific embodiment, the methods disclosed herein comprise administration of 15 mg/day of Compound 1 to a patient in need thereof. In a specific embodiment, the methods disclosed herein comprise administration of 20 mg/day of Compound 1 to a patient in need thereof. In a specific embodiment, provided herein are methods for the treatment or prevention of HCC characterized by HBV infection comprising administration of 30 mg/day of Compound 1 to a patient in need thereof. Provided herein is Compound 1 for use in such methods for the treatment or prevention of HCC characterized by HBV infection, wherein the method comprises administration of 30 mg/day of Compound 1 to a patient in need thereof. In a specific embodiment, the methods disclosed herein comprise administration of 40 mg/day of Compound 1 to a patient in need thereof. In another specific embodiment, provided herein are methods for the treatment or prevention of HCC characterized by HBV infection comprising administration of 45 mg/day of Compound 1 to a patient in need thereof. Provided herein is Compound 1 for use in such methods for the treatment or prevention of HCC characterized by HBV infection, wherein the method comprises administration of 45 mg/day of Compound 1 to a patient in need thereof. In a specific embodiment, the methods disclosed herein comprise administration of 50 mg/day of Compound 1 to a patient in need thereof. In a specific embodiment, the methods disclosed herein comprise administration of 60 mg/day of Compound 1 to a patient in need thereof. In a specific embodiment, the methods disclosed herein comprise administration of 75 mg/day of Compound 1 to a patient in need thereof. In a specific embodiment, the methods disclosed herein comprise administration of 100 mg/day of Compound 1 to a patient in need thereof. In a specific embodiment, the methods disclosed herein comprise administration of 125 mg/day of Compound 1 to a patient in need thereof. In a specific embodiment, the methods disclosed herein comprise administration of 150 mg/day of Compound 1 to a patient in need thereof. In a specific embodiment, the methods disclosed herein comprise administration of 200 mg/day of Compound 1 to a patient in need thereof. In a specific embodiment, the methods disclosed herein comprise administration of 250 mg/day of Compound 1 to a patient in need thereof. In a specific embodiment, the methods disclosed herein comprise administration of 300 mg/day of Compound 1 to a patient in need thereof. In a specific embodiment, the methods disclosed herein comprise administration of 400 mg/day of Compound 1 to a patient in need thereof. In a specific embodiment, the methods disclosed herein comprise administration of 600 mg/day of Compound 1 to a patient in need thereof. In a specific embodiment, the methods disclosed herein comprise administration of 800 mg/day of Compound 1 to a patient in need thereof. In some such embodiments, the methods additionally comprise administration of 240 mg nivolumab every 2 weeks. In some such embodiments, the methods additionally comprise administration of 480 mg nivolumab every 4 weeks.

In another embodiment, provided herein are unit dosage formulations that comprise between about 0.1 mg and about 2000 mg, about 1 mg and 200 mg, about 35 mg and about 1400 mg, about 125 mg and about 1000 mg, about 250 mg and about 1000 mg, or about 500 mg and about 1000 mg of Compound 1. In one embodiment, provided herein are unit dosage formulations that comprise between about 0.1 mg and about 2000 mg of Compound 1. In one embodiment, provided herein are unit dosage formulations that comprise between about 1 mg and 200 mg of Compound 1. In one embodiment, provided herein are unit dosage formulations that comprise between about 35 mg and about 1400 mg of Compound 1. In one embodiment, provided herein are unit dosage formulations that comprise between about 125 mg and about 1000 mg of Compound 1. In one embodiment, provided herein are unit dosage formulations that comprise between about 250 mg and about 1000 mg of Compound 1. In one embodiment, provided herein are unit dosage formulations that comprise between about 500 mg and about 1000 mg of Compound 1.

In a particular embodiment, provided herein are unit dosage formulation comprising about 0.1 mg, 0.25 mg, 0.5 mg, 1 mg, 5 mg, 10 mg, 15 mg, 20 mg, 30 mg, 45 mg, 50 mg, 60 mg, 75 mg, 100 mg, 125 mg, 150 mg, 200 mg, 250 mg, 300 mg, 400 mg, 600 mg or 800 mg of Compound 1.

In another embodiment, provided herein are unit dosage formulations that comprise 0.1 mg, 0.25 mg, 0.5 mg, 1 mg, 2.5 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of Compound 1. In a particular embodiment, provided herein are unit dosage formulations that comprise about 5 mg, about 15 mg, about 20 mg, about 30 mg, about 45 mg, and about 50 mg of Compound 1. In one embodiment, provided herein are unit dosage formulations that comprise 0.1 mg of Compound 1. In one embodiment, provided herein are unit dosage formulations that comprise 0.25 mg of Compound 1. In one embodiment, provided herein are unit dosage formulations that comprise 0.5 mg of Compound 1. In one embodiment, provided herein are unit dosage formulations that comprise 1 mg of Compound 1. In one embodiment, provided herein are unit dosage formulations that comprise 2.5 mg of Compound 1. In another embodiment, provided herein are unit dosage formulations that comprise 5 mg of Compound 1. In yet another embodiment, provided herein are unit dosage formulations that comprise 10 mg of Compound 1. In one embodiment, provided herein are unit dosage formulations that comprise 15 mg of Compound 1. In still another embodiment, provided herein are unit dosage formulations that comprise 20 mg of Compound 1. In one embodiment, provided herein are unit dosage formulations that comprise 30 mg of Compound 1. In one embodiment, provided herein are unit dosage formulations that comprise 35 mg of Compound 1. In another embodiment, provided herein are unit dosage formulations that comprise 45 mg of Compound 1. In one embodiment, provided herein are unit dosage formulations that comprise 50 mg of Compound 1. In one embodiment, provided herein are unit dosage formulations that comprise 60 mg of Compound 1. In one embodiment, provided herein are unit dosage formulations that comprise 70 mg of Compound 1. In one embodiment, provided herein are unit dosage formulations that comprise 100 mg of Compound 1. In one embodiment, provided herein are unit dosage formulations that comprise 125 mg of Compound 1. In one embodiment, provided herein are unit dosage formulations that comprise 140 mg of Compound 1. In one embodiment, provided herein are unit dosage formulations that comprise 175 mg of Compound 1. In one embodiment, provided herein are unit dosage formulations that comprise 200 mg of Compound 1. In one embodiment, provided herein are unit dosage formulations that comprise 250 mg of Compound 1. In one embodiment, provided herein are unit dosage formulations that comprise 280 mg of Compound 1. In one embodiment, provided herein are unit dosage formulations that comprise 350 mg of Compound 1. In one embodiment, provided herein are unit dosage formulations that comprise 500 mg of Compound 1. In one embodiment, provided herein are unit dosage formulations that comprise 560 mg of Compound 1. In one embodiment, provided herein are unit dosage formulations that comprise 700 mg of Compound 1. In one embodiment, provided herein are unit dosage formulations that comprise 750 mg of Compound 1. In one embodiment, provided herein are unit dosage formulations that comprise 1000 mg of Compound 1. In one embodiment, provided herein are unit dosage formulations that comprise 1400 mg of Compound 1.

Compound 1 can be administered once daily (QD), or divided into multiple daily doses such as twice daily (BID), three times daily (TID), and four times daily (QID). In a specific embodiment, Compound 1 is administered QD. In another embodiment, Compound 1 is administered BID. In yet another embodiment, Compound 1 is administered TID. In still another embodiment, Compound 1 is administered QID. In addition, the administration can be continuous (i.e., daily for consecutive days or every day), intermittent, e.g., in cycles (i.e., including days, weeks, or months of rest without drug). In a preferred embodiment, the administration is continuous. In another preferred embodiment, Compound 1 is administered in 28-day cycles. In a preferred embodiment, Compound 1 is administered continuously in a daily dosing in 28-day cycles. In a preferred embodiment, Compound 1 is administered continuously in a daily dosing in 28-day cycles at a dose of 30 mg/day. In a preferred embodiment, Compound 1 is administered continuously in a daily dosing in 28-day cycles at a dose of 45 mg/day. In a preferred embodiment, Compound 1 is administered continuously in a daily dosing in 28-day cycles at a dose of 30 mg/day with no rest period between each 28-day cycle. In a preferred embodiment, Compound 1 is administered continuously in a daily dosing in 28-day cycles at a dose of 45 mg/day with no rest period between each 28-day cycle.

Compound 1 can be administered orally for reasons of convenience. In one embodiment, when administered orally, Compound 1 is administered with a meal and water. In another embodiment, Compound 1 is dispersed in water or juice (e.g., apple juice or orange juice) and administered orally as a suspension. In another embodiment, when administered orally, Compound 1 is administered in a fasted state. Preferably, Compound 1 is administered orally. In one preferred embodiment, Compound 1 is administered orally at a dose of 30 mg/day. In another preferred embodiment, Compound 1 is administered orally at a dose of 45 mg/day. In a preferred embodiment, Compound 1 is administered continuously in a daily oral dosing in 28-day cycles at a dose of 30 mg/day. In another preferred embodiment, Compound 1 is administered continuously in a daily oral dosing in 28-day cycles at a dose of 45 mg/day. In a preferred embodiment, Compound 1 is administered continuously in a daily oral dosing in 28-day cycles at a dose of 30 mg/day with no rest period between each 28-day cycle. In another preferred embodiment, Compound 1 is administered continuously in a daily oral dosing in 28-day cycles at a dose of 45 mg/day with no rest period between each 28-day cycle.

Compound 1 can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner and can depend in-part upon the site of the medical condition.

In one embodiment, provided herein are capsules containing Compound 1 without an additional carrier, excipient or vehicle.

In another embodiment, provided herein are compositions comprising an effective amount of Compound 1 and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing Compound 1 with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. In one embodiment, the pharmaceutical composition is lactose-free. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer Compound 1 as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of Compound 1 can be delayed or prolonged by proper formulation. For example, a slowly soluble pellet of Compound 1 can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending Compound 1 in oily or emulsified vehicles that allow it to disperse slowly in the serum.

5.5 Kits

In certain embodiments, provided herein are kits comprising Compound 1. In particular embodiments, provided herein are kits comprising a unit dosage form comprising Compound 1 in a sealed container, wherein the unit dosage form comprises about 1 mg to about 100 mg of Compound 1. In particular embodiments, provided herein are kits comprising a unit dosage form comprising Compound 1 in a sealed container, wherein the unit dosage form comprises about 5 mg, about 20 mg or about 50 mg of Compound 1.

In other embodiments, provide herein are kits comprising Compound 1 and means for monitoring patient response to administration of Compound 1. In certain embodiments, the patient has HCC characterized by HBV infection. In particular embodiments, the patient response measured is inhibition of disease progression, inhibition of tumor growth, reduction of primary and/or secondary tumor(s), relief of tumor-related symptoms, improvement in quality of life, inhibition of tumor secreted factors (e.g., AFP), delayed appearance of primary and/or secondary tumor(s), slowed development of primary and/or secondary tumor(s), decreased occurrence of primary and/or secondary tumor(s), slowed or decreased severity of secondary effects of disease, arrested tumor growth and/or regression of tumors.

In other embodiments, provide herein are kits comprising Compound 1 and means for monitoring patient response to administration of Compound 1, wherein said response is RECIST (for example, RECIST 1.1 or mRECIST for HCC) or ECOG.

In other embodiments, provided herein are kits comprising Compound 1 and means for measuring the amount of inhibition of phosphorylation of S6RP, 4E-BP1 and/or AKT in a patient. In certain embodiments, the kits comprise means for measuring inhibition of phosphorylation of S6RP, 4E-BP1 and/or AKT in circulating blood cells and/or tumor biopsies of a patient. In certain embodiments, provided herein are kits comprising Compound 1 and means for measuring the amount of inhibition of phosphorylation as assessed by comparison of the amount of phospho-S6RP, 4E-BP1 and/or AKT before, during and/or after administration of Compound 1. In certain embodiments, the patient has HCC characterized by HBV infection.

Inhibition of phosphorylation of S6RP, 4E-BP1, and/or AKT can be measured in blood, skin, tumor, and/or circulating tumor cells (CTCs) in blood by various methodology including flow cytometry, ELISA, IHC using phosphorylation-specific antibodies.

In certain embodiments, the kits provided herein comprise an amount of Compound 1 effective for treating or preventing HCC characterized by HBV infection.

In certain embodiments, the kits provided herein further comprise instructions for use, such as for administering Compound 1 and/or monitoring patient response to administration of Compound 1.

6. EXAMPLES

6.1 Clinical Study 1

A Phase 1/2 Multi-Center, Open-Label, Dose Finding Study to Assess the Safety, Tolerability, PK and Preliminary Efficacy of Compound 1 Administered Orally to Subjects with Phase 1/2, Multi-Center, Open-Label, Dose Finding Study to Assess the Safety, Tolerability, PK and Preliminary Efficacy of Compound 1 Administered Orally to Subjects with Phase 1/2, Multi-Center, Open Label, Dose Finding Study to Assess the Safety, Tolerability, PK and Preliminary Efficacy of Compound 1 Administered Orally to Subjects with Phase 1/2, Multi-Center, Open-Label, Dose Finding Study to Assess the Safety, Tolerability, PK and Preliminary Efficacy of Compound 1 Administered Orally to Subjects with HCC.

The study was designed as a Phase 1/2 trial consisting of two parts: dose escalation (Part A) and dose expansion (Part B).

Part A was an open-label, dose-escalating study of subjects with various hematologic or solid malignancies. The primary objectives were to determine the maximum tolerated dose (MTD) and the preliminary PK of Compound 1. The MTD of Compound 1 was determined to be 45 mg/day, and the nontolerated dose (NTD) was determined to be 60 mg/day. The PK and PD data supported once daily dosing with Compound 1.

Part B, the preliminary efficacy-seeking phase, was an open-label, dose-expansion study, which involved subjects with HCC.

The primary objectives for Part B were (a) to determine the safety and tolerability of Compound 1 when administered orally and (b) to determine the preliminary PK of Compound 1 following both single and multiple oral dosing of Compound 1.

The secondary objectives of Part B were: (a) to provide information on the preliminary efficacy of Compound 1; (b) to characterize the PK of M1 (the metabolite of Compound 1) following oral dosing of Compound 1; (c) to characterize the PK of Compound 1 and M1 in subjects with HCC; and (d) to evaluate the extent of inhibition of phosphorylation of S6RP and/or 4E-BP1 for mTORC1 activity and AKT and/or other relevant biomarkers for mTORC2 activity in peripheral blood samples and tumor biopsies following treatment with Compound 1.

Figure 1:
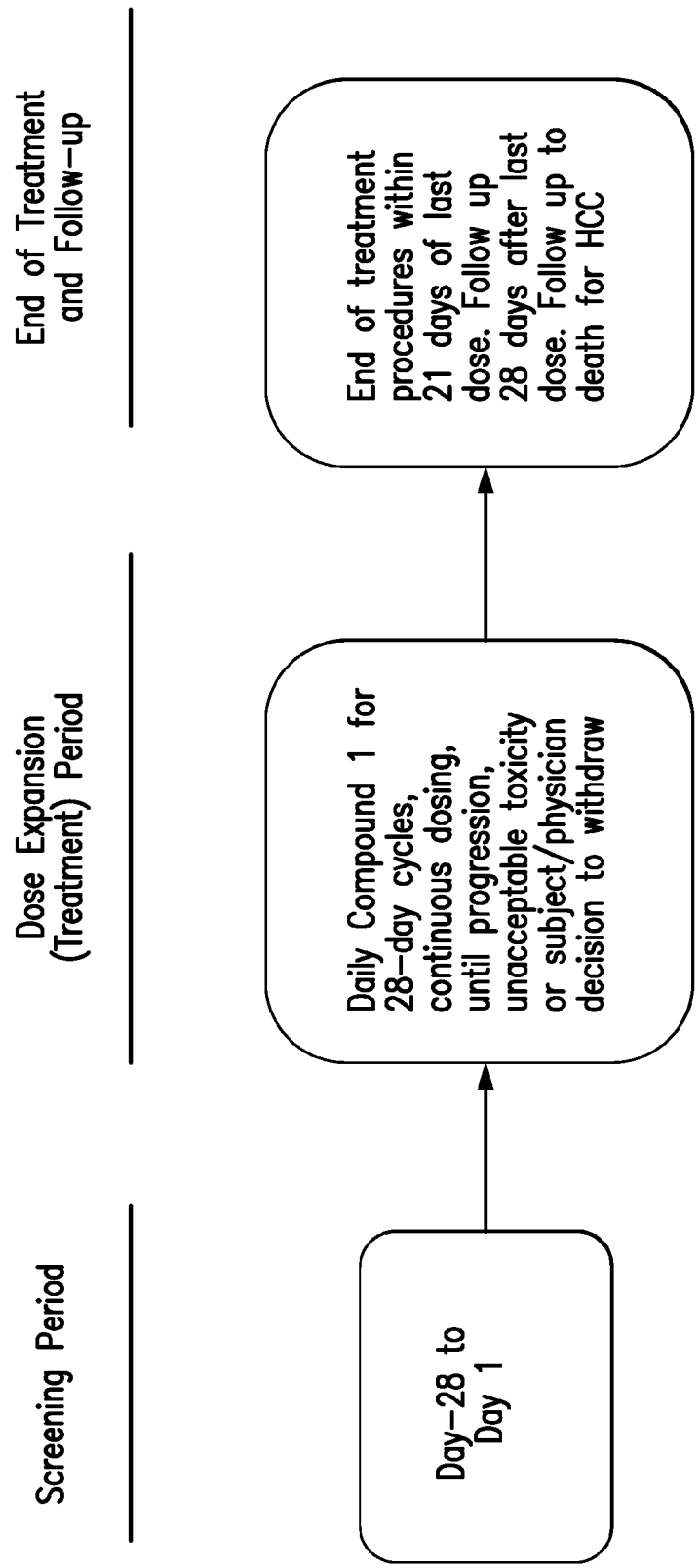

Subjects received continuous daily dosing of Compound 1 in 28-day cycles (FIG. 1). Therapy was discontinued if there was evidence of disease progression, but subjects continued to receive Compound 1 as long as the investigator considered that the subjects derived benefit from treatment. Therapy was discontinued if there was unacceptable toxicity or if the subject decided to withdraw from the study. Subjects were contacted 28 days after the last dose of study drug to assess the status of adverse events (AEs) and to determine whether any new events or death had occurred. In addition to those subjects who had died on study, approximately 28 subjects were consented for follow-up every 2 months (±1 week) after completing the treatment phase in order to determine their date of death and complete an overall survival analysis.

The inclusion criteria for selection of study population include: (1) understand and voluntarily sign an informed consent document prior to any study-related assessments/procedures were conducted; (2) men and women, ≥18 years old, with histologically or cytologically-confirmed, advanced unresectable HCC including subjects who had progressed on (or not been able to tolerate) standard anti-cancer therapy or for whom no standard anticancer therapy exists; (3) ECOG performance status of 0 or 1; (4) subjects must have had the following laboratory values: absolute neutrophil count ≥1.5×109/L, hemoglobin ≥9 g/dL, platelets ≥100×109/L, potassium within normal limits or correctable with supplements, aspartate aminotransferase (AST) and alanine aminotransferase (ALT) ≤2.5×upper limit of normal (ULN) or ≤5.0×ULN, serum bilirubin ≤1.5×ULN or ≤2×ULN, serum creatinine ≤1.5×ULN or 24-hour clearance ≥50 mL/min, negative serum or urine pregnancy test within 48 hours before starting study treatment in females of childbearing potential; (5) able to adhere to the study visit schedule and other protocol requirements; (6) retrieval of formalin-fixed, paraffin embedded archival tumor tissue, either in tumor blocks or sectioned/mounted specimens for gene mutation and/or IHC biomarker assay. Only in exceptional circumstances was an exemption waiver granted by the sponsor. (7) satisfactory screening biopsy for gene mutation and/or IHC biomarker assay for accessible tumors; (8) histologically-confirmed HCC with measurable disease. The following criteria are in addition to, or supersede, above criteria where applicable: platelet count ≥60×109/L if portal hypertension was present, Child-Pugh score of <7 (i.e., Class A liver function or better), at least 4 weeks from last dose of α-interferon and/or ribavirin, at least 4 weeks from prior percutaneous ethanol injection, radiofrequency ablation, transarterial embolization, or cryotherapy with documentation of progressive or recurrent disease.

The exclusion criteria for selection of study population include: (1) symptomatic central nervous system metastases. Subjects with brain metastases that had been previously treated and were stable for 6 weeks were allowed. (2) known acute or chronic pancreatitis; (3) subjects with any peripheral neuropathy ≥National Cancer Institute Common Terminology Criteria for Adverse Events (NCI CTCAE) Grade 2; (4) subjects with persistent diarrhea or malabsorption Grade ≥2, despite medical management; (5) impaired cardiac function or clinically significant cardiac diseases, including any of the following: left ventricular ejection fraction (LVEF)<45% as determined by multiple gated acquisition (MUGA) scan or echocardiogram, complete left bundle branch, or bifascicular, block, congenital long QT syndrome, persistent or clinically meaningful ventricular arrhythmias or atrial fibrillation, QT interval with Fridericia correction (QTcF)>460 msec on screening ECG (mean of triplicate recordings), unstable angina pectoris or myocardial infarction ≤3 months prior to starting Compound 1, other clinically significant heart disease such as congestive heart failure requiring treatment or uncontrolled hypertension (blood pressure ≥160/95 mmHg); (6) subjects with diabetes on active treatment or subjects with either of the following: fasting blood glucose ≥126 mg/dL (7.0 mmol/L), or glycosylated hemoglobin (HbA1c) ≥6.5%; (7) other concurrent severe and/or uncontrolled concomitant medical conditions (e.g., active or uncontrolled infection) that could have caused unacceptable safety risks or compromised compliance with the protocol; (8) prior systemic cancer-directed treatments or investigational modalities ≤5 half lives or 4 weeks, whichever was shorter, prior to starting study drug or who had not recovered from side effects of such therapy. Subjects must have recovered from any effects of recent radiotherapy that might have confounded the safety evaluation of study drug. (9) subjects who had undergone major surgery ≤2 weeks prior to starting study drug or who had not recovered from side effects of such therapy; (10) women who were pregnant or breast feeding. Adults of reproductive potential not employing 2 forms of birth control: (a) female subjects of childbearing potential must have agreed to use 2 adequate forms of contraception methods simultaneously (one must have been non-hormonal) from the time of giving informed consent until 28 days after the last dose of Compound 1. Female subjects of child-bearing potential, defined as sexually mature women who had not undergone a hysterectomy or bilateral oophorectomy, or who had not been naturally postmenopausal (i.e., who had not menstruated at all) for at least 24 consecutive months. (b) male subjects with partners who were female with child-bearing potential must have agreed that they or their partners would use at least 2 effective contraceptive methods (including 1 barrier method) when engaging in reproductive sexual activity throughout the study, and would avoid conceiving for 28 days after the last dose of Compound 1. (11) subjects with known human immunodeficiency virus infection; (12) any significant medical condition, laboratory abnormality, or psychiatric illness that would have prevented the subject from participating in the study; (13) any condition including the presence of laboratory abnormalities, which placed the subject at unacceptable risk if he/she were to participate in the study; (14) any condition that confounded the ability to interpret data from the study; (15) concurrent active second malignancy for which the subject was receiving therapy, excluding nonmelanomatous skin cancer or carcinoma in situ of the cervix.

Compound 1 was supplied in three strengths, 2.5 mg, 10 mg, and 20 mg, containing only the active pharmaceutical ingredient in reddish brown size Number 1 gelatin capsules for oral administration. No other excipients were used.

HBV Status of HCC Patients

An algorithm was developed to identify study subjects with HCC considered to have either a chronic HBV or a history of it. Variables in the clinical trial database used for the algorithm included the following: history of HBV, prior or current treatment for HBV, cirrhosis attributed to HBV, and hepatitis serology (Table 1). A review using the algorithm identified 12 subjects as HBV positive.

TABLE 1

Determination of HBV Status of Subjects Using Algorithm

| | Serology[a] | | | | Final HBV |
|---|---|---|---|---|---|
| HBsAg | Anti-HBsAg | Anti-HBcAg | HBV load | HBV medications | Status Determination |
| | | | | + | Positive |
| | | | >20 IU/mL | | Positive |
| + | | + | + | | Positive |
| + | | + | | | Positive |
| + | | | + | | Positive |
| + | | | | | Positive |
| + | + | + | + | | Positive |
| + | + | + | | | Positive |
| | | + | + | | Positive |
| | + | | | | Negative |
| | | + | | | Negative |

Anti-HBc = antibody to hepatitis B core antigen;
Anti-HBs = antibody to hepatitis B surfaceantigen;
HBsAG = hepatitis B surface antigen;
HBV = hepatitis B virus.
[a]"+" = Positive serology for HBsAG, antiHBs, antiHBc, or HBV viral load at screening or Cycle 1 Day 1.

Accordingly to the original protocol of Part B, 25 HCC patients started treatment of Compound 1 at 45 mg/day. After the protocol Amendment 9, 28 new HCC subjects in an additional cohort were started at 30 mg/day. The appropriateness of the 30 mg/day dose was supported by the PK and PD data from Part A. Compound 1 was administered orally, in an uninterrupted once daily schedule with no rest period between each 28-day cycle. Subjects continued to receive Compound 1 for as long as they derived benefit from treatment as judged by the investigator. Patient characteristics of the HCC patients are shown in FIG. 2.

PK Analysis

The PK profiles of Compound 1 and its metabolite M1 were determined from serial blood and urine collections during the first treatment cycle. Plasma and urine Compound 1 and M1 were measured using validated chiral liquid chromatography-mass spectrometry methods. The lower limit of quantification (LLOQ) in plasma was 1.00 or 2.00 ng/mL for Compound 1 and 10.0 ng/mL for M1. The LLOQ in urine was 5.00 ng/mL for Compound 1 and 20 ng/mL for M1.

The following general PK parameters were assessed:

$AUC_\infty$: area under the plasma concentration-time curve after a dose of Compound 1

$AUC_t$: area under the plasma concentration-time curve from time 0 to the last measurable concentration at time t $AUC_\tau$: area under the plasma concentration-time curve from time 0 to τ, where τ is the dosing interval $AUC_{\%\ extrap}$: percentage of $AUC_\infty$ due to extrapolation from the last quantifiable time to infinity $C_{max}$: peak (maximum) plasma concentration $T_{max}$: time to peak (maximum) plasma concentration CL/F: total body clearance $CL_{ss}/F$: total body clearance at steady state Vz/F: apparent volume of distribution Rac ($AUG_\tau$): accumulation ratio based on $AUC_\tau$ $T_{last}$: time of last measurable concentration $C_{last}$: last measurable concentration $\lambda_z$: terminal elimination rate constant (first-order)

Figures 3A, 3B:
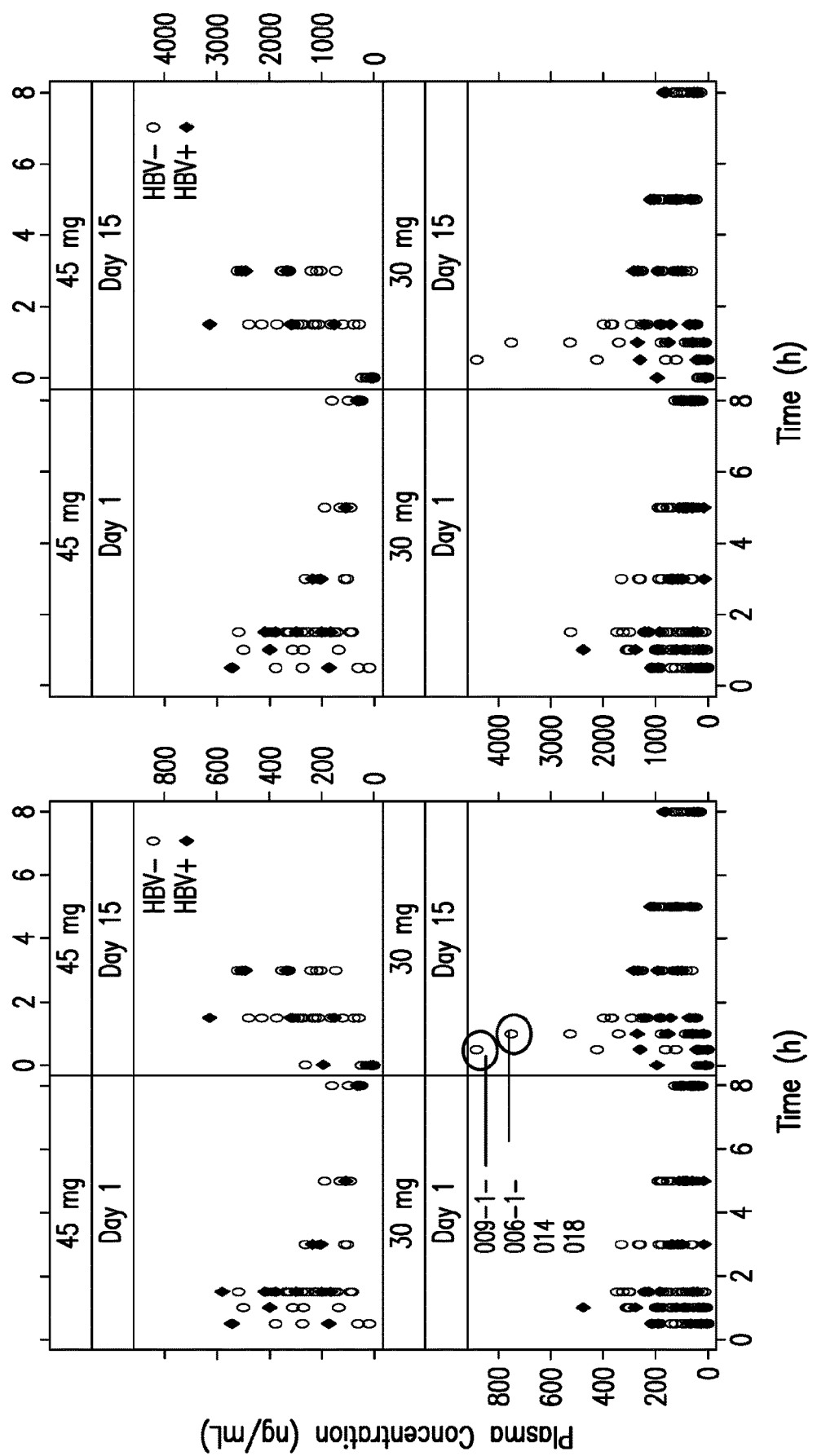
FIGS. 3A and 3B show pharmacokinetics (PK) data of Compound 1 (FIG. 3A) and its metabolite M1 (FIG. 3B) in HCC-HBV positive patients (n=12) and HCC-HBV negative patients (n=39).

$\lambda_z$ lower: lower limit of time (h) included in the calculation of $\lambda_z$ $\lambda_z$ N: number of data points used in the calculation of $\lambda_z$ $\lambda_z$ upper: upper limit of time (h) included in the calculation of $\lambda_z$ HL $\lambda_z$: terminal half-life FIGS. 3A and 3B show plasma concentration of Compound 1 (FIG. 3A) and its metabolite M1 (FIG. 3B) in HBV infected HCC patients (n=12) and non-HBV infected HCC patients (n=39). In FIG. 3A, overlap of the exposure data for HBV infected HCC patients and non-HBV infected HCC patients indicates that the Compound 1 exposure in HBV infected HCC patients is comparable to the exposure observed in non-HBV infected HCC patients. Similar results for the M1 exposure were shown in FIG. 3B.

Subject Disposition for the HCC Patients

All subjects enrolled in Part B were included in the analysis of subject disposition. Reasons for study discontinuation include the following categories: adverse effect, disease progression, withdrew consent, death, lost to follow-up, protocol violation, and other.

Information on HCC patient disposition by HBV status in the TP is shown in FIG. 4. Of the 25 HCC patients enrolled for 45 mg/day Compound 1 treatment, 17 were determined to be EE. Of the 28 HCC patients enrolled for 30 mg/day Compound 1 treatment, 24 were determined to be EE. Thus, of the total 53 HCC patients, 41 patients were evaluable for efficacy after 13 withdrew prior to first valid restaging. Of the total 53 HCC patients, 12 were determined to be HBV infected, and 41 were non-HBV infected.

Efficacy Analysis

All efficacy analyses were based on both the TP and EE Population. Subjects were evaluated for efficacy during Cycles 2, 4, 6, and every 3 months after Cycle 6. The primary efficacy variable was response rate. Efficacy endpoints for HCC matured once all enrolled subjects had withdrawn from the study.

Tumor response for HCC was based on investigator's overall evaluation with RECIST. Response rate was determined by a best overall response of either CR or PR. Disease control rate (DCR) included CR, PR, and SD.

OS was defined as the time from first dose to death. All deaths, regardless of the cause of death, were included. Subjects who had not died were censored at the last contact date when the subject was known to be alive or the clinical cut-off date, whichever was earlier.

Median of OS times were calculated using the Kaplan-Meier method and the corresponding 95% CIs were presented. The Kaplan-Meier survival curves are presented in FIGS. 5A and 5B.

Median OS for the HCC cohort was 6.9 months (FIG. 5A), and median PFS was 16 weeks (FIG. 6A). Although it was not statistically significant, a trend towards increased OS in HBV infected HCC patients versus non-HBV infected HCC patients was observed. For example, the median OS for HBV infected HCC patients was 12.07 months, whereas the median OS for non-HBV infected HCC patients was 5.16 months (p=0.19) (FIGS. 5B and 8). Radiographic responses of target lesions are summarized in a waterfall plot (FIG. 7). Five subjects had >30% regression of target tumor lesion with best overall responses by RECIST 1.1 of 3 PR, 1 SD and 1 PD. Of these 5 subjects, the 3 subjects with PR were HBV positive, the subject with SD was HBV negative, and the subject with PD was HBV negative. In addition, the disease control rate (DCR) for all subjects was 54.7% (95% CI: 40.4%, 68.4%). By HBV status, the DCR was 91.7% (95% CI: 61.5%, 99.8%) for subjects who were HBV positive and 43.9% (95% CI: 28.5%, 60.3%) for those who were HBV negative (p=0.0066) (FIG. 8).

The rate of target tumor shrinkage (i.e., lesions reducing in size relative to screening) for all subjects was 45.3% (95% CI: 31.6%, 59.6%). By HBV status, the target tumor shrinkage rate was 66.7% (95% CI: 34.9, 90.1%) for subjects who were HBV positive was and 39.0% (95% CI: 24.2%, 55.5%) for those who were HBV negative (data not shown).

Illustrative examples of radiographic improvement in two patients treated with Compound 1 are shown in FIG. 9. Patient A shows regression of intrathoracic metastases at the first on-treatment restaging compared to baseline. Patient B shows intrahepatic tumor regression at the first on-treatment restaging compared to baseline.

Assessment of AFP and HBV Viral Load for the HCC Patients

For the HCC subjects, baseline and change from baseline in AFP and HBV viral load (HBsAg positive subjects only) were summarized with descriptive statistics. In addition, a Wilcoxon's signed rank test was conducted to analyze change from baseline in AFP at selected scheduled visits. The p-values of such tests were provided. Change from baseline in HBV viral load was analyzed similarly. The percentage of subjects with a >50% decline from baseline in AFP was summarized for the TP.

Examples of AFP reduction in two HBV positive patients who were treated with Compound 1 and showed PR are shown in FIG. 10. Both patients show early clinically significant, marked reduction of AFP on treatment compared to baseline elevated levels.

Discussion.

For the HCC TP, the overall response rate (ORR) was 5.7%. No subject experienced a CR. While modest, the objective response rate is comparable to that reported for sorafenib, a compound approved for the treatment of advanced HCC (Llovet et al, *N Engl J Med*, 2008, 359:78-90). A total of 49.1% of subjects showed a best response of SD, yielding a DCR of 54.7%. Relative to pretreatment, 45.3% of subjects showed target lesion regression. For the EE Population, also considered an important subgroup to evaluate for tumor response in early phase studies, the ORR was 7.3%, the DCR was 68.3%, and rate of tumor regression relative to pretreatment was 56.1%. For the 3 subjects who reached PR, the median duration of response (DOR) was 124.0 days. For the 26 subjects with a best response of SD, the median duration of SD was 112.0 days. For the TP, median PFS was 3.7 months and median OS was 30.0 weeks; the EE population outcomes were very similar.

Although not always statistically significant, all response outcomes were numerically more favorable in the subset of HCC subjects who were HBV positive compared with those with other risk factors (hepatitis C virus or non-infectious). All 3 subjects achieving PR were HBV positive, yielding an ORR of 25% compared with 0% in the HBV negative subgroups. The DCR was 91.7% versus 43.9%, the tumor regression rate relative to baseline was 66.7% versus 39.0%, median PFS was 14.8 versus 14.4 weeks, and median OS was 52.4 versus 22.4 weeks. These differences could not be completely explained by imbalances for baseline disease characteristics although HBV positive subjects were younger, male, and primarily Asian.

Conclusion.

Treatment with Compound 1 showed encouraging preliminary evidence of antitumor activity in subjects with HCC. This was especially true for the subset of HCC subjects considered HBV positive. Compound 1 was well tolerated in these subjects, with a side effect profile comparable with other drugs targeting the mTOR pathway. Based on safety, PD, and efficacy data in this study, a starting dose of 30 mg daily is proposed.

6.2 Clinical Study 2

An Open-label Phase 2 Trial of Dual TORC1/TORC2 Inhibitor Compound 1 in HBV+ Advanced Hepatocellular Carcinoma (HCC) Subjects Who Have Received at Least One Prior Line of Systemic Therapy.

Indication.

Hepatitis B virus (HBV) positive, unresectable HCC subjects who have received at least one prior line of systemic therapy.

Objectives.

The primary objectives of the trial are: To evaluate pharmacokinetics (PK), safety, tolerability and overall response rate (ORR) of Compound 1 in HBV+ HCC subjects who have received at least one prior line of systemic therapy.

The secondary objectives of the trial are: To evaluate overall survival (OS), time to progression (TTP), progression-free survival (PFS), disease control rate (DCR), duration of response (DOR), time to response (TTR), and survival rate.

Trial Design.

This trial is an Asian multi-regional clinical trial (MRCT) in which Compound 1 will be administered orally to hepatitis B positive (HBV+) HCC subjects who have received at least one prior line of systemic therapy. It is designed as an open-label phase 2 trial evaluating the pharmacokinetics (PK), safety, tolerability and efficacy of oral Compound 1 administered daily until the radiologic disease progression (according to RECIST 1.1) or intolerable toxicity.

Study Population.

Number and Population of Subjects: Approximately 30 HBV+, unresectable HCC subjects who have received at least one prior line of systemic therapy will be enrolled in this trial, including 6 at the dose of 15 mg and 24 at the dose of 30 mg. If the ORR in subjects with starting dose of 30 mg is greater than 15%, then this study may be expanded to enroll additional approximately 96 subjects (approximately 120 subjects receiving the 30 mg starting dose level in total) using ORR as the primary endpoint, to further evaluate the efficacy and safety.

Inclusion Criteria:

Male or female, ≥18 years of age at the time the ICF is signed; Confirmed pathologic or radiologic diagnosis of HCC according to the American Association for the Study of Liver Disease (AASLD) guidelines; Unresectable stage B (intermediate) or C (advanced) HCC according to the Barcelona Clinic Liver Cancer (BCLC) staging. If stage B, the subject must have progressed after, or not be eligible for, surgical or locoregional therapy; HBV+ is defined as chronic HBV infection or a history of HBV infection, based on any of the following serologic results: HBcAb+, HBsAg+, HBV-DNA+; Received at least one prior line of systemic therapy (with radiologic disease progression during or following sorafenib and/or chemotherapy). Subjects with alternative treatments such as regorafenib and/or anti PD-1 antibodies etc. approved by local health authorities are allowed to enter study if they meet all other inclusion/exclusion criteria; Chemotherapy includes FOLFOX (fluorouracil, leucovorin and oxaliplatin) or any other platinum-containing regimen; Chemotherapy two cycles; ECOG performance status score of 0 or 1; Satisfactory serum chemistry results, evidenced by the following: AST (SGOT) and ALT (SGPT)≤5× upper limit of normal (ULN); Total bilirubin ≤2×ULN; Creatinine ≤1.5×ULN or 24-hour clearance 50 mL/min; Adequate bone marrow function, evidenced by the following: Absolute neutrophil count (ANC) ≥1.5×10$^9$ cells/L, Platelets ≥75×10$^9$ cells/L, Hemoglobin ≥9 g/dL, Child-Pugh A (score 5 or 6 only) without encephalopathy; Male subjects (including those who have had a vasectomy) must agree to use a condom during sexual intercourse with females of child-bearing potential, and shall not conceive a child starting from the time of ICF signature, while on study medication, and for 3 months after the last dose of study drug; Female subjects of child-bearing potential must have both of the following: Agree to the use of two study physician-approved contraceptive methods simultaneously, or practice complete abstinence starting at the time of ICF signature, while on study medication, and for 28 days following the last dose of study drug. True abstinence: When this is in line with the preferred and usual lifestyle of the subject. Periodic abstinence (e.g., calendar, ovulation, symptothermal, post-ovulation methods) and withdrawal are not acceptable methods of contraception. Acceptable contraceptive methods include: Oral, injectable, or implantable hormonal contraceptive; intra-uterine device; barrier contraceptive with spermicide; or vasectomized partner, together with at least one barrier method. Have negative serum pregnancy test result at screening, confirmed by negative urine pregnancy test within 72 hours prior to first dose of study drug (if serum test occurred >72 hours from first dose); pregnancy test must have a sensitivity of at least 25 mIU/mL.

Exclusion Criteria:

The presence of any of the following will exclude a subject from enrollment: Intolerant to sorafenib/regorafenib, e.g., the subject must have discontinued either drug due to toxicity; Symptomatic central nervous system metastases. Brain metastases that have previously been treated and are stable for 4 weeks before the first dose date are allowed; Received sorafenib/regorafenib within 14 days prior to Screening; Locoregional HCC therapy (e.g., TACE, RFA), systemic chemotherapy, hormonal therapy (e.g., tamoxifen) or investigational therapy within 4 weeks (or 5 half-lives, whichever is shorter) prior to Screening; Tested positive for both HBV and hepatitis C virus (HCV). (HCV positive is defined as anti-HCV or HCV-RNA positive); Life expectancy of less than 3 months; Prior therapy with mTOR (TORC1 and/or TORC2) inhibitors including sirolimus, temsirolimus, everolimus, and other investigational or approved mTOR/PI3K/AKT inhibitors; Major surgery or significant trauma within 28 days prior to Screening; Not recovered from the acute toxic effects of prior anticancer therapy, radiation or major surgery/significant trauma at Screening; Minor surgery within 7 days prior to Screening (excluding the placement of central/peripheral lines or skin biopsy); Receiving active, ongoing treatment with systemic corticosteroids at a prednisone equivalent dose of ≥10 mg daily or other systemic immune system modulators; Uncontrolled diabetes, defined as HbA1c >8%; Prior organ transplant; Persistent diarrhea or malabsorption ≥National Cancer Institute (NCI) Common Terminology Criteria for Adverse Events (CTCAE, Version 4.03) grade 2, despite medical management, or any significant gastrointestinal disorder that could affect the absorption of study drug; Clinically significant bleeding, especially from esophageal varices, requiring medical intervention within 28 days prior to Screening; Known history or current diagnosis of human immunodeficiency virus (HIV) infection, regardless of treatment status; Concurrent active second malignancy for which the subject is receiving therapy, excluding non-melanomatous skin cancer, non-progressive prostate cancer treated with hormonal therapy, or carcinoma in situ of the cervix. Any cancer curatively treated >5 years prior to entry is permitted; Uncontrolled intercurrent illness including, but not limited to ongoing or active infection (e.g., tuberculosis) requiring antibiotic, antifungal, or antiviral therapy (other than anti-HBV therapy), symptomatic heart failure, cardiac arrhythmia, acute or chronic pancreatitis or psychiatric illness/social situations that would limit compliance with study requirements; Significant medical conditions, laboratory abnormalities, or psychiatric illnesses that would prevent the subject from complying fully with this protocol; Any condition including the presence of laboratory abnormalities, which places subjects at unacceptable risk should they participate in the trial; Any condition that confounds the ability to interpret data from the trial.

Length of Trial.

Enrollment of the estimated 30 subjects is expected to take approximately 4 months. Completing PK, safety and preliminary efficacy evaluations is expected to take approximately 4 months. The end of Study is defined as either the date of the last visit of the last subject to complete the trial, or the date of receipt of the last data point (e.g., date of death) from the last subject that is required for primary analysis, whichever is the earlier date.

Study Treatments.

The starting dose of Compound 1 will be 15 mg daily for 28 days each cycle for the first 6 fully evaluable (including PK outcomes) subjects. Providing dose-limiting toxicity (DLT) occurs in less than 2 of 6 subjects who complete Cycle 1, additional 24 subjects will be enrolled at the starting dose of 30 mg daily. Subjects who tolerated the 15 mg dose level may then dose-escalate to 30 mg at the Investigator's discretion until enrollment of 30 mg group starts. If the ORR in subjects with starting dose of 30 mg is greater than 15%, then this study may be expanded to enroll additional approximately 96 subjects (approximately 120 subjects in total) using ORR as the primary end point, to further evaluate the efficacy and safety.

All subjects will receive Compound 1 once daily in continuous 28-day cycles (except cycle 1) until the appearance of radiologic disease progression, toxicity, subject or physician decision or death. At the discretion of the Investigator, treatment may continue beyond radiologic progression until clear symptomatic deterioration if no other treatment options are available. Dose interruptions of up to 3 weeks, and up to two dose reductions (to 20 mg and 15 mg) will be allowed to mitigate toxicity. Dose reescalation will be allowed only one time if the same toxicity does not recur at the reduced dose for least one cycle (4 weeks).

Antiviral therapy is required, and HBV-DNA viral load will be monitored in all subjects with chronic HBV infection. Serum AST/ALT is also monitored.

After cessation of study drug treatment, subsequent anticancer therapy and survival status will be followed in all subjects until death.

Overview of Efficacy Assessments.

Subjects will be evaluated for tumor response and progression according to RECIST 1.1 guidelines every 8 weeks (±5 days) until radiologic disease progression, death or withdrawal of consent. mRECIST may be also used when the trial is expanded, if necessary.

All anticancer treatments administered, especially for HCC, following the last dose of study drugs will be captured until death or withdrawal of consent. Disease progression and date of progression on each subsequent therapy will be documented. Following disease progression, survival will be followed every 8 weeks (±1 week) until death or withdrawal of consent.

Overview of Safety Assessments.

All subjects will be monitored for adverse events, starting from the time the subject signs the informed consent form (ICF) until 28 days after the last dose of study drug. A thorough evaluation of medical conditions will be conducted during screening for eligibility. Vital signs, laboratory assessments (e.g. serum chemistry, hematology, fasting plasma glucose, glycated hemoglobin [HbA1c]), 12-lead electrocardiogram (ECGs), and ECOG performance status will be monitored. Contraception must be practised during the trial to avoid pregnancy in trial subjects and their partners, and females of child-bearing potential will have regular pregnancy testing.

Overview of Pharmacokinetic Assessments.

Blood samples will be collected for intensive sampling in all 30 subjects in order to estimate the PK of Compound 1 and metabolites in Asian subjects.

Overview of Exposure-Response Analyses.

Exposure-response analyses will be performed to evaluate relationships between Compound 1 and/or M1 exposure and clinical outcomes of efficacy and safety.

Overview of Biomarker Assessments.

Biomarkers will be evaluated. Inhibition of pAKT, pS6RP, p4EB-P1, and/or other relevant biomarkers will be assayed in peripheral blood and tumor. Correlative analyses will be completed for drug exposure, adverse events and clinical outcomes as appropriate.

6.3 Clinical Study 3

A Phase 2 Open-Label Trial of Dual TORC1/TORC2 Inhibitor Compound 1 Combined with Nivolumab in HBV+ Advanced Hepatocellular Carcinoma (HCC) Subjects Previously Treated with Sorafenib Indication.

Hepatitis B virus (HBV) positive, unresectable HCC subjects previously treated with sorafenib.

Objectives.

The primary objectives of the trial are: To evaluate safety, tolerability and overall response rate (ORR) of Compound 1 combined with nivolumab in HBV+ HCC subjects previously treated with sorafenib.

The secondary objectives of the trial are: To evaluate duration of response (DOR), survival rate, disease control rate (DCR), time to response (TTR), time to progression (TTP), progression-free survival (PFS), and overall survival (OS).

Trial Design.

This trial is an Asian multi-regional clinical trial (MRCT) in which Compound 1 in low dose and following high dose will be administered orally in combination with standard dose nivolumab in HBV+ advanced HCC subjects previously treated with sorafenib. This is an open-label phase 2 trial to evaluate the tolerability, safety and efficacy of Compound 1 in combination with nivolumab.

Study Population.

Number and Population of Subjects: Approximately 30-42 HBV+, unresectable HCC subjects previously treated with sorafenib will be enrolled first. If the observed ORR of the combination therapy reaches approximately 20%, then this trial may be expanded to approximately 126 subjects in total using ORR as the primary end point, to further evaluate the efficacy and safety.

Inclusion Criteria:

Male or female, ≥18 years of age at the time the ICF is signed; Confirmed pathologic or radiologic diagnosis of HCC according to the American Association for the Study of Liver Disease (AASLD) guidelines; Unresectable stage B (intermediate) or C (advanced) HCC according to the Barcelona Clinic Liver Cancer (BCLC) staging. If stage B, the subject must have progressed after, or not be eligible for, surgical or locoregional therapy; Measurable disease as defined by RECIST 1.1; Radiologic disease progression following sorafenib treatment. Subjects with alternative treatments such as regorafenib approved by local health authorities are allowed to enter study if they meet all other inclusion/exclusion criteria; HBV+ is defined as chronic HBV infection or a history of HBV infection, based on any of the following serologic results: HBcAb+, HBsAg+, HBV-DNA+; Patients with active HBV infection are required to be receiving effective antiviral therapy and their viral load should be <500 IU/mL before first study dose; ECOG performance status score of 0 or 1; Satisfactory serum chemistry results, evidenced by the following: AST (SGOT) and ALT (SGPT)≤5× upper limit of normal (ULN), Total bilirubin ≤2×ULN, Creatinine ≤1.5×ULN or 24-hour clearance ≥50 mL/min; Adequate bone marrow function, evidenced by the following: Absolute neutrophil count (ANC) ≥1.5×10$^9$ cells/L, Platelets ≥75×10$^9$ cells/L, Hemoglobin ≥9 g/dL, Child-Pugh A (score 5 or 6 only) with no encephalopathy; Male subjects (including those who have had a vasectomy) must agree to use a condom during sexual intercourse with females of child-bearing potential, and shall not conceive a child starting from the time of ICF signature, while on study medication, and for 5 months after the last dose of study drug; Female subjects of child-bearing potential must have both of the following: Agree to the use of two study physician-approved contraceptive methods simultaneously, or practice complete abstinence starting at the time of ICF signature, while on study medication, and for 5 months following the last dose of study drug. True abstinence: When this is in line with the preferred and usual lifestyle of the subject. Periodic abstinence (e.g., calendar, ovulation, symptothermal, post-ovulation methods) and withdrawal are not acceptable methods of contraception. Acceptable contraceptive methods include: Oral, injectable, or implantable hormonal contraceptive; intra-uterine device; barrier contraceptive with spermicide; or vasectomized partner, together with at least one barrier method. Have negative serum pregnancy test result at screening, confirmed by negative urine pregnancy test within 72 hours prior to first dose of study drug (if serum test occurred >72 hours from first dose); pregnancy test must have a sensitivity of at least 25 mIU/mL.

Exclusion Criteria:

The presence of any of the following will exclude a subject from enrollment: Intolerant to sorafenib, i.e., the subject must have discontinued drug due to toxicity; Symptomatic central nervous system metastases. Metastases previously treated and stable for ≥4 weeks before the first dose date are allowed; History of hepatic encephalopathy; Received sorafenib within 14 days prior to first dose of study drug; Locoregional HCC therapy (e.g., TACE, RFA), systemic chemotherapy, hormonal therapy (e.g., tamoxifen) or investigational therapy within 4 weeks (or 5 half-lives, whichever is shorter) prior to first dose of study drug; Plan to receive locoregional HCC therapy (e.g., TACE, RFA) during the trial; Co-infection with HBV and HCV/HDV hepatitis virus infection; Life expectancy of less than 3 months; Prior therapy with mTOR (TORC1 and/or TORC2) inhibitors including sirolimus, temsirolimus, everolimus, and other investigational or approved mTOR/PI3K/AKT inhibitors; Prior therapy with any medication targeting T-cell activation or checkpoint pathways (including those targeting PD-1, PD-L1 or PD-L2, CD137, or cytotoxic T-lymphocyte antigen [CTLA-4]); History of autoimmune disease; Prior or current clinically significant ascites; Major surgery or significant trauma within 28 days prior to Screening; Not recovered from the acute toxic effects of prior anticancer therapy, radiation or major surgery/significant trauma at Screening; Minor surgery within 7 days prior to Screening (excluding the placement of central/peripheral lines or skin biopsy); Receiving active, ongoing treatment with systemic corticosteroids at a prednisone equivalent dose of ≥10 mg daily or other systemic immune system modulators; Uncontrolled diabetes, defined as HbAlc>8%; Prior organ transplant; Persistent diarrhea or malabsorption National Cancer Institute (NCI) Common Terminology Criteria for Adverse Events (CTCAE, Version 4.03) grade 2, despite medical management, or any significant gastrointestinal disorder that could affect the absorption of study drug; Clinically significant bleeding, especially from esophageal varices, requiring medical intervention within 28 days prior to Screening; Known history or current diagnosis of human immunodeficiency virus (HIV) infection, regardless of treatment status; Concurrent active second malignancy for which the subject is receiving therapy, excluding non-melanomatous skin cancer, non-progressive prostate cancer treated with hormonal therapy, or carcinoma in situ of the cervix. Any cancer curatively treated >5 years prior to entry is permitted; Uncontrolled intercurrent illness including, but not limited to ongoing or active infection (e.g., tuberculosis) requiring antibiotic, antifungal, or antiviral therapy (other than anti-HBV therapy), symptomatic heart failure, cardiac arrhythmia, acute or chronic pancreatitis or psychiatric illness/social situations that would limit compliance with study requirements; Significant medical conditions, laboratory abnormalities, or psychiatric illnesses that would prevent the subject from complying fully with this protocol; Any condition including the presence of laboratory abnormalities, which places subjects at unacceptable risk should they participate in the trial; Any condition that confounds the ability to interpret data from the trial.

Length of Trial.

Enrollment of the estimated 30-42 subjects is expected to take approximately 5 months. Completing tolerability, safety and preliminary efficacy evaluations is expected to take approximately 8 months. The end of study is defined as either the date of the last visit of the last subject to complete the trial, or the date of receipt of the last data point (e.g., date of death) from the last subject that is required for primary analysis, whichever is the earlier date.

Study Treatments.

Compound 1 will be administrated at different daily dose level (15 mg, 30 mg or 20 mg) orally at the following schedule in combination with nivolumab given in a standard schedule (240 mg every 2 weeks, intravenous infusion). The dose escalation scheme will be based on a modified 3+3 design.

Initially 3 subjects will be enrolled in the cohort of Compound 1 15 mg combination therapy: If no dose-limiting toxicity (DLT) occurs, 3 new subjects will be enrolled in the cohort of Compound 1 30 mg combination therapy. If 1 DLT occurs, additional 3 subjects will be enrolled in the Compound 1 15 mg combination cohort. Providing no further DLTs occur, 3 new subjects will be evaluated in the cohort of Compound 1 30 mg combination. If 2 or more DLTs occur, it will be discussed with Safety Review Committee and Principle Investigator(s) to discontinue trial or explore other appropriate trial design.

For the initial 3 subjects in the cohort of Compound 1 30 mg combination: If no DLT occurs, 24 new subjects will be enrolled at the dose level of Compound 1 30 mg combination. If 1 DLT occurs, additional 3 subjects will be enrolled in the Compound 1 30 mg combination cohort. Providing no more than 1 DLT occurs in 6 subjects in the cohort of Compound 1 30 mg combination, additional 24 subjects will be enrolled in the cohort of Compound 1 30 mg combination. If 2 of 3 or 6 subjects at the dose level of Compound 1 30 mg combination therapy experience DLTs, 3 new subjects will be enrolled in a cohort of Compound 1 20 mg combination. If no DLT occurs in the 3 subjects at the dose level of Compound 1 20 mg combination, the study will proceed to enroll additional 24 subjects at the dose level of Compound 1 20 mg combination therapy. If 1 DLT occurs, additional 3 subjects will be enrolled at the same dose level of Compound 1 20 mg combination. Providing DLTs occur in less than 2 of 6 subjects in the cohort of Compound 1 20 mg combination, the study will proceed to enroll additional 24 subjects in the cohort of Compound 1 20 mg combination. If 2 of 3 or 6 subjects at the dose level of Compound 1 20 mg combination therapy experienced DLTs, the study will proceed to enroll additional 24 subjects in the cohort of Compound 1 15 mg combination.

If the ORR of the combination therapy at optimal dose level reaches about 20%, then this study will be expanded to a total of about 126 subjects using ORR as the primary endpoint, in order to further evaluate the efficacy and safety.

DLTs include early hyperglycemia, rash, fatigue, and mucositis, any of which ≥grade 3, and hepatic impairment according to study CheckMate 040 results, which commences within 6 weeks of first dose.

All subjects will receive Compound 1 orally once daily in continuous 28-day cycles in combination with nivolumab intravenous infusion every 2 weeks until the appearance of radiologic disease progression (according to RECIST 1.1), unacceptable toxicity, subject or physician decision, withdrawal of consent, or death. At the discretion of the Investigator, treatment may continue beyond radiologic progression until clear symptomatic deterioration if no other treatment options are available.

Antiviral therapy is required, and HBV-DNA viral load will be monitored in all subjects with chronic HBV infection. Serum AST/ALT is also monitored.

After cessation of study drug treatment, subsequent anti-cancer therapy and survival status will be followed in all subjects until death.

Overview of Efficacy Assessments.

Subjects will be evaluated for tumor response and progression according to RECIST 1.1 guidelines until radiologic disease progression, death or withdrawal of consent. mRECIST may be also used when the trial is expanded, if necessary. The tumor response assessments will be performed every 6 weeks (±5 days) for first 24 weeks, and every 12 weeks (±1 week) thereafter.

All anticancer treatments administered, especially for HCC, following the last dose of combination treatment will be captured until death or withdrawal of consent. Disease progression and date of progression on each subsequent therapy will be documented. Following disease progression, survival will be followed every 12 weeks (±1 week) until death or withdrawal of consent.

Overview of Safety Assessments.

All subjects will be monitored for adverse events, starting from the time the subject signs the informed consent form (ICF) until 28 days after the last dose of combination treatment. A thorough evaluation of medical conditions will be conducted during screening for eligibility. Vital signs, laboratory assessments (e.g. serum chemistry, hematology, fasting plasma glucose, glycated hemoglobin [HbA1c]), 12-lead electrocardiogram (ECGs), and ECOG performance status will be monitored. Contraception must be practiced during the trial to avoid pregnancy in trial subjects and their partners, and females of child-bearing potential will have regular pregnancy testing.

Overview of Biomarker Assessments.

Biomarkers will be evaluated. Inhibition of pAKT, pS6RP, p4EB-P1, and/or other relevant biomarkers will be assayed in peripheral blood and tumor tissue. Correlative analyses will be completed for drug exposure, adverse events and clinical outcomes as appropriate.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed is:

1. A method for treating hepatocellular carcinoma (HCC) characterized by hepatitis B virus (HBV) infection in a patient, comprising administering an effective amount of 7-(6-(2-hydroxypropan-2-yl)pyridin-3-yl)-1-((trans)-4-methoxycyclohexyl)-3,4-dihydropyrazino[2,3-b]pyrazin-2 (1H)-one or a pharmaceutically acceptable salt or tautomer thereof to the patient having HCC characterized by HBV infection.

2. A method for treating HCC characterized by HBV infection in a patient, comprising screening the patient's HCC for HBV infection, and administering an effective amount of 7-(6-(2-hydroxypropan-2-yl)pyridin-3-yl)-1-((trans)-4-methoxycyclohexyl)-3,4-dihydropyrazino[2,3-b]pyrazin-2(1H)-one or a pharmaceutically acceptable salt or tautomer thereof to the patient having HCC characterized by HBV infection.

3. A method for selecting a patient having HCC for treatment with 7-(6-(2-hydroxypropan-2-yl)pyridin-3-yl)-1-((trans)-4-methoxycyclohexyl)-3,4-dihydropyrazino[2,3-b]pyrazin-2(1H)-one or a pharmaceutically acceptable salt or tautomer thereof, comprising a) obtaining a biological test sample from the patient; b) analyzing the sample for HBV infection; c) selecting the patient having HCC for treatment with 7-(6-(2-hydroxypropan-2-yl)pyridin-3-yl)-1-((trans)-4-methoxycyclohexyl)-3,4-dihydropyrazino[2,3-b]pyrazin-2(1H)-one or a pharmaceutically acceptable salt or tautomer thereof if HBV infection is determined in the sample.

4. A method for predicting response to treatment with 7-(6-(2-hydroxypropan-2-yl)pyridin-3-yl)-1-((trans)-4-methoxycyclohexyl)-3,4-dihydropyrazino[2,3-b]pyrazin-2(1H)-one or a pharmaceutically acceptable salt or tautomer thereof in a patient having HCC, the method comprising: a) obtaining a biological test sample from the patient; b) analyzing the sample for HBV infection; c) predicting an increased likelihood of response to treatment with 7-(6-(2-hydroxypropan-2-yl)pyridin-3-yl)-1-((trans)-4-methoxycyclohexyl)-3,4-dihydropyrazino[2,3-b]pyrazin-2(1H)-one or a pharmaceutically acceptable salt or tautomer thereof in the patient having HCC if HBV infection is determined in the sample.

5. A method for predicting therapeutic efficacy of 7-(6-(2-hydroxypropan-2-yl)pyridin-3-yl)-1-((trans)-4-methoxycyclohexyl)-3,4-dihydropyrazino[2,3-b]pyrazin-2(1H)-one or a pharmaceutically acceptable salt or tautomer thereof in a patient having HCC, the method comprising: a) obtaining a biological test sample from the patient; b) analyzing the sample for HBV infection; c) predicting an increased likelihood of therapeutic efficacy of 7-(6-(2-hydroxypropan-2-yl)pyridin-3-yl)-1-((trans)-4-methoxycyclohexyl)-3,4-dihydropyrazino[2,3-b]pyrazin-2(1H)-one or a pharmaceutically acceptable salt or tautomer thereof in the patient having HCC if HBV infection is determined in the sample.

6. The method of claim 3, further comprising a step d) administering an effective amount of 7-(6-(2-hydroxypropan-2-yl)pyridin-3-yl)-1-((trans)-4-methoxycyclohexyl)-3,4-dihydropyrazino[2,3-b]pyrazin-2(1H)-one or a pharmaceutically acceptable salt or tautomer thereof to the patient having HCC.

7. The method of claim 1, wherein HBV infection is determined by at least one of the variables selected from the group consisting of: patient history of HBV, prior or current treatment for HBV, cirrhosis attributed to HBV, the presence of HBV proteins or antigens, the presence of antibodies to HBV proteins or antigens, HBV viral load, and the presence of HBV DNA.

8. The method of claim 7, wherein HBV infection is determined by patient history of HBV.

9. The method of claim 7, wherein HBV infection is determined by prior treatment for HBV.

10. The method of claim 7, wherein HBV infection is determined by current treatment for HBV.

11. The method of claim 7, wherein HBV infection is determined by cirrhosis attributed to HBV.

12. The method of claim 7, wherein HBV infection is determined by the presence of HBV proteins or antigens.

13. The method of claim 7, wherein HBV infection is determined by the presence of antibodies to HBV proteins or antigens.

14. The method of claim 7, wherein HBV infection is determined by HBV viral load.

15. The method of claim 7, wherein HBV infection is determined by the presence of HBV DNA.

16. The method of claim 1, wherein HBV infection is determined by at least one of the variables selected from the group consisting of: the presence of HBV surface antigen (HBsAG), the presence of HBV core antigen (HBcAG), the presence of HBV envelope antigen (HBeAg), the presence of HBV x antigen (HBxAg), the presence of HBV core-related antigen (HBcrAg), the presence of antibody to HBV surface antigen (anti-HBsAg), the presence of antibody to HBV core antigen (anti-HBcAg), the presence of antibody to HBV envelope antigen (anti-HBeAg), the presence of antibody to HBV x antigen (anti-HBxAg), the presence of antibody to HBV core-related antigen (anti-HBcrAg), the use of HBV medications, HBV viral load, the presence of HBV DNA, the presence of HBV mRNA, and the presence of HBV protein.

17. The method of claim 16, wherein HBV infection is determined by the presence of HBsAg.

18. The method of claim 16, wherein HBV infection is determined by the presence of HBcAg.

19. The method of claim 16, wherein HBV infection is determined by the presence of HBeAg.

20. The method of claim 16, wherein HBV infection is determined by the presence of HBxAg.

21. The method of claim 16, wherein HBV infection is determined by the presence of HBcrAg.

22. The method of claim 16, wherein HBV infection is determined by the presence of anti-HBsAg.

23. The method of claim 16, wherein HBV infection is determined by the presence of anti-HBcAg.

24. The method of claim 16, wherein HBV infection is determined by the presence of anti-HBeAg.

25. The method of claim 16, wherein HBV infection is determined by the presence of anti-HBxAg.

26. The method of claim 16, wherein HBV infection is determined by the presence of anti-HBcrAg.

27. The method of claim 16, wherein HBV infection is determined by the use of HBV medications.

28. The method of claim 16, wherein HBV infection is determined by HBV viral load.

29. The method of claim 16, wherein HBV infection is determined by the presence of HBV DNA.

30. The method of claim 16, wherein HBV infection is determined by the presence of HBV mRNA.

31. The method of claim 16, wherein HBV infection is determined by the presence of HBV protein.

32. The method of claim 1, wherein 7-(6-(2-hydroxypropan-2-yl)pyridin-3-yl)-1-((trans)-4-methoxycyclohexyl)-3,4-dihydropyrazino[2,3-b]pyrazin-2(1H)-one or a pharmaceutically acceptable salt or tautomer thereof is administered in combination with a second therapeutic agent to the HCC patient characterized by HBV infection.

33. The method of claim 32, wherein the second therapeutic agent is sorafenib.

34. The method of claim 32, wherein the second therapeutic agent is 3-(5-amino-2-methyl-4-oxo-4H-quinazolin-3-yl)-piperidine-2,6-dione (Compound 2).

35. The method of claim 32, wherein the second therapeutic agent is an immune check point inhibitor.

36. The method of claim 1, wherein 7-(6-(2-hydroxypropan-2-yl)pyridin-3-yl)-1-((trans)-4-methoxycyclohexyl)-3,4-dihydropyrazino[2,3-b]pyrazin-2(1H)-one or a pharmaceutically acceptable salt or tautomer thereof is administered in combination with a second and a third therapeutic agent to the HCC patient characterized by HBV infection.

37. The method of claim 36, wherein the second and the third therapeutic agents are selected from the group consisting of sorafenib, 3-(5-amino-2-methyl-4-oxo-4H-quinazolin-3-yl)-piperidine-2,6-dione (Compound 2), and an immune check point inhibitor.

38. The method of claim 37, wherein the immune check point inhibitor is nivolumab.

39. The method of claim 1, wherein the HCC is unresectable HCC.

40. The method of claim 1, wherein the HCC is previously untreated HCC.

41. The method of claim 1, wherein the HCC is previously treated HCC, wherein the previous treatment comprises sorafenib.

42. The method of claim 1, wherein the HCC is previously treated HCC, wherein the previous treatment comprises chemotherapy.

\* \* \* \* \*